United States Patent
Knueppel et al.

(10) Patent No.: US 9,504,251 B2
(45) Date of Patent: Nov. 29, 2016

(54) PESTICIDAL COMPOSITIONS AND RELATED METHODS

(71) Applicant: Dow AgroSciences LLC, Indianapolis, IN (US)

(72) Inventors: Daniel I. Knueppel, Zionsville, IN (US); Maurice C. Yap, Zionsville, IN (US); Michael T. Sullenberger, Westfield, IN (US); Ricky Hunter, Westfield, IN (US); Monica B. Olson, Lebanon, IN (US); Frank J. Wessels, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 15 days.

(21) Appl. No.: 14/711,559

(22) Filed: May 13, 2015

(65) Prior Publication Data
US 2015/0327551 A1    Nov. 19, 2015

Related U.S. Application Data

(60) Provisional application No. 61/994,660, filed on May 16, 2014.

(51) Int. Cl.
| | | |
|---|---|---|
| *A01N 43/90* | (2006.01) | |
| *A01N 27/00* | (2006.01) | |
| *A01N 47/02* | (2006.01) | |
| *C07D 471/04* | (2006.01) | |
| *A01N 37/20* | (2006.01) | |

(52) U.S. Cl.
CPC .............. *A01N 43/90* (2013.01); *A01N 27/00* (2013.01); *A01N 47/02* (2013.01); *C07D 471/04* (2013.01)

(58) Field of Classification Search
CPC ...... A01N 43/90; A01N 27/00; A01N 37/20; A01N 47/02; C07D 471/04
See application file for complete search history.

(56) References Cited

U.S. PATENT DOCUMENTS 7,135,469 B2 * 11/2006 Pinto .................... C07D 471/04
                                                             514/234.2
2007/0027034 A1    2/2007 Tank 2010/0173959 A1    7/2010 Renold et al.
2012/0329649 A1   12/2012 Hunter et al.
2013/0089622 A1    4/2013 Trullinger et al.
2014/0296068 A1*  10/2014 Garizi .................... A01N 43/54
                                                               504/100

FOREIGN PATENT DOCUMENTS

WO    2013106254 A1    7/2013

OTHER PUBLICATIONS

Mallis, Handbook of Pest Control—The Behavior, Life History, and Control of Household Pests; 2004, 9th Edition, GIE Media Inc.
International Search Report for International Application No. PCT/US2015/030662, dated Jul. 8, 2015, 4 pages.
Written Opinion for International Application No. PCT/US2015/030662, dated Jul. 8, 2015, 5 pages.

* cited by examiner

*Primary Examiner* — Jane C Oswecki
(74) *Attorney, Agent, or Firm* — Carl D. Corvin; Magleby Cataxinos & Greenwood

(57) ABSTRACT

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides. This document discloses molecules having the following formula I, or any agriculturally acceptable salt thereof, wherein $R^1$, $R^2$, $R^3$, $R^4$, $R^5$, $R^6$, $R^7$, $R^8$, $R^9$, $X^1$, Q, and n are as described herein.

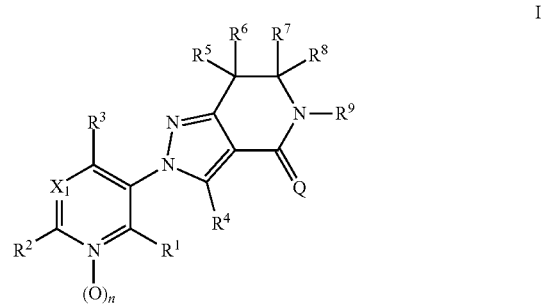

20 Claims, No Drawings

PESTICIDAL COMPOSITIONS AND RELATED METHODS

CROSS-REFERENCE TO RELATED APPLICATION

This application claims the benefit of the U.S. Provisional Patent Application Ser. No. 61/994,660, filed May 16, 2015, the disclosure of which is hereby incorporated herein in its entirety by this reference.

TECHNICAL FIELD

This disclosure relates to the field of molecules having pesticidal utility against pests in Phyla Arthropoda, Mollusca, and Nematoda, processes to produce such molecules, intermediates used in such processes, pesticidal compositions containing such molecules, and processes of using such pesticidal compositions against such pests. These pesticidal compositions may be used, for example, as acaricides, insecticides, miticides, molluscicides, and nematicides.

BACKGROUND

Controlling pest populations is essential to human health, modern agriculture, food storage, and hygiene. There are more than ten thousand species of pests that cause losses in agriculture and the world-wide agricultural losses amount to billions of U.S. dollars each year. Accordingly, there exists a continuous need for new pesticides, and for methods of producing and using such pesticides.

DETAILED DESCRIPTION

Definitions

The examples given in these definitions are generally nonexhaustive and must not be construed as limiting this disclosure. It is understood that a substituent should comply with chemical bonding rules and steric compatibility constraints in relation to the particular molecule to which it is attached.

"Alkyl" means and includes an acyclic, saturated, branched or unbranched hydrocarbon. Non-limiting examples may include meatyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, or decyl.

"Cycloalkyl" means and includes a monocyclic or polycyclic saturated hydrocarbon. Non-limiting examples may include cyclopropyl, cyclobutyl, cyclopentyl, cyclohexyl, cycloheptyl, cyclooctyl, cyclodecyl, norbomyl, bicycle[2.2.2]octyl, or decahydronapthyl.

"Alkenyl" means and includes an acyclic, branched or unbranched hydrocarbon containing at least one carbon-carbon double bond. Non-limiting examples may include ethenyl, propenyl, butenyl, pentenyl, hexenyl, heptenyl, octenyl, nonenyl, or decenyl.

"Cycloalkenyl" means and includes a monocyclic or polycyclic hydrocarbon containing at least one carbon-carbon double bond. Non-limiting examples may include cyclopentenyl, cyclohexenyl, cycloheptenyl, cyclooctenyl, or cyclodecenyl.

"Alkynyl" means and includes acyclic, branched or unbranched hydrocarbon containing at least one carbon-carbon triple bond. Non-limiting examples may include ethynyl, propargyl, butynyl, pentynyl, hexynyl, heptynyl, octynyl, nonynyl, or decynyl.

"Cycloalkynyl" means and includes a monocyclic or polycyclic hydrocarbon containing at least one carbon-carbon triple bond. Non-limiting examples may include cycloheptynyl, cyclooctynyl, or cyclodecynyl.

"Aryl" means and includes an aromatic compound with or without any substitution, and may or may not include one or more heteroatoms. Non-limiting examples may include phenyl, naphthyl, or pyridyl.

"Alkoxy" means and includes an alkyl group containing at least one carbon-oxygen single bond. Non-limiting examples may include methoxy, ethoxy, propoxy, butoxy, cyclopropoxy, cyclobutoxy, or cyclopentoxy.

"Alkenyloxy" means and includes an alkenyl containing at least one carbon-oxygen single bond. Non-limiting examples may include allyloxy, butenyloxy, pentenyloxy, hexenyloxy, heptenyloxy, octenyloxy, nonenyloxy, or decenyloxy.

"Alkynyloxy" means and includes an alkynyl containing at least one carbon-oxygen single bond. Non-limiting examples may include pentynyloxy, hexynyloxy, heptynyloxy, octynyloxy, nonynyloxy, or decynyloxy.

"Cycloalkoxy" means and includes a cycloalkyl containing at least one carbon-oxygen single bond. Non-limiting examples may include cyclopropyloxy, cyclobutyloxy, cyclopentyloxy, cyclohexyloxy, cycloheptyloxy, cyclooctyloxy, cyclodecyloxy, norbomyloxy, or bicyclo[2.2.2]octyloxy.

"Cyclohaloalkyl" means and includes a monocyclic or polycyclic, saturated substituent comprising carbon, halogen, and hydrogen. Non-limiting examples may include 1-chlorocyclopropyl, 1-chlorocyclobutyl, or 1-dichlorocyclopentyl.

"Cycloalkenyloxy" means and include a cycloalkenyl further consisting of a carbon-oxygen single bond. Non-limiting examples may include cyclobutenyloxy, cyclopentenyloxy, cyclohexenyloxy, cycloheptenyloxy, cyclooctenyloxy, cyclodecenyloxy, norbomenyloxy, or bicyclo[2.2.2] octenyloxy.

"Alkylthio" means and includes an alkyl group containing at least one carbon-sulfur single bond.

"Haloalkylthio" means and includes an alkyl group containing at least one carbon-sulfur single bond and halogen atom.

"Halo" or "halogen" means and includes fluorine, chlorine, bromine, or iodine.

"Haloalkyl" means and includes an alkyl group substituted with at least one halogen atom.

"Haloalkoxy" means and includes an alkoxy group substituted with at least one halogen atom.

"Heteroatom" means and includes sulfur (S), oxygen (O), or nitrogen (N) atom.

"Heteroalkyl" means and includes an alkyl containing at least one sulfur (S), oxygen (O), or nitrogen (N) atom.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following

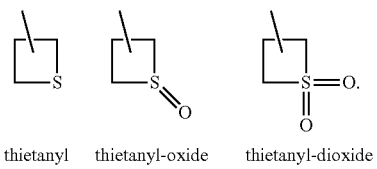

thietanyl    thietanyl-oxide    thietanyl-dioxide

"Pesticidally effective amount" means and includes an amount of active material that causes an adverse effect to the at least one insect, wherein the adverse effect may include deviations from natural development, killing, regulation, or the like.

"Control" or grammatical variations thereof means and includes regulating the number of living insects or regulating the number of viable eggs of the insects, or both.

"Synergistic effect" or grammatical variations thereof means and includes a cooperative action encountered in a combination of two or more active agents in which the combined activity of the two or more active agents exceeds the sum of the activity of each active agent alone.

Pesticidal Compounds

In one particular embodiment, a pesticidal composition comprises a compound of formula I, or any agriculturally acceptable salt thereof:

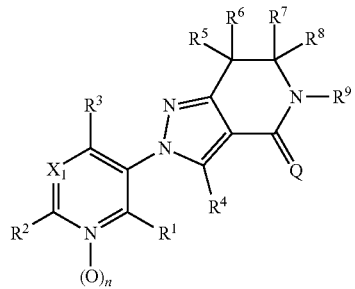

I wherein:

$R^1$, $R^2$, and $R^3$ is each independently selected from the group consisting of H, F, Cl, Br, I, CN, $NO_2$, OH, $C_1$-$C_4$ alkyl, $C_2$-$C_4$ alkenyl, $C_1$-$C_4$ haloalkyl, $C_1$-$C_4$ alkoxy, $C_1$-$C_4$ haloalkoxy, $C_3$-$C_6$ cycloalkyl, aryl, substituted aryl, $C_1$-$C_4$ alkylphenyl, phenyl, substituted phenyl, heterocyclyl, and substituted heterocyclyl, wherein each alkyl, alkenyl, haloalkyl, alkoxy, haloalkoxy, cycloalkyl, aryl, alkylphenyl, phenyl, and heterocycle is optionally substituted with one or more substituents independently selected from the group consisting of H, F, Cl, Br, I, CN, $NO_2$, OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

$R^4$, $R^5$, $R^6$, $R^7$, and $R^8$ is each independently selected from the group consisting of H, F, Cl, Br, CN, OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

$R^9$ is selected from the group consisting of H, $C_1$-$C_4$ alkyl, $C_2$-$C_4$ alkenyl, $C_1$-$C_4$ haloalkyl, ($C_1$-$C_4$ alkyl)($C_3$-$C_6$ cycloalkyl), $C_1$-$C_4$ alkylphenyl, $C_1$-$C_4$ haloalkylphenyl, aryl, substituted aryl, phenyl, pyridiyl, pyrimidyl, substituted phenyl, substituted pyridyl, ($C_1$-$C_4$ alkyl)C(=O)(phenyl), ($C_1$-$C_4$ alkyl)(haloalkyl)(phenyl), ($C_1$-$C_4$ alkylhaloalkyl)(alkyl), ($C_1$-$C_4$ alkyl)C(=O)O($C_1$-$C_4$ alkyl), ($C_1$-$C_4$ alkyl)C(=NOR$^{10}$)R$^{11}$, C(=O)($C_1$-$C_4$ alkyl)S(=O)$_m$($C_1$-$C_4$ alkyl), ($C_1$-$C_4$ alkyl)S(=O)$_m$($C_1$-$C_4$ alkyl), ($C_1$-$C_4$ alkyl)S(=O)$_m$($C_1$-$C_4$ haloalkyl), ($C_1$-$C_4$ alkyl)C(=O)N(R$^x$R$^y$), and C(=O)R$^{13}$, wherein each alkyl, substituted aryl, substituted phenyl, and substituted pyridyl is optionally substituted with one or more substituents independently selected from the group consisting of F, Cl, CN, OH, $C_1$-$C_4$ haloalkyl, $C_1$-$C_4$ haloalkoxy, and $C_1$-$C_4$ alkoxy, pyrimidyl, or wherein $R^x$ and $R^y$ together form a 6-membered saturated cyclic group that optionally contains an additional nitrogen heteroatom, and wherein said cyclic group may be substituted with one or more substituents independently selected from the group consisting of $C_1$-$C_4$ alkyl, $C_3$-$C_6$ cycloalkyl, and phenyl;

$R^{10}$ and $R^{11}$ are independently selected from the group consisting of H, Cl, $C_1$-$C_4$ alkyl, $C_1$-$C_4$ haloalkyl, $C_1$-$C_4$ alkylphenyl, phenyl, and substituted phenyl, aryl, substituted aryl, wherein each alkyl, haloalkyl, alkylphenyl, substituted aryl, and substituted phenyl is optionally substituted with one or more substituents independently selected from H or $C_1$-$C_4$ haloalkyl;

$R^{13}$ is selected from the group consisting of H, $C_1$-$C_4$ alkyl, $C_2$-$C_4$ alkenyl, $C_1$-$C_4$ haloalkyl, ($C_1$-$C_4$ alkyl)($C_3$-$C_6$ cycloalkyl), $C_1$-$C_4$ alkylphenyl, $C_1$-$C_4$ haloalkylphenyl, phenyl, pyridiyl, pyrimidyl, substituted phenyl, substituted pyridyl, aryl, substituted aryl, ($C_1$-$C_4$ alkyl)C(=O)(phenyl), ($C_1$-$C_4$ alkyl)(haloalkyl)(phenyl), ($C_1$-$C_4$ alkyl)(haloalkyl)(alkyl), ($C_1$-$C_4$ alkyl)C(=O)O($C_1$-$C_4$ alkyl), ($C_1$-$C_4$ alkyl)C(=NOR$^{10}$)R$^{11}$, C(=O)($C_1$-$C_4$ alkyl)S(=O)$_m$($C_1$-$C_4$ alkyl), ($C_1$-$C_4$ alkyl)S(=O)$_m$($C_1$-$C_4$ alkyl), and ($C_1$-$C_4$ alkyl)S(=O)$_m$($C_1$-$C_4$ haloalkyl);

$X^1$ is N or CR$^{12}$, wherein $R^{12}$ is selected from the group consisting of H, F, Cl, Br, I, CN, $NO_2$, OH, $C_1$-$C_4$ alkyl, $C_2$-$C_4$ alkenyl, $C_1$-$C_4$ haloalkyl, $C_1$-$C_4$ alkoxy, $C_1$-$C_4$ haloalkoxy, $C_3$-$C_6$ cycloalkyl, $C_1$-$C_4$ alkylphenyl, aryl, substituted aryl, phenyl, substituted phenyl, heteroaryl, and substituted heteroaryl, and wherein each alkyl, alkenyl, haloalkyl, alkoxy, haloalkoxy, cycloalkyl, alkylphenyl, phenyl, aryl, and heteroaryl is optionally substituted with one or more substituents independently selected from the group consisting of H, F, Cl, Br, I, CN, $NO_2$, OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

Q is O (oxygen), or S (sulfur);

n is 0, 1, or 2; and m is 0, 1, or 2.

In some embodiments, the pesticidal composition may comprise a compound of formula I or any agriculturally acceptable salt thereof, wherein n is 0 and Q is oxygen as shown in the pyrazolo[3,4-c]piperidin-2-one compound of formula I-A below:

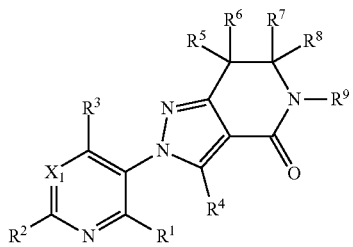

In one embodiment, the pyrazolo[3,4-c]piperidin-2-one compound of formula I-A may be prepared as shown in Scheme 1.

A hydrazine compound 1-1, wherein $R^1$, $R^2$, $R^3$ and $X^1$ are as previously defined and y may be 0, 1, or 2, may be reacted with a piperidine dione compound 1-2, wherein $R^5$, $R^6$, $R^7$, $R^8$, and $R^9$ are as previously defined, in the presence of a base, such as sodium acetate, and a solvent mixture, such as ethanol and water, at about room temperature to give a hydrazine compound 1-3 (A, Scheme 1).

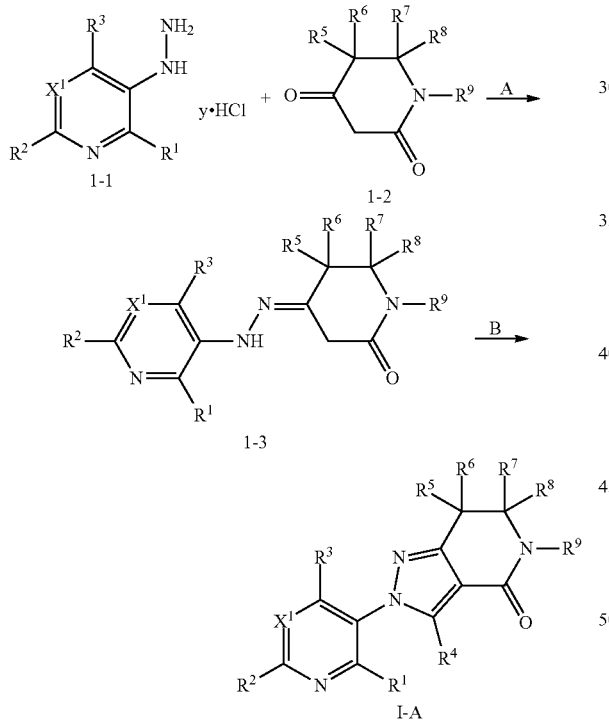

Cyclization of the hydrazine compound 1-3 to a pyrazole [3,4-c]piperidinone compound I-A, wherein $R^4$ is as previously defined, may occur in the presence of a reagent, such as N,N-dimethylformamide-dimethyl acetal ($R^4$=H), neat or in a solvent, such as N,N-dimethylformamide, at temperatures ranging from about 50° C. to about 90° C. (B, Scheme 1).

In a particular embodiment, the pyrazolo[3,4-c]piperidin-2-one compound of formula I-A may be prepared as shown in Scheme 2.

Conversion of the piperidine dione compound 1-2, wherein $R^5$, $R^6$, $R^7$, $R^8$, and $R^9$ are as previously defined, to an intermediate compound 2-1, wherein $R^4$ is as previously defined, may be accomplished in the presence of a reagent, such as N,N-dimethylformamide-dimethyl acetal ($R^4$=H), in a polar aprotic solvent, such as N,N-dimethylformamide, at temperatures ranging from about 50° C. to about 90° C. (A, Scheme 2).

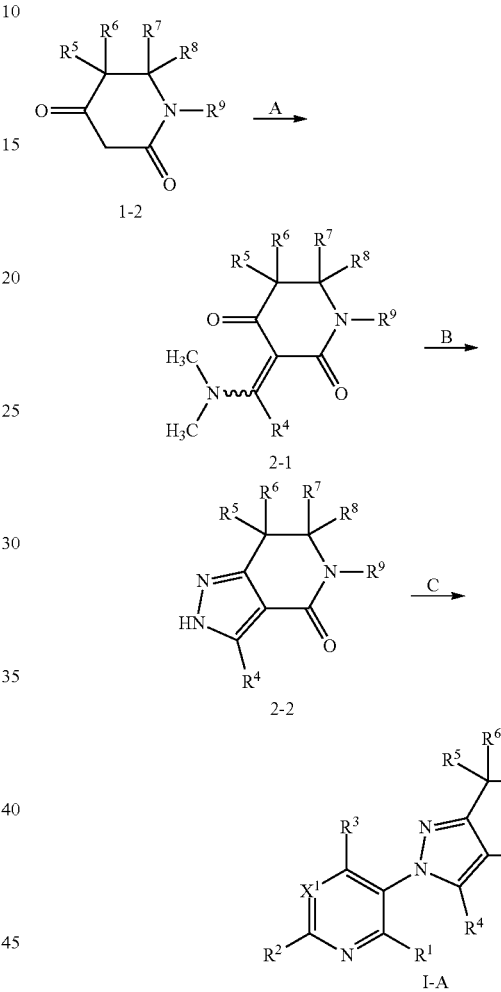

The intermediate compound 2-1 may be reacted with a hydrazine compound, such as hydrazine-hydrate, in a polar protic solvent, such as ethanol, at temperatures ranging from about 50° C. to about reflux to provide a pyrazolo[3,4-c] piperidin-2-one compound 2-2 (B, Scheme 2).

Upon reacting the pyrazolo[3,4-c]piperidin-2-one compound 2-2 with an arylhalide, such as 3-fluoropyridine, in a polar aprotic solvent, such as N,N-dimethylformamide, at temperatures ranging from about 80° C. to about 120° C., the pyrazolo[3,4-c]piperidin-2-one compound I-A may be obtained, wherein $R^1$, $R^2$, $R^3$, and $X^1$ are as previously defined (C, Scheme 2).

In some embodiments, the pesticidal composition may comprise a pyrazolo[3,4-c]piperidin-2-one compound of formula I-A or any agriculturally acceptable salt thereof, wherein $R^1$, $R^2$, $R^3$, $R^4$, $R^5$, $R^6$, $R^7$, $R^8$, $R^9$, and $X^1$ are as previously defined but $R^9$ is not hydrogen (H).

In other embodiments, such pyrazolo[3,4-c]piperidin-2-one compound of formula I-A wherein $R^1$, $R^2$, $R^3$, $R^4$, $R^5$, $R^6$, $R^7$, $R^8$, $R^9$, and $X^1$ are as previously defined but $R^9$ is not H, may be prepared as shown in Scheme 3. The pyrazolo[3,4-c]piperidin-2-one compound 3-2, wherein $R^9$ is as previously defined but not H, may be prepared by alkylating a pyrazolo[3,4-c]piperidin-2-one compound of formula 3-1, wherein $R^1$, $R^2$, $R^3$, $R^4$, $R^5$, $R^6$, $R^7$, $R^8$, and $X^1$ are as previously defined.

In some embodiments, such pyrazolo[3,4-c]piperidin-2-one compound of formula I-A wherein $R^1$, $R^2$, $R^3$, $R^4$, $R^5$, $R^6$, $R^7$, $R^8$, $R^9$, and $X^1$ are as previously defined but $R^9$ is not H, may be prepared as shown in Scheme 4. The pyrazolo[3,4-c]piperidin-2-one compound 3-2, wherein $R^9$ is as previously defined but not H, may be prepared by arylating the pyrazolo[3,4-c]piperidin-2-one compound 3-1.

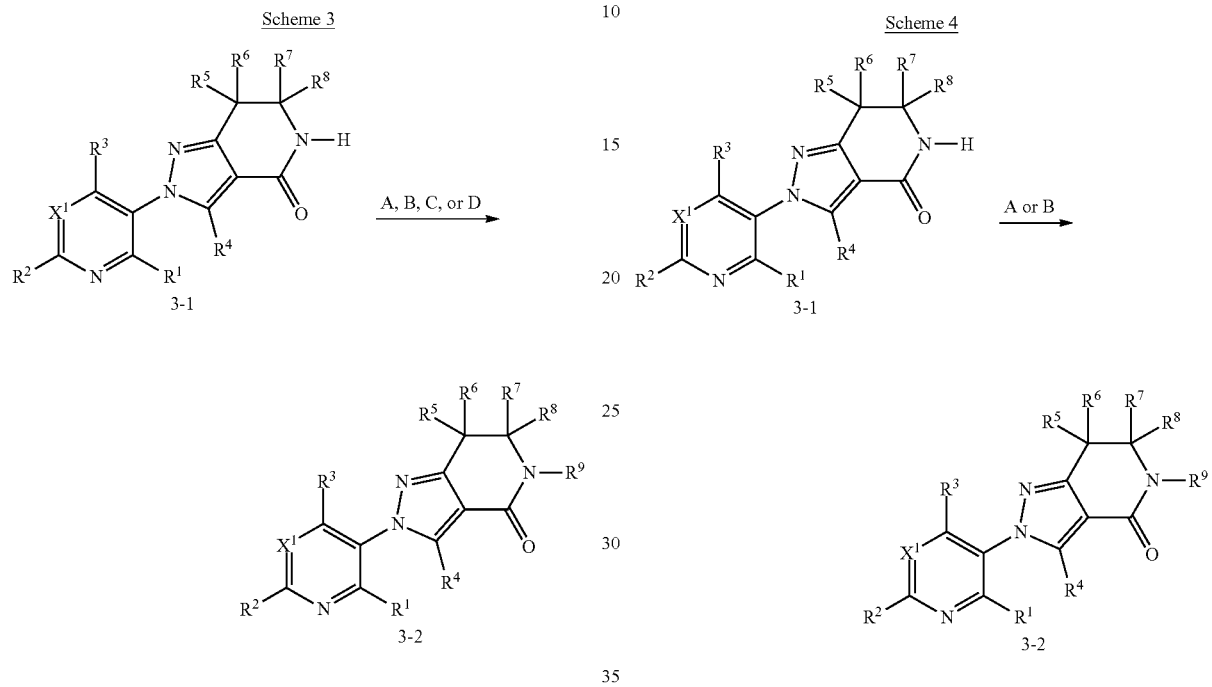

By way of a non-limiting example, the pyrazolo[3,4-c]piperidin-2-one compound 3-1 may be reacted with an alkylhalide, such as iodomethane, in the presence of a base, such as sodium hydride, in a polar aprotic solvent, such as tetrahydrofuran or N,N-dimethylformamide, at temperatures ranging from about 0° C. to about room temperature to provide the pyrazolo[3,4-c]piperidin-2-one compound 3-2 (A, Scheme 3).

By way of another non-limiting example, the pyrazolo[3,4-c]piperidin-2-one compound 3-1 may be reacted with an alkylhalide, such as cyclopropylmethyl bromide, in the presence of a base, such as sodium hydroxide, in a polar aprotic solvent, such as N,N-dimethylformamide, at about room temperature to provide the pyrazolo[3,4-c]piperidin-2-one compound 3-2 (B, Scheme 3).

By way of yet another non-limiting example, the pyrazolo[3,4-c]piperidin-2-one compound 3-1 may be reacted with an alkylhalide, such as 1-(bromomethyl)-4-fluorobenzene, in the presence of a base, such as lithium bis(trimethylsilyl)amide, in a polar aprotic solvent, such as N,N-dimethylformamide, at about room temperature to provide the pyrazolo[3,4-c]piperidin-2-one compound 3-2 (C, Scheme 3).

By way of further non-limiting example, the pyrazolo[3,4-c]piperidin-2-one compound 3-1 may be reacted with an alkylhalide, such as ethyl 2-chloroacetate, in the presence of a base, such as lithium bis(trimethylsilyl)amide, and an additive, such as hexamethylphosphoramide, in a polar aprotic solvent, such as N,N-dimethylformamide, at about room temperature to provide the pyrazolo[3,4-c]piperidin-2-one compound 3-2 (D, Scheme 3).

As a non-limiting example, the pyrazolo[3,4-c]piperidin-2-one compound 3-1 may be reacted with an arylhalide, such as 2-bromopyridine, in the presence of a catalyst, such as copper(I) iodide, a ligand, such as trans-1,2-diaminocyclohexane, and a base, such as cesium carbonate, in a polar aprotic solvent, such as 1,4-dioxane, at a temperature ranging from about 70° C. to about reflux to provide the pyrazolo[3,4-c]piperidin-2-one compound 3-2 (A, Scheme 4).

As another non-limiting example, the pyrazolo[3,4-c]piperidin-2-one compound 3-1 may be reacted with an arylhalide, such as 2-bromo-5-(trifluoromethyl)pyridine, in the presence of a catalyst, such as tris(dibenzylideneacetone)dipalladium(0), a ligand, such as 4,5-bis(diphenylphosphino)-9,9-dimethylxanthene, and a base, such as cesium carbonate, in a polar aprotic solvent, such as 1,4-dioxane, at a temperature ranging from about 70° C. to about reflux to provide the pyrazolo[3,4-c]piperidin-2-one compound 3-2 (B, Scheme 4).

In particular embodiments, the pesticidal composition may comprise a pyrazolo[3,4-c]piperidin-2-one compound of formula I-A or any agriculturally acceptable salt thereof, wherein $R^9$ is C(=O)$R^{13}$, and $R^1$, $R^2$, $R^3$, $R^4$, $R^5$, $R^6$, $R^7$, $R^8$, $R^{13}$ and $X^1$ are as previously defined.

In one embodiment, such pyrazolo[3,4-c]piperidin-2-one compound I-A, wherein $R^9$ is C(=O)$R^{13}$ and $R^{13}$ is ($C_1$-$C_4$ alkyl)S(=O)$_m$($C_1$-$C_4$ alkyl), may be prepared as shown in Scheme 5.

Scheme 5

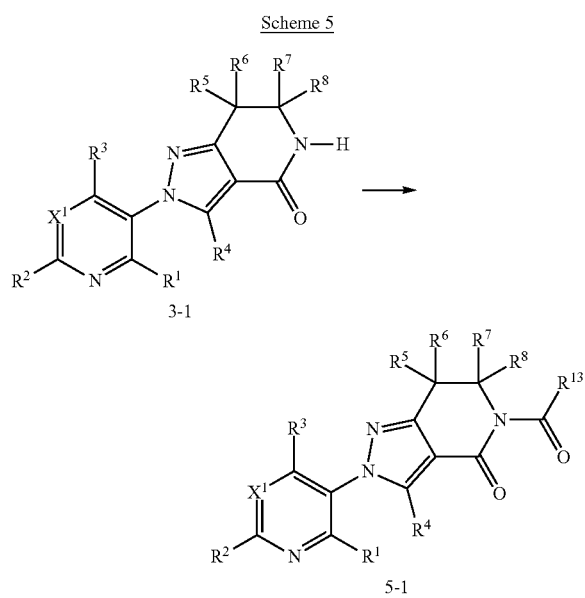

As shown in Scheme 5, the pyrazolo[3,4-c]piperidin-2-one compound 3-1, wherein $R^1$, $R^2$, $R^3$, $R^4$, $R^5$, $R^6$, $R^7$, $R^8$, and $X^1$ are as previously defined, may be acylated with an acylating agent, such as 3-(methylthio)propanoyl chloride, in the presence of a base, such as N-ethyl-N-isopropylpropan-2-amine, in a polar aprotic solvent, such as 1,2-dichloroethane, under microwave heating at temperatures ranging from about 80° C. to about 120° C. to provide a pyrazolo[3,4-c]piperidin-2-one compound 5-1, wherein $R^{13}$ is ($C_1$-$C_4$ alkyl)S(=O)$_m$($C_1$-$C_4$ alkyl).

In some embodiments, the pesticidal composition may comprise a pyrazolo[3,4-c]piperidin-2-one compound of formula I-A or any agriculturally acceptable salt thereof, wherein $R^9$ is ($C_1$-$C_4$ alkyl)S(=O)$_m$($C_1$-$C_4$ alkyl) or ($C_1$-$C_4$ alkyl)S(=O)$_m$($C_1$-$C_4$ haloalkyl) when m is 0, and $R^1$, $R^2$, $R^3$, $R^4$, $R^5$, $R^6$, $R^7$, $R^8$ and $X^1$ are as previously defined.

In another embodiment, such pyrazolo[3,4-c]piperidin-2-one compound I-A, wherein $R^9$ is ($C_1$-$C_4$ alkyl)S(=O)$_m$($C_1$-$C_4$ alkyl) or ($C_1$-$C_4$ alkyl)S(=O)$_m$($C_1$-$C_4$ haloalkyl) when m is 0, may be prepared as shown in Scheme 6.

Scheme 6

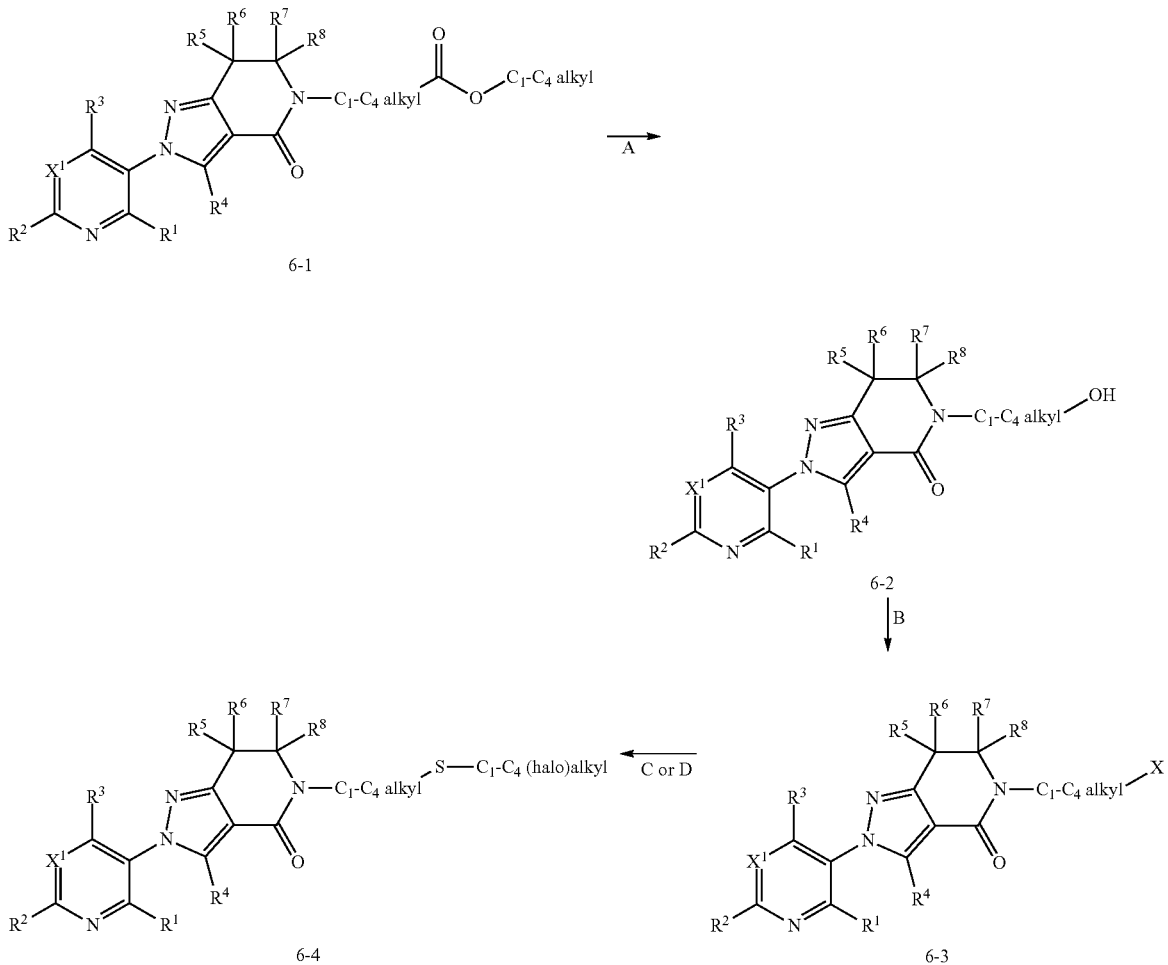

Reduction of a pyrazolo[3,4-c]piperidin-2-one ester compound 6-1, wherein $R^1$, $R^2$, $R^3$, $R^4$, $R^5$, $R^6$, $R^7$, $R^8$, and $X^1$ are as previously defined, by a reducing agent, such as sodium borohydride, in a polar protic solvent, such as ethanol, at about room temperature may provide a pyrazolo[3,4-c]piperidin-2-one alcohol compound 6-2 (A, Scheme 6).

The pyrazolo[3,4-c]piperidin-2-one alcohol compound 6-2 may then be converted to a corresponding pyrazolo[3,4-c]piperidin-2-one halide compound 6-3 by reacting with a halogenating agent, such as 4-toluenesulfonyl chloride, in the presence of a base, such as triethylamine, and a catalyst, such as 4-dimethylaminopyridine, in a solvent, such as dichloromethane, at a temperature of about room temperature (B, Scheme 6). It is understood that other halogenating reagents known in the art, such as thionyl chloride or phosphorus tribromide, may also be used for this purpose.

Then, the pyrazolo[3,4-c]piperidin-2-one halide compound 6-3 may be reacted with a thiol or halothiol compound, such as propane-1-thiol or 3,3,3-trifluoropropane-1-thiol, in the presence of a base, such as cesium carbonate or sodium methoxide, in a polar solvent, such as acetonitrile or N,N-dimethylformamide, at a temperature of about room temperature to about 100° C. to provide a pyrazolo[3,4-c]piperidin-2-one sulfide compound 6-4 (C, Scheme 6).

Alternatively, the pyrazolo[3,4-c]piperidin-2-one halide compound 6-3 may be converted to the pyrazolo[3,4-c]piperidin-2-one sulfide compound 6-4 by reacting with a thiolate agent, such as sodium thiomethoxide, in a solvent such as acetonitrile, at a temperature of about room temperature (D, Scheme 6).

In some embodiments, the pyrazolo[3,4-c]piperidin-2-one halide compound 6-3 may be prepared as shown in Scheme 7.

In one embodiment, alkylation of the pyrazolo[3,4-c]piperidin-2-one compound 3-1, wherein $R^1$, $R^2$, $R^3$, $R^4$, $R^5$, $R^6$, $R^7$, $R^8$, and $X^1$ are as previously defined, to provide the pyrazolo[3,4-c]piperidin-2-one compound 6-2 may be accomplished in the presence of aqueous formaldehyde, at about room temperature (A, Scheme 7). Then, the pyrazolo[3,4-c]piperidin-2-one compound 6-2 may be reacted with a halogenating agent, such as thionyl chloride, in the presence of a solvent, such as N,N-dimethylformamide, at a temperature from about 0° C. to about room temperature to provide the pyrazolo[3,4-c]piperidin-2-one halide compound 6-3 (B, Scheme 7). It is understood that other halogenating reagents known in the art, such as phosphorus tribromide, may also be used for this purpose.

Alternatively, in another embodiment, the pyrazolo[3,4-c]piperidin-2-one halide compound 6-3 may be obtained directly by reacting the pyrazolo[3,4-c]piperidin-2-one compound 3-1 with paraformaldehyde in a neat halogenating reagent, such as chlorotrimethylsilane, at temperatures from about room temperature to about 80° C. (C, Scheme 7).

In one embodiment, the pyrazolo[3,4-c]piperidin-2-one compound I-A, wherein $R^9$ is $(C_1-C_4 \text{ alkyl})S(=O)_m(C_1-C_4 \text{ alkyl})$ or $(C_1-C_4 \text{ alkyl})S(=O)_m(C_1-C_4 \text{ haloalkyl})$ when m is 0, may be prepared as shown in Scheme 8A.

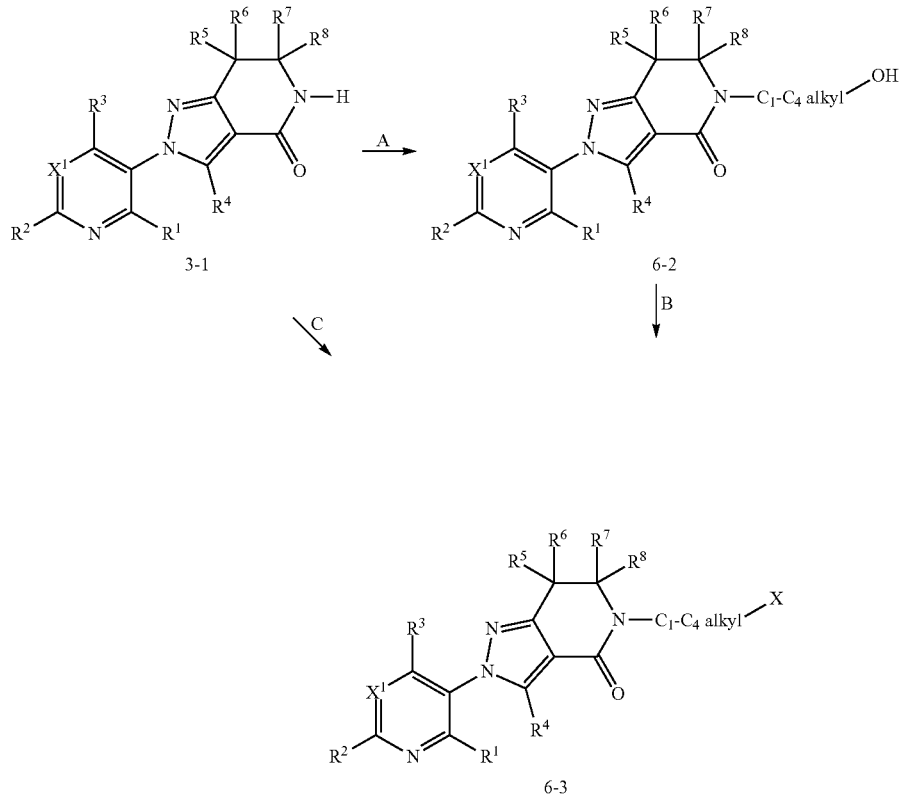

Scheme 7

Scheme 8A

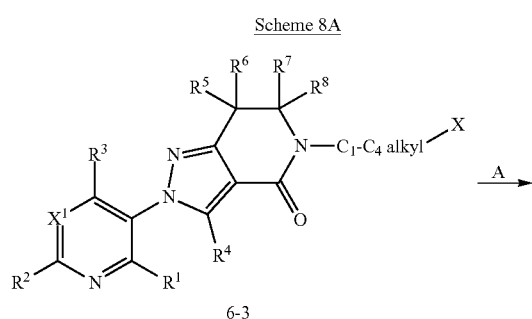

6-3

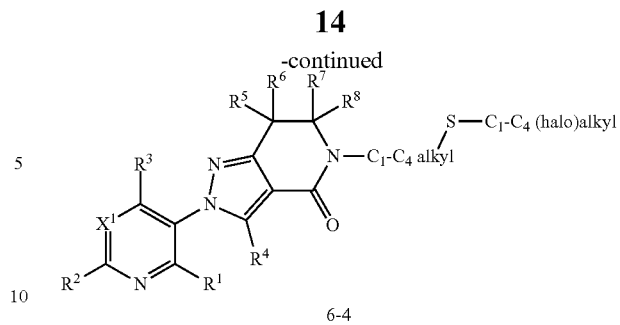

6-4

Thiolation of the pyrazolo[3,4-c]piperidin-2-one halide compound 6-3, wherein $R^1$, $R^2$, $R^3$, $R^4$, $R^5$, $R^6$, $R^7$, $R^8$, and $X^1$ are as previously defined, may be accomplished by treating the pyrazolo[3,4-c]piperidin-2-one halide compound 6-3 with a thioacetic acid to provide a pyrazolo[3,4-c]piperidin-2-one thioester compound 8-1 (A, Scheme 8A).

The removal of an acyl group to deprotect the thiol group on the pyrazolo[3,4-c]piperidin-2-one thioester compound 8-1 followed by direct alkylation of the resulting pyrazolo[3,4-c]piperidin-2-one thiol may be achieved by treating the compound 8-1 with a base, such as potassium carbonate or sodium hydroxide, in a solvent, such as methanol, at a temperature from about 0° C. to about 65° C. Then reacting the resulting thiol compound with an alkylating reagent, such as a ($C_1$-$C_4$ alkyl)halide, ($C_1$-$C_4$ alkyl)triflate, or ($C_1$-$C_4$ haloalkyl)triflate, to provide the pyrazolo[3,4-c]piperidin-2-one sulfide compound 6-4 (B, Scheme 8A).

In one embodiment, the pyrazolo[3,4-c]piperidin-2-one compound I-A, wherein $R^9$ is ($C_1$-$C_4$ alkyl)S(=O)$_m$($C_1$-$C_4$ alkyl) or ($C_1$-$C_4$ alkyl)S(=O)$_m$($C_1$-$C_4$ haloalkyl) when m is 0, may be prepared as shown in Scheme 8B.

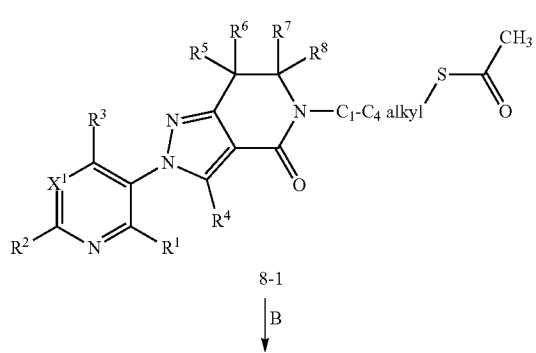

8-1

Scheme 8B

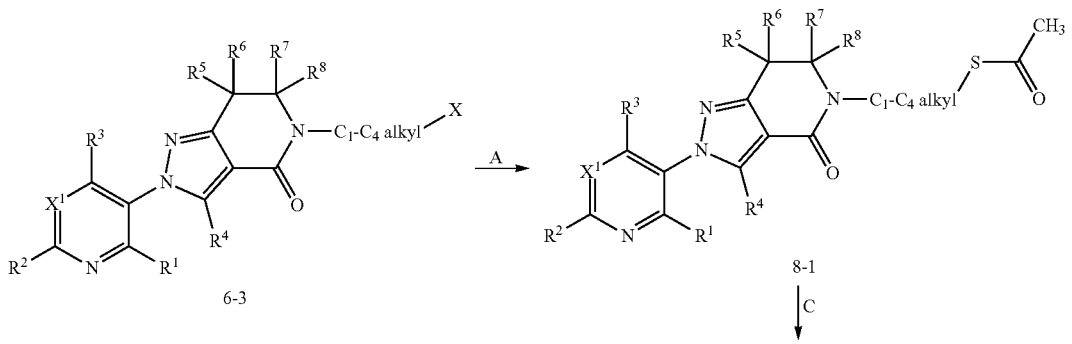

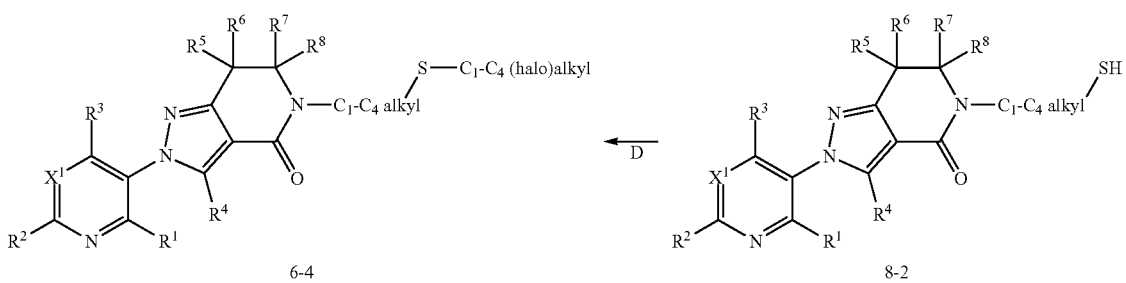

The pyrazolo[3,4-c]piperidin-2-one halide compound 6-3 may be reacted with a thioacetic acid to provide the pyrazolo[3,4-c]piperidin-2-one thioester compound 8-1 (A, Scheme 8B).

The pyrazolo[3,4-c]piperidin-2-one thioester compound 8-1 may then be treated with an amine base, such as pyrrolidine, to deprotect the thiol group and provide the pyrazolo[3,4-c]piperidin-2-one thiol compound 8-2 (C, Scheme 8B).

Then, the pyrazolo[3,4-c]piperidin-2-one thiol compound 8-2 may be reacted with an alkylating reagent, such as a ($C_1$-$C_4$ alkyl)halide, ($C_1$-$C_4$ alkyl)triflate, or ($C_1$-$C_4$ haloalkyl)triflate, in the presence of an amine base, such as triethylamine, in a polar aprotic solvent, such as N,N-dimethylformamide, at temperatures from about 0° C. to about 40° C. to provide the pyrazolo[3,4-c]piperidin-2-one sulfide compound 6-4 (C, Scheme 8B). Alkylating reagents, such as ($C_1$-$C_4$ alkyl)triflate or ($C_1$-$C_4$ haloalkyl)triflate, may be prepared according to procedures outlined in Tetrahedron Lett. 2010, 51, 6542.

In some embodiments, the pesticidal composition may comprise a pyrazolo[3,4-c]piperidin-2-one compound of formula I-A or any agriculturally acceptable salt thereof, wherein $R^9$ is ($C_1$-$C_4$ alkyl)S(=O)$_m$($C_1$-$C_4$ alkyl) or ($C_1$-$C_4$ alkyl)S(=O)$_m$($C_1$-$C_4$ haloalkyl) when m is 1 or 2, and $R^1$, $R^2$, $R^3$, $R^4$, $R^5$, $R^6$, $R^7$, $R^8$ and $X^1$ are as previously defined.

In another embodiment, such pyrazolo[3,4-c]piperidin-2-one compound I-A, wherein $R^9$ is ($C_1$-$C_4$ alkyl)S(=O)$_m$($C_1$-$C_4$ alkyl) or ($C_1$-$C_4$ alkyl)S(=O)$_m$($C_1$-$C_4$ haloalkyl) when m is 1 or 2, may be prepared as shown in Scheme 9.

Scheme 9

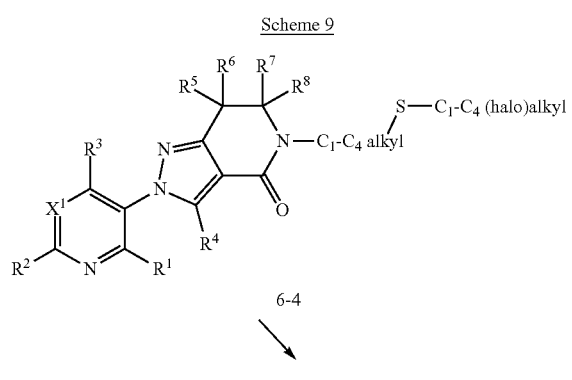

6-4

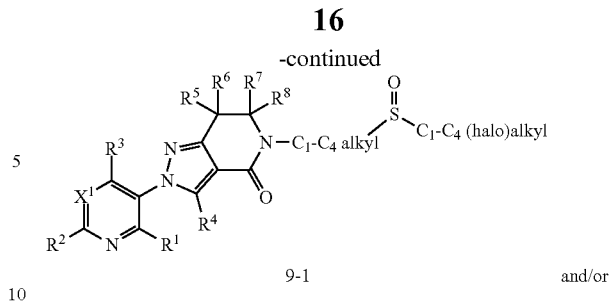

9-1 and/or

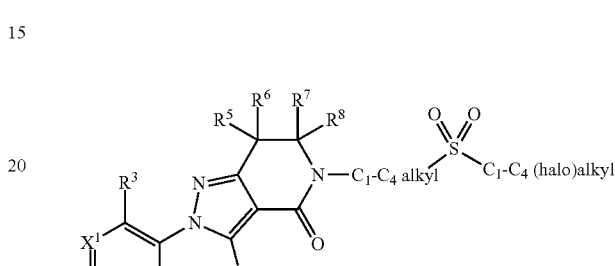

9-2

As shown in Scheme 9, the pyrazolo[3,4-c]piperidin-2-one sulfide compound 6-4, wherein $R^1$, $R^2$, $R^3$, $R^4$, $R^5$, $R^6$, $R^7$, $R^8$, and $X^1$ are as previously defined, may be oxidized by an oxidant, such as sodium perborate tetrahydrate, in a polar protic solvent, such as acetic acid, at a temperature ranging from about 40° C. to about 70° C. to provide the corresponding pyrazolo[3,4-c]piperidin-2-one sulfoxide compound 9-1 and/or the corresponding pyrazolo[3,4-c]piperidin-2-one sulfone compound 9-2.

In some embodiments, the pesticidal composition may comprise a pyrazolo[3,4-c]piperidin-2-one compound of formula I-A or any agriculturally acceptable salt thereof, wherein $R^9$ is $C_1$-$C_4$ haloalkyl, and $R^1$, $R^2$, $R^3$, $R^4$, $R^5$, $R^6$, $R^7$, R and $X^1$ are as previously defined.

In one embodiment, such pyrazolo[3,4-c]piperidin-2-one compound I-A, wherein $R^9$ is $C_1$-$C_4$ haloalkyl, may be prepared as shown in Scheme 10.

Scheme 10

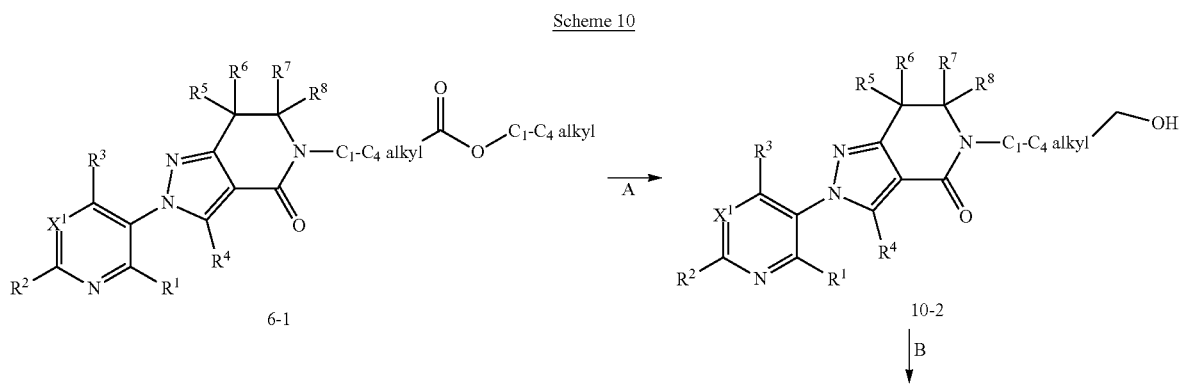

-continued

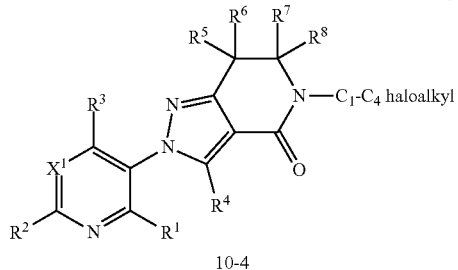

10-4

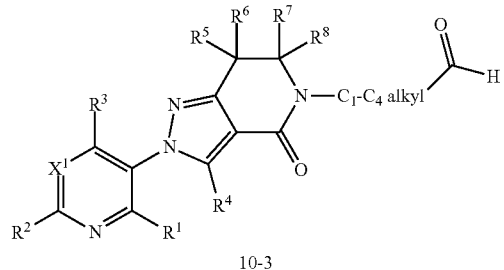

10-3

The pyrazolo[3,4-c]piperidin-2-one ester compound 6-1, wherein $R^1$, $R^2$, $R^3$, $R^4$, $R^5$, $R^6$, $R^7$, $R^8$, and $X^1$ are as previously defined, may be reduced by a reducing agent, such as sodium borohydride, in a polar protic solvent, such as ethanol, at about room temperature to provide the corresponding pyrazolo[3,4-c]piperidin-2-one alcohol compound 10-2 (A, Scheme 10).

The pyrazolo[3,4-c]piperidin-2-one alcohol compound 10-2 may then be oxidized by an oxidant, such as Dess-Martin periodinane, to afford the corresponding pyrazolo[3,4-c]piperidin-2-one aldehyde compound 10-3 (B, Scheme 10).

Subsequently, the pyrazolo[3,4-c]piperidin-2-one aldehyde compound 10-3 may be reacted with a fluorinating reagent, such as diethylaminosulfur trifluoride, in a solvent, such as dichloromethane, at temperatures from about 0° C. to about 40° C. to provide a pyrazolo[3,4-c]piperidin-2-one compound 10-4 (C, Scheme 10).

Alternatively, the pyrazolo[3,4-c]piperidin-2-one aldehyde compound 10-3 may be converted to the pyrazolo[3,4-c]piperidin-2-one compound 10-4 by treating with a metallated alkyl reagent, such as an alkyl Grignard reagent, such as methylmagnesium bromide, in a solvent, such as tetrahydrofuran, at temperatures from about −78° C. to about room temperature, followed by oxidizing and fluorinating as described above to provide the pyrazolo[3,4-c]piperidin-2-one compound 10-4 (D, Scheme 10).

Furthermore, alternatively, the pyrazolo[3,4-c]piperidin-2-one aldehyde compound 10-3 may be treated with Ruppert's reagent (trifluoromethyltrimethylsilane), followed by oxidation and fluorination as described above to provide the pyrazolo[3,4-c]piperidin-2-one compound 10-4 (E, Scheme 10).

In one embodiment, the pyrazolo[3,4-c]piperidin-2-one compound I-A, wherein $R^9$ is $(C_1-C_4$ alkyl$)C(=O)$(phenyl), and $R^1$, $R^2$, $R^1$, $R^4$, $R^5$, $R^6$, $R^7$, $R^8$ and $X^1$ are as previously defined, may be prepared as shown in Scheme 11A.

The pyrazolo[3,4-c]piperidin-2-one ester compound 6-1, wherein $R^1$, $R^2$, $R^3$, $R^4$, $R^5$, $R^6$, $R^7$, $R^8$, and $X^1$ are as previously defined, may be converted to the corresponding pyrazolo[3,4-c]piperidin-2-one N-methoxy-N-methylamide (hereinafter "pyrazolo[3,4-c]piperidin-2-one Weinreb amide") compound 11-1 by treating with a base, such as lithium hydroxide, in a solvent mixture, such as tetrahydrofuran and water, at about room temperature (A, Scheme 11A).

Scheme 11A

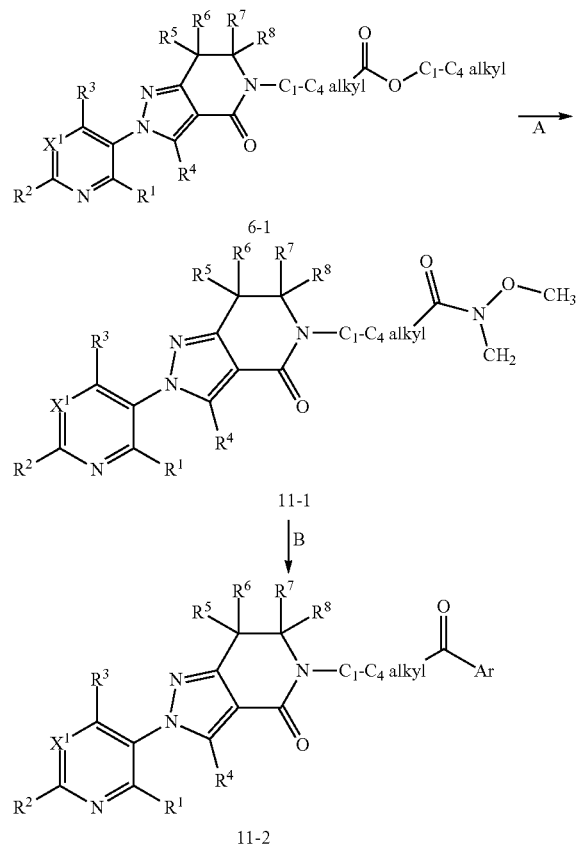

Then, the pyrazolo[3,4-c]piperidin-2-one Weinreb amide compound 11-1 may be reacted with a metallated aryl species, such as an aryl Grignard reagent, such as phenylmagnesium bromide, in a solvent, such as tetrahydrofuran, at temperatures from about −78° C. to about room temperature to provide a pyrazolo[3,4-c]piperidin-2-one compound 11-2 (B, Scheme 11A). Ar group is an aromatic group with or without any substitution, and may or may not include one or more heteroatoms.

In one embodiment, the pyrazolo[3,4-c]piperidin-2-one compound I-A, wherein $R^9$ is $(C_1-C_4$ alkyl)(haloalkyl)(phenyl), and $R^1$, $R^2$, $R^3$, $R^4$, $R^5$, $R^6$, $R^7$, R and $X^1$ are as previously defined, may be prepared as shown in Scheme 11B.

The pyrazolo[3,4-c]piperidin-2-one compound 11-2 may be converted to the pyrazolo[3,4-c]piperidin-2-one compound 11-3 by treating the pyrazolo[3,4-c]piperidin-2-one compound 11-2 with a halogenating agent.

By way of non-limiting example, the pyrazolo[3,4-c]piperidin-2-one compound 11-2 may be treated with a fluorinating agent, such as diethylaminosulfur trifluoride, in a solvent, such as dichloromethane, at temperatures from about 0° C. to about 40° C. to provide the pyrazolo[3,4-c]piperidin-2-one compound 11-3.

Scheme 11B

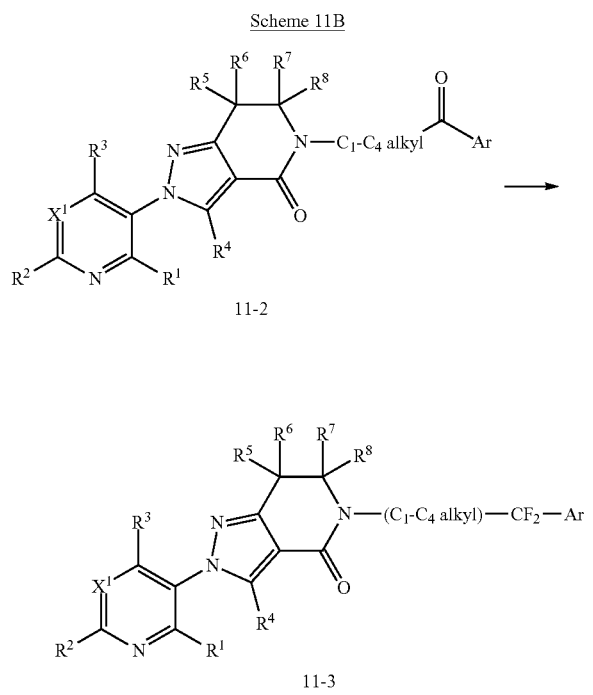

11-2

11-3

By way of non-limiting example, the pyrazolo[3,4-c]piperidin-2-one compound 11-2 may be treated with a fluorinating agent, such as diethylaminosulfur trifluoride, in a solvent, such as dichloromethane, at temperatures from about 0° C. to about 40° C. to provide the pyrazolo[3,4-c]piperidin-2-one compound 11-3.

In one embodiment, the pyrazolo[3,4-c]piperidin-2-one compound I-A, wherein $R^9$ is $(C_1$-$C_4$ alkyl)(haloalkylX-alkyl), and $R^1$, $R^2$, $R^3$, $R^4$, $R^5$, $R^6$, $R^7$, $R^8$ and $X^1$ are as previously defined, may be prepared as shown in Scheme 11C.

The pyrazolo[3,4-c]piperidin-2-one Weinreb amide compound 11-1, wherein $R^1$, $R^2$, $R^3$, $R^4$, $R^5$, $R^6$, $R^7$, $R^8$, and $X^1$ are as previously defined, may be treated with a metallated alkyl reagent, such as an alkyl Grignard reagent, such as methylmagnesium bromide, in a solvent, such as tetrahydrofuran, at temperatures from about −78° C. to about room temperature to provide a pyrazolo[3,4-c]piperidin-2-one ketone compound 11-4 (A, Scheme 11C).

Then, the pyrazolo[3,4-c]piperidin-2-one ketone compound 11-4 may be converted to the pyrazolo[3,4-c]piperidin-2-one compound 11-5 by treating with a halogenating agent, as described above in Scheme 11B. By way of non-limiting example, the pyrazolo[3,4-c]piperidin-2-one compound 11-4 may be treated with a fluorinating agent, such as diethylaminosulfur trifluoride, in a solvent, such as dichloromethane, at temperatures from about 0° C. to about 40° C. to provide the pyrazolo[3,4-c]piperidin-2-one compound 11-5 (B, Scheme 11C).

Scheme 11C

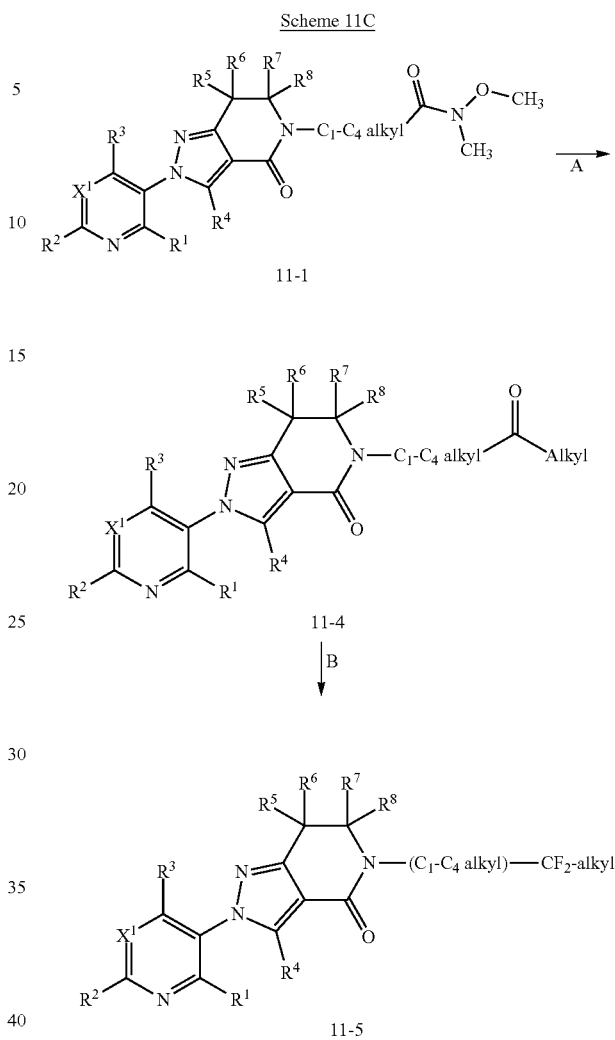

11-1

11-4

11-5

In some embodiments, the pesticidal composition may comprise a pyrazolo[3,4-c]piperidin-2-one compound of formula I-A or any agriculturally acceptable salt thereof, wherein $R^9$ is $(C_1$-$C_4$ alkyl)C($=$NOR$^{10}$)R$^{11}$, R$^{11}$ is H, and $R^1$, $R^2$, $R^3$, $R^4$, $R^5$, $R^6$, $R^7$, $R^8$, $R^{10}$ and $X^1$ are as previously defined.

In another embodiment, such pyrazolo[3,4-c]piperidin-2-one compound I-A, wherein $R^9$ is $(C_1$-$C_4$ alkyl)CH($=$NOR$^{10}$), may be prepared as shown in Scheme 12A.

Scheme 12A

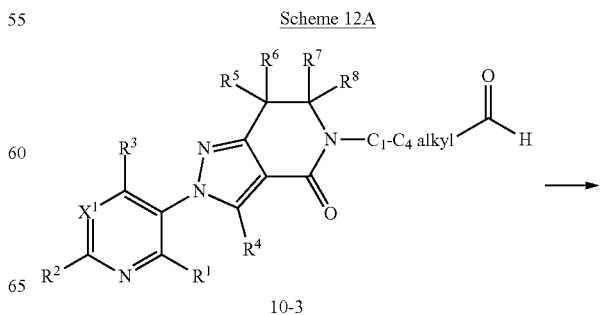

10-3

-continued

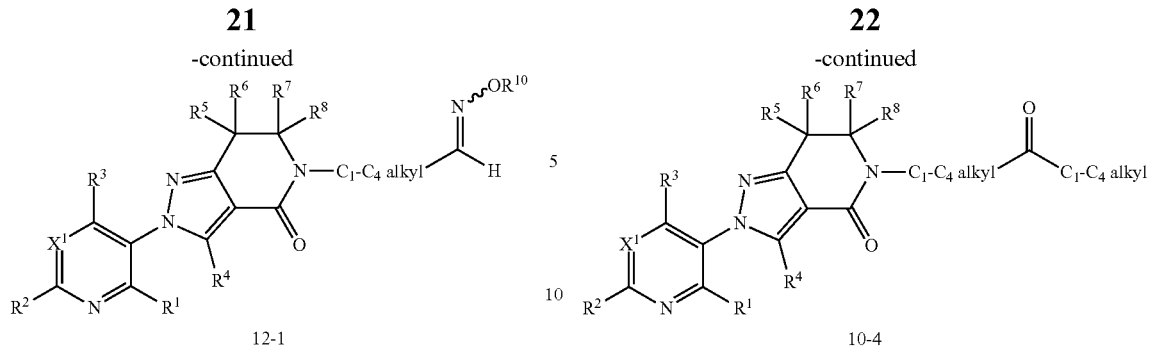

12-1

As shown in Scheme 12A, the pyrazolo[3,4-c]piperidin-2-one aldehyde compound 10-3, wherein $R^1$, $R^2$, $R^3$, $R^4$, $R^5$, $R^6$, $R^7$, $R^8$ and $X^1$ are as previously defined, may be reacted with a hydroxylamine compound $H_2NOR^{10}$, wherein $R^{10}$ is as previously defined, in a polar protic solvent, such as ethanol, with or without an acid, such as acetic acid, to provide the corresponding pyrazolo[3,4-c]piperidin-2-one oxime compound 12-1.

In some embodiments, the pesticidal composition may comprise a pyrazolo[3,4-c]piperidin-2-one compound of formula I-A or any agriculturally acceptable salt thereof, wherein $R^9$ is $(C_1-C_4$ alkyl$)C(=NOR^{10})R^{11}$, $R^{11}$ is $C_1-C_4$ alkyl, and $R^1$, $R^2$, $R^3$, $R^4$, $R^5$, $R^6$, $R^7$, $R^8$, $R^{10}$ and $X^1$ are as previously defined.

In one embodiment, such pyrazolo[3,4-c]piperidin-2-one compound I-A, wherein $R^9$ is $(C_1-C_4$ alkyl$)C(=NOR^{10})(C_1-C_4$ alkyl$)$, may be prepared as shown in Scheme 12B.

The pyrazolo[3,4-c]piperidin-2-one aldehyde compound 10-3 may be reacted with a metallated alkyl reagent, such as an alkyl Grignard reagent, such as methylmagnesium bromide, in a solvent such as tetrahydrofuran, at temperatures from about −78° C. to about room temperature. Then, the resulting pyrazolo[3,4-c]piperidin-2-one compound may be treated with an oxidant, such as Dess-Martin periodinane, to provide the pyrazolo[3,4-c]piperidin-2-one ketone compound 10-4 (A, Scheme 12B).

The pyrazolo[3,4-c]piperidin-2-one ketone compound 10-4 may then be reacted with a hydroxylamine compound $H_2NOR^{1'}$, wherein $R^{10}$ is as previously defined, in a polar protic solvent, such as ethanol, with or without an acid, such as acetic acid, to provide the corresponding pyrazolo[3,4-c]piperidin-2-one keto-oxime compound 12-2 (B, Scheme 12B).

-continued

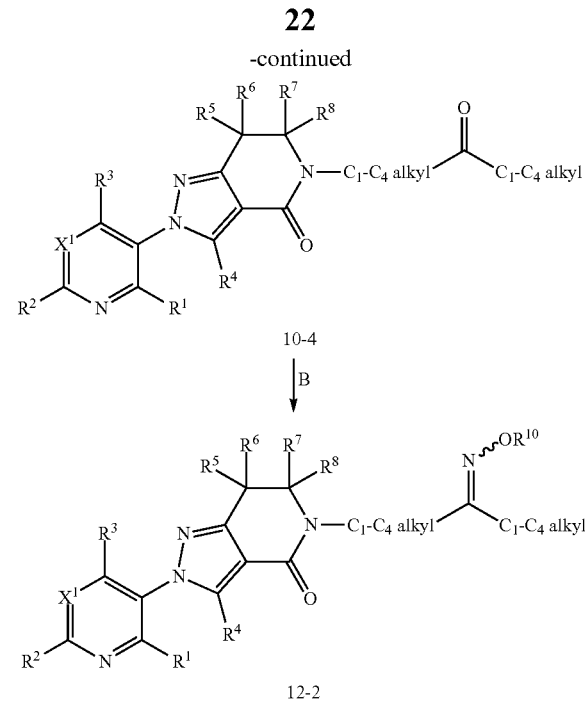

In some embodiments, the pesticidal composition may comprise a pyrazolo[3,4-c]piperidin-2-one compound of formula I-A or any agriculturally acceptable salt thereof, wherein $R^9$ is $(C_1-C_4$ alkyl$)C(=NOR^{11})R^{11}$, $R^{11}$ is $C_1-C_4$ haloalkyl, and $R^1$, $R^2$, $R^3$, $R^4$, $R^5$, $R^6$, $R^7$, $R^8$, $R^{10}$ and $X^1$ are as previously defined.

In another embodiment, such pyrazolo[3,4-c]piperidin-2-one compound I-A, wherein $R^9$ is $R^9$ is $(C_1-C_4$ alkyl$)C(=NOR^{10})(C_1-C_4$ haloalkyl$)$, may be prepared as shown in Scheme 12C.

The pyrazolo[3,4-c]piperidin-2-one aldehyde compound 10-3 may be reacted with a trifluoromethylating agent, such as Ruppert's reagent (i.e., trifluoromethyltrimethyl silane), followed by oxidation, as described above, to provide a pyrazolo[3,4-c]piperidin-2-one ketone compound 10-5 (A, Scheme 12C).

Subsequently, the pyrazolo[3,4-c]piperidin-2-one ketone compound 10-5 may be reacted with an hyroxylamine compound $H_2NOR^{10}$, wherein $R^{10}$ is as previously defined, in a polar protic solvent, such as ethanol, with or without an acid, such as acetic acid, to provide the corresponding pyrazolo[3,4-c]piperidin-2-one keto-oxime compound 12-3 (B, Scheme 12C).

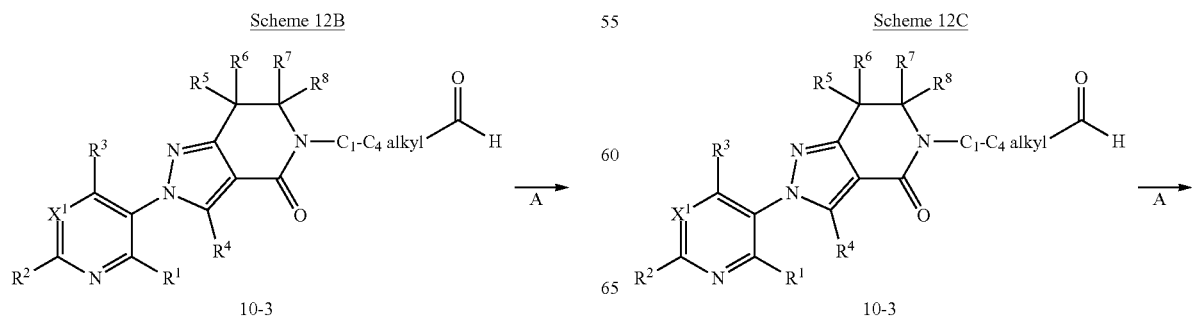

Scheme 12B      Scheme 12C 10-3      10-3

-continued

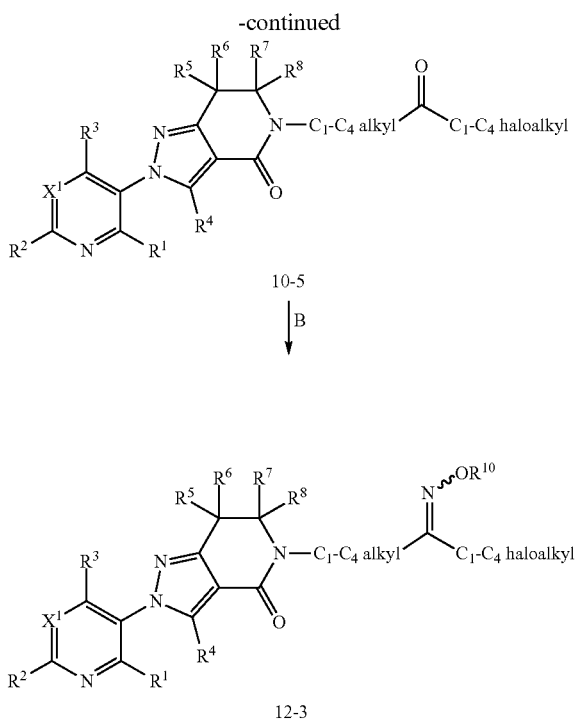

10-5

↓ B

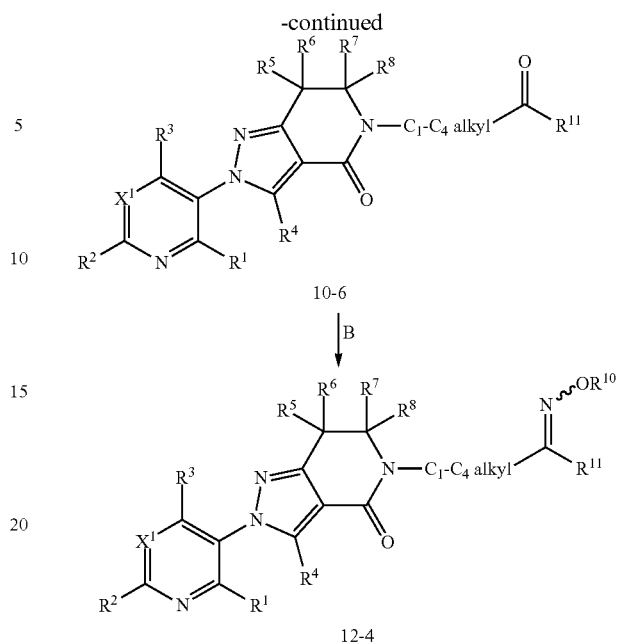

10-6

↓ B 12-3

12-4

In some embodiments, the pesticidal composition may comprise a pyrazolo[3,4-c]piperidin-2-one compound of formula I-A or any agriculturally acceptable salt thereof, wherein $R^9$ is $(C_1$-$C_4$ alkyl)$C(=NOR^{10})R^{11}$, $R^{11}$ is phenyl or substituted phenyl, and $R^1$, $R^2$, $R^3$, $R^4$, $R^5$, $R^6$, $R^7$, $R^8$, $R^{10}$ and $X^1$ are as previously defined.

In one embodiment, such pyrazolo[3,4-c]piperidin-2-one compound I-A, wherein $R^9$ is $(C_1$-$C_4$ alkyl)$C(=NOR^{10})R^{11}$, and $R^{11}$ is phenyl or substituted phenyl, may be prepared as shown in Scheme 12D.

The pyrazolo[3,4-c]piperidin-2-one Weinreb amide compound 11-1, wherein $R^1$, $R^2$, $R^3$, $R^4$, $R^5$, $R^6$, $R^7$, $R^8$, and $X^1$ are as previously defined, may be reacted with a metallated aryl reagent, such as an aryl Grignard reagent, such as phenylmagnesium bromide, in a solvent such as tetrahydrofuran, at temperatures from about −78° C. to about room temperature to provide a pyrazolo[3,4-c]piperidin-2-one ketone compound 10-6, wherein $R^{11}$ is phenyl or substituted phenyl (A, Scheme 12D).

Subsequently, the pyrazolo[3,4-c]piperidin-2-one ketone compound 10-6 may be reacted with an hyroxylamine compound $H_2NOR^{10}$, wherein $R^{1'}$ is as previously defined, in a polar protic solvent, such as ethanol, with or without an acid, such as acetic acid, to provide the corresponding pyrazolo[3,4-c]piperidin-2-one keto-oxime compound 12-4, wherein $R^{11}$ is phenyl or substituted phenyl (B, Scheme 12D).

In some embodiments, the pesticidal composition may comprise a compound of formula I or any agriculturally acceptable salt thereof, wherein n is 0 and Q is sulfur as shown in the pyrazolo[3,4-c]piperidin-2-thione compound of formula I-B below:

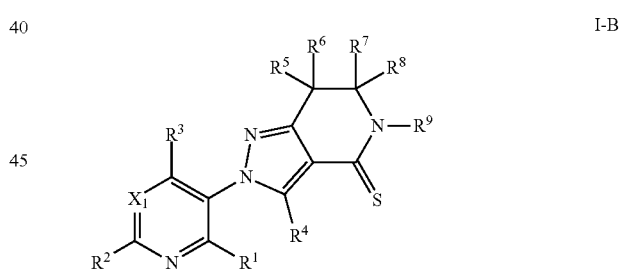

I-B

In a particular embodiment, the pyrazolo[3,4-c]piperidin-2-thione compound of formula I—B may be prepared as shown in Scheme 13.

Scheme 12D

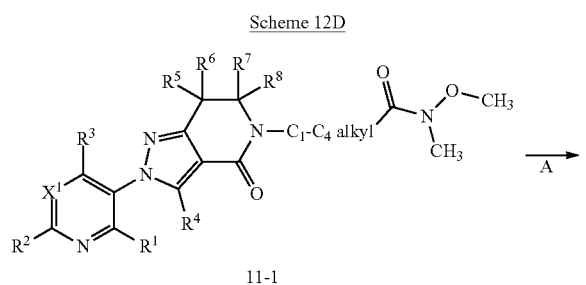

11-1

Scheme 13

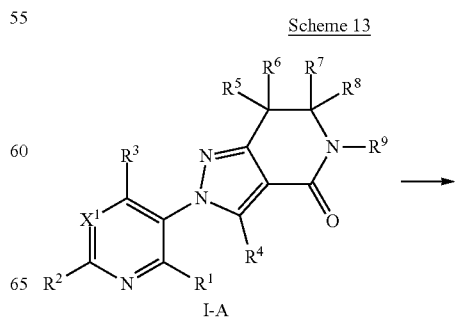

I-A

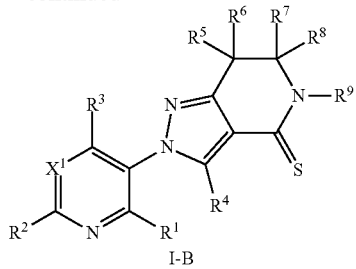

I-B

The pyrazolo[3,4-c]piperidin-2-one compound of the formula I-A, wherein $R^1$, $R^2$, $R^3$, $R^4$, $R^5$, $R^6$, $R^7$, $R^8$, $R^9$, and $X^1$ are as previously defined, may be reacted with a thionation reagent, such as Lawesson's reagent, in an aprotic solvent, such as 1,2-dichloroethane or toluene, under either standard heating conditions or microwave conditions at temperatures ranging from about 80° C. to about 140° C. to provide the pyrazolo[3,4-c]piperidin-2-thione compound of the formula I-B.

PESTICIDALLY ACCEPTABLE ACID ADDITION SALTS. SALT DERIVATIVES, SOLVATES, ESTER DERIVATIVES, POLYMORPHS, ISOTOPES, RADIONUCLIDES and STEREOISOMERS In some embodiments, the compound of formula I may be formulated into pesticidally acceptable acid addition salts. By way of a non-limiting example, an amine function may form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, hydroxyethanesulfonic, and trifluoroacetic acids. Additionally, by way of a non-limiting example, an acid function may form salts including those derived from alkali or alkaline earth metals and those derived from ammonia and amines. Non-limiting examples of cations may include sodium, potassium, or magnesium.

In other embodiments, the compound of formula I may be formulated into salt derivatives. By way of a non-limiting example, a salt derivative may be prepared by contacting a free base with a sufficient amount of the desired acid to produce a salt. A free base may be regenerated by treating the salt with a suitable dilute aqueous base solution such as, but not limited to, dilute aqueous sodium hydroxide (NaOH), potassium carbonate, ammonia, and sodium bicarbonate.

In further embodiments, the compound of formula I may be formulated into stable complexes with a solvent, such that the complex may remain intact after the non-complexed solvent is removed. These complexes are often referred to as "solvates." It may be desirable to form stable hydrates with water as the solvent.

In some embodiments, the compound of formula I may be made into ester derivatives.

In particular embodiments, the compound of formula I may be made as various crystal polymorphs. Polymorphism is important in the development of agrochemicals, since different crystal polymorphs or structures of the same molecule may have vastly different physical properties and biological performances.

In further embodiments, the compound of formula I may be made with different isotopes. Of particular importance are molecules having $^2H$ (also known as deuterium) in place of $^1H$.

In some embodiments, the compound of formula I may be made with different radionuclides. Of particular importance are molecules having $^{13}C$ or $^{14}C$.

In other embodiments, the compound of formula I may exist as one or more stereoisomers. Thus, certain molecules may be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain compounds disclosed in this patent application may exist as two or more isomers. The various isomers may include geometric isomers, diastereomers, or enantiomers. Thus, the compounds disclosed in this patent application may include geometric isomers, racemic mixtures, individual stereoisomers, or optically active mixtures. It will be appreciated by those skilled in the art that one isomer may be more active than the others. The structures disclosed in the present disclosure may be drawn in only one geometric form for clarity, but are intended to represent all geometric forms of the compound.

Pesticidal Compositions

In one particular embodiment, a pesticidal composition comprises the compound of formula I, or any agriculturally acceptable salt thereof.

In some embodiments, a pesticidal composition comprises the compound of formula I or any agriculturally acceptable salt thereof, and a phytologically-acceptable inert carrier (e.g., solid carrier, or liquid carrier).

In another embodiment, the pesticidal composition may further comprise at least one additive selected from surfactant, a stabilizer, an emetic agent, a disintegrating agent, an antifoaming agent, a wetting agent, a dispersing agent, a binding agent, dyes, or fillers.

In particular embodiments, the pesticidal compositions may be in the form of solid. Non-limiting examples of the solid forms may include power, dust or granular formulations.

In other embodiments, the pesticidal compositions may be in the form of liquid formulation. Examples of the liquid forms may include, but not limited to, dispersion, suspension, emulsion, or solution in appropriate liquid carrier.

In further embodiments, the pesticidal compositions may be in the form of liquid dispersion, wherein the compound of formula I may be dispersed in water or other agriculturally suitable liquid carrier.

In yet further embodiments, the pesticidal compositions may be in the form of solution in an appropriate organic solvent. In one embodiment, the spray oils, which are widely used in agricultural chemistry, may be used as an organic solvent for the pesticidal compositions.

The pesticidal composition may be used in conjunction (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

Furthermore, the pesticidal composition may be used in conjunction (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

Insecticides

Non-limiting examples of insecticides that may be used in combination with the compound of formula I may include 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, α/p/ω-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, zeta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdépalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hyprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, or zolaprofos.

Acaricides

Non-limiting examples of acaricides that may be used in combination with the compound of formula I may include acequinocyl, amidoflumet, arsenous oxide, azobenzene, azocyclotin, benomyl, benoxafos, benzoximate, benzyl benzoate, bifenazate, binapacryl, bromopropylate, chinomethionat, chlorbenside, chlorfenethol, chlorfenson, chlorfensulphide, chlorobenzilate, chloromebuform, chloromethiuron, chloropropylate, clofentezine, cyenopyrafen, cyflumetofen, cyhexatin, dichlofluanid, dicofol, dienochlor, diflovidazin, dinobuton, dinocap, dinocap-4, dinocap-6, dinocton, dinopenton, dinosulfon, dinoterbon, diphenyl sulfone, disulfiram, dofenapyn, etoxazole, fenazaquin, fenbutatin oxide, fenothiocarb, fenpyroximate, fenson, fentrifanil, fluacrypyrim, fluazuron, flubenzimine, fluenetil, flumethrin, fluorbenside, hexythiazox, mesulfen, MNAF, nikkomycins, proclonol, propargite, quintiofos, spirodiclofen, sulfiram, sulfur, tetradifon, tetranactin, tetrasul, or thioquinox.

Nematicides

Non-limiting examples of nematicides that may be used in combination with the compound of formula I may include 1,3-dichloropropene, benclothiaz, dazomet, dazomet-sodium, DBCP, DCIP, diamidafos, fluensulfone, fosthiazate, furfural, imicyafos, isamidofos, isazofos, metam, metam-ammonium, metam-potassium, metam-sodium, phosphocarb, or thionazin.

Fungicides

Non-limiting examples of fungicides that may be used in combination with the compound of formula I may include (3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothal-isopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, or zoxamide.

Herbicides

Non-limiting examples of herbicides that may be used in combination the compound of formula I may include 2,3, 6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorflurazole, chlorflurenol, chlorflurenol-methyl, chloridazon, chlorimuron, chlorimuron-ethyl, chlomitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butometyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, flurochloridone, fluroxypyr, fluroxypyr-butometyl, fluroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloramolamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufenethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, or xylachlor.

Biopesticides

The compound of formula I may also be used in combination (such as in a compositional mixture, or a simultaneous or sequential application) with one or more biopesticides. The term "biopesticide" is used for microbial biological pest control agents that are applied in a similar manner to chemical pesticides. Commonly, these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the Biopesticide Manual) 3rd Edition. British Crop Production Council (BCPC), Farnham, Surrey UK.

Other Active Compounds

The compound of formula I may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;

17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-ethyl-2,2-dichloro-1-methylcyclopropanecarboxamide-2-(2,6-dichloro-α,α,α-trifluoro-p-tolyl)hydrazine.

The compound of formula I may also be used in combination (such as in a compositional mixture, or a simultaneous or sequential application) with one or more compounds in the following groups: algicides, antifeedants, avicides, bactericides, bird repellents, chemosterilants, herbicide safeners, insect attractants, insect repellents, mammal repellents, mating disrupters, molluscicides, plant activators, plant growth regulators, rodenticides, or virucides.

Synergistic Mixtures and Synergists

The compound of formula I may be used in combination with at least one other insecticide to form a synergistic mixture where the mode of action of such compounds compared to the mode of action of the compound of formula I are the same, similar, or different. Examples of modes of action may include, but are not limited to: acetylcholinesterase inhibitor; sodium channel modulator, chitin biosynthesis inhibitor, GABA-gated chloride channel antagonist; GABA and glutamate-gated chloride channel agonist; acetylcholine receptor agonist; MET I inhibitor, Mg-stimulated ATPase inhibitor, nicotinic acetylcholine receptor; Midgut membrane disrupter, oxidative phosphorylation disrupter, or ryanodine receptor (RyRs).

Additionally, the compound of formula I may be used in combination with at least one of fungicides, acaricides, herbicides or nematicides to form a synergistic mixture.

Furthermore, the compound of formula I may be used in combination with other active compounds, such as the compounds under the heading "OTHER ACTIVE COMPOUNDS," algicides, avicides, bactericides, molluscicides, rodenticides, virucides, herbicide safeners, adjuvants, and/or surfactants to form a synergistic mixture. Moreover, the following compounds are known as synergists and may be used in combination with the compound of formula I: piperonyl butoxide, piprotal, propyl isome, sesamex, sesamolin, sulfoxide, and tribufos.

Formulations

A pesticide may not be suitable for application in its pure form. It is usually necessary to add other substances so that the pesticide may be used at the required concentration and in an appropriate form, permitting ease of application, handling, transportation, storage, and maximum pesticide activity. Thus, pesticides may be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, such as xylenes and petroleum fractions, especially the high-boiling naphthalenic and olefinic portions of petroleum, such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates can be selected from conventional anionic and non-ionic surfactants.

Aqueous suspensions typically comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions, the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment includes an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the compound of formula I or any agriculturally acceptable salt thereof are used in a formulation, such formulation may also contain other components. These components may include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pesticidal Activities

The disclosed pesticidal compositions may be used, for example, as nematicides, acaricides, pesticides, insecticides, miticides, and/or molluscicides.

In one particular embodiment, a method of controlling pests comprises applying a pesticidal composition comprising a compound of formula I or any agriculturally acceptable salt thereof near a population of pests.

The compounds of formula I are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which the compound of formula I is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with the compound of formula I when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The compound of formula I may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methyl-cyclopropene (also known as 1-MCP). Furthermore, such molecules may be used during times when pest activity is low, such as before the plants that are growing begin to produce valuable agricultural commodities. Such times include the early planting season when pest pressure is usually low.

The compound of formula I can be applied to the foliar and fruiting portions of plants to control pests. The molecules will either come in direct contact with the pest, or the pest will consume the pesticide when eating leaf, fruit mass, or extracting sap, that contains the pesticide. The compound of formula I can also be applied to the soil, and when applied in this manner, root and stem feeding pests can be controlled. The roots can absorb a molecule taking it up into the foliar portions of the plant to control above ground chewing and sap feeding pests.

Generally, with baits, they are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a compound of formula I.

The compound of formula I can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the compound of formula I may be desirable to control newly emerged larvae.

Systemic movement of pesticides in plants may be utilized to control pests on one portion of the plant by applying (for example by spraying an area) the compound of formula I to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the compound of formula I may further enhance the ability of a plant to better withstand stressful growing conditions. This results in a healthier, more vigorous plant, which can lead to higher yields at harvest time. Generally, about 1 gram of the compound of formula I to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the compound of formula I may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The compound of formula I may be used for controlling endoparasites and ectoparasites in the veterinary medicine sector or in the field of non-human animal keeping. The compound of formula I are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The compound of formula I may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The compound of formula I may be used for controlling parasitic worms, especially of the intestine, in the animals listed above. The compound of formula I may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The compound of formula I may also be used on such new invasive species to control them in such new environment.

The compound of formula I may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

The disclosed pesticidal composition comprising a compound of formula I may be used to control a wide variety of pests.

As a non-limiting example, in one or more embodiments, the method of the present disclosure may be used to control one or more members of *Liriomyza sativae, Caliothrips phaseoli, Paratrioza cockerelli, Spodoptera exigua, Myzus persicae, Nilaparvata lugens*, and *Bemisia tabaci*.

In additional embodiments, the method of the present disclosure may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

In further embodiments, the method of the present disclosure may be used to control members of the Order Coleoptera (beetles) including, but not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhomed beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leafcutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana* (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides.*

In other embodiments, the method of the present disclosure may also be used to control members of the Order Dermaptera (earwigs).

In additional embodiments, the method of the present disclosure may be used to control members of the Order Blattodea (cockroaches) including, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In further embodiments, the method of the present disclosure may be used to control members of the Order Diptera (true flies) including, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In other embodiments, the method of the present disclosure may be used to control members of the Order Hemiptera (true bugs) including, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea,* and *Triatoma* spp. (bloodsucking conenose bugs/kissing bugs).

In additional embodiments, the method of the present disclosure may be used to control members of the Order Homoptera (aphids, scales, whiteflies, leafhoppers) including, but is not limited to, *Acrythosiphon pisum* (pea aphid), *Adelges* spp. (adelgids), *Aleurodes proletella* (cabbage whitefly), *Aleurodicus disperses, Aleurothrixusfloccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mah-*

*anarva frimbiolata*, *Metopolophium dirhodum* (rose grain aphid), *Mictis longicornis*, *Myzus* spp., *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*. In at least some embodiments, the method of the present disclosure may be used to control *Myzus persicae*.

In other embodiments, the method of the present disclosure may be used to control members of the Order Hymenoptera (ants, wasps, and bees) including, but not limited to, *Acromyrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In certain embodiments, the method of the present disclosure may be used to control members of the Order Isoptera (termites) including, but not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incisitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In additional embodiments, the method of the present disclosure may be used to control members of the Order Lepidoptera (moths and butterflies) including, but not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma*, *Bonagota cranaodes*, *Borbo cinnara* (rice leaf folder), *Bucculatrix thurberiella* (cotton leafperforator), *Caloptilia* spp. (leaf miners), *Capua reticulana*, *Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella*, *Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarpa*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and Zeuzera pyrina (leopard moth). In at least some embodiments, the method of the present disclosure may be used to control *Spodoptera exigua*.

The method of the present disclosure may be used to also control members of the Order Mallophaga (chewing lice) including, but not limited to, *Bovicola ovis* (sheep biting louse), *Menacanthus stramineus* (chicken body louse), and *Menopon gallinea* (common hen louse).

In additional embodiments, the method of the present disclosure may be used to control members of the Order Orthoptera (grasshoppers, locusts, and crickets) including, but not limited to, *Anabrus simplex* (Mormon cricket), *Gryllotalpidae* (mole crickets), *Locusta migratoria*, *Melanoplus* spp. (grasshoppers), *Microcentrum retinerve* (angular-winged katydid), *Pterophylla* spp. (kaydids), *chistocerca gregaria*, *Scudderia furcata* (forktailed bush katydid), and *Valanga nigricorni*.

In other embodiments, the method of the present disclosure may be used to control members of the Order Phthiraptera (sucking lice) including, but not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In particular embodiments, the method of the present disclosure may be used to control members of the Order Siphonaptera (fleas) including, but not limited to, *Ctenocephalides canis* (dog flea), *Ctenocephalides felis* (cat flea), and *Pulex irritans* (human flea).

In additional embodiments, the method of the present disclosure may be used to control members of the Order Thysanoptera (thrips) including, but not limited to, *Frankliniella fusca* (tobacco thrips), *Frankliniella occidentalis* (western flower thrips), *Frankliniella shultzei*, *Frankliniella williamsi* (corn thrips), *Heliothrips haemorrhaidalis* (greenhouse thrips), *Riphiphorothrips cruentatus*, *Scirtothrips* spp., *Scirtothrips citri* (citrus thrips), *Scirtothrips dorsalis* (yellow tea thrips), *Taeniothrips rhopalantennalis*, and *Thrips* spp.

The method of the present disclosure may be used to also control members of the Order Thysanura (bristletails) including, but not limited to, *Lepisma* spp. (silverfish) and *Thermobia* spp. (firebrats).

In further embodiments, the method of the present disclosure may be used to control members of the Order Acari (mites and ticks) including, but not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi*, *Aculus pelekassi*, *Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati*, *Oligonychus* spp., *Oligonychus coffee*, *Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae*, *Tetranychus* spp., *Tetranychus urticae* (twospotted spider mite), and *Varroa destructor* (honey bee mite).

In additional embodiments, the method of the present disclosure may be used to control members of the Order Nematoda (nematodes) including, but not limited to, *Aphelenchoides* spp. (foliar nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In at least some embodiments, the method of the present disclosure may be used to control at least one insect in one or more of the following Orders: Lepidoptera, Coleoptera, Homoptera, Hemiptera, Thysanoptera, Blattodea, Isoptera, Orthoptera, Diptera, Hymenoptera, and Siphonaptera, and at least one mite in the Order Acari.

Insecticidal Testing

Insecticidal Activities of Non-Limiting Examples of the Disclosed Compounds Against Green Peach Aphid (*Myzus Persicae*) (GPA) (MYZUPE)

The green peach aphid (*Myzus persicae*) is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. Non-limiting examples of such plants being attacked by GPA pests may include, but not limited to, broccoli, burdock, cabbage, carrot, cauliflower, daikon, eggplant, green beans, lettuce, macadamia, papaya, peppers, sweet potatoes, tomatoes, watercress, and zucchini, among other plants. GPA pests may also attack many ornamental crops, including, but not limited to, such as carnation, chrysanthemum, flowering white cabbage, poinsettia, and roses. GPA has developed resistance to many pesticides.

Bioassay for GPA was prepared as follows: Cabbage seedlings grown in 3-inch pots, with 2-3 small (3-5 cm) true leaves, were used as test substrate. The seedlings were infested with 20-50 GPA (adult and nymph stages) one day prior to chemical application. Four pots with individual seedlings were used for each treatment. The tested compounds (2 mg) were dissolved in 2 mL of acetone/methanol (1:1) solvent to form stock solutions of 1000 ppm tested compound. The stock solutions were diluted five times with an aqueous solution containing 0.025% TWEEN® 20 surfactant, which is polyoxyethylene (20) sorbitan monolaurate, to obtain the solution at 200 ppm tested compound. A hand-held aspirator-type sprayer was used for spraying the solution to both sides of cabbage leaves until runoff. The control plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent control was measured by using Abbott's correction formula (W. S. Abbott, "A Method of Computing the Effectiveness of an Insecticide," *J. Econ. Entomol.* 18 (1925), pp. 265-267) as follows.

Corrected % Control=$100*(X-Y)/X$ where
X=No. of live aphids on solvent check plants and
Y=No. of live aphids on treated plants The results are indicated in TABLE 2: Biological Data for Green Peach Aphid (GPA) (MYZUPE) and Sweetpotato Whitefly-crawler (WF) (BEMITA)."

Insecticidal Activities of Non-Limiting Examples of the Disclosed Compounds Against against Sweetpotato Whitefly-crawler (*Bemisia tabaci*) (WF) (BEMITA)

The sweetpotato whitefly (*Bemisia tabaci*) has been reported as a serious pest of cultivated crops world-wide. It has an extremely wide host range attacking more than 500 species of plants from 63 plant families. Weeds often serve as alternate hosts of crop pests. Direct feeding damage is caused by the piercing and sucking sap from the foliage of plants. This feeding causes weakening and early wilting of the plant and reduces the plant growth rate and yield. Indirect damage results from the accumulation of honeydew produced by the whiteflies. Honeydew serves as a substrate for the growth of black sooty mold on leaves and fruit reducing photosynthesis and lessens the market value of the plant or yield. Damage is also caused when sweetpotato whitefly vectors plant viruses. The sweetpotato whitefly is considered the most common and important whitefly vector of plant viruses worldwide.

Foliar spray assay for WF was prepared as follows: Cotton plants (*Gossypium hirsutum*) grown in 3-inch pots, with 1 small (4-5 cm) true leaf, were used as test substrate. The plants were infested with 200-400 whitefly eggs 4-5 days prior to chemical application. Four pots with individual plants were used for each treatment. Tested compounds (2 mg) were dissolved in 1 mL of acetone solvent, forming stock solutions of 2000 ppm tested compound.

The stock solutions were diluted ten times with 0.025% TWEEN® 20 surfactant in $H_2O$ (diluents) to obtain the solution at 200 ppm tested compound. A hand-held aspirator-type sprayer was used for spraying the solution to both sides of cotton leaves until runoff. The control plants (solvent check) were sprayed with the diluent only containing 10% by volume of acetone solvent. Treated plants were held in a holding room for 9 days at approximately 25° C. and ambient relative humidity (RH) prior to grading. Evaluation was conducted by counting the number of live 3-4 nymph stage per plant under a microscope. Percent control was measured by using Abbott's correction formula (W. S. Abbott, "A Method of Computing the Effectiveness of an Insecticide," *J. Econ. Entomol.* 18 (1925), pp. 265-267) as follows.

Corrected % Control=$100*(X-Y)/X$ where
X=No. of live nymphs on solvent check plants and
Y=No. of live nymphs on treated plants.

The results are indicated in TABLE 2. The mortality efficiency of the disclosed pesticidal compounds against GPA and WF insects was rated as shown in TABLE 1.

TABLE 1

Mortality Rating for for GPA (MYZUPE) and WF-crawler (BEMITA)

| % Control (or Mortality) | Rating |
|---|---|
| 80-100 | A |
| More than 0-Less than 80 | B |

TABLE 1-continued

Mortality Rating for for GPA (MYZUPE) and WF-crawler (BEMITA)

| % Control (or Mortality) | Rating |
|---|---|
| Not Tested | C |
| No activity noticed in this bioassay | D |

TABLE 2

Biological Data for GPA (MYZUPE) and WF-crawler (BEMITA) of non-limting examples of the disclosed compounds

| Compound | Pest species | |
|---|---|---|
| | GPA | WF |
| F1 | A | A |
| F2 | A | B |
| F3 | C | B |
| F4 | A | B |
| F5 | A | B |
| F6 | A | A |
| F7 | A | A |
| F8 | A | A |
| F10 | B | B |
| F12 | A | B |
| F13 | A | B |
| F14 | A | B |
| F15 | B | A |
| F17 | B | A |
| F18 | B | B |
| F19 | A | A |
| F20 | A | A |
| F21 | A | A |
| F22 | A | A |
| F23 | A | A |
| F27 | C | C |
| F28 | A | B |
| F29 | A | A |
| F30 | C | C |
| F31 | A | B |
| F32 | B | A |
| F33 | A | B |
| F34 | A | A |
| F37 | A | A |
| F38 | B | D |
| F39 | A | B |
| F40 | A | A |
| F42 | A | A |
| F43 | A | B |
| F46 | A | B |
| F48 | A | B |
| F49 | A | B |
| F50 | A | B |
| F51 | A | A |
| F54 | C | C |
| P18 | A | A |
| P20 | A | C |
| P21 | A | C |
| P26 | A | C |
| P27 | A | A |
| P30 | A | A |
| P31 | A | A |
| P32 | A | B |
| P34 | A | C |
| P35 | A | C |
| P36 | B | A |
| P38 | B | B |
| P39 | B | B |
| CA3 | A | A |
| CA4 | A | C |

Insecticidal Activities of Comparative Compounds Against Green Peach Aphid (GPA) and Sweetpotato Whitefly-Crawler (WF)

The comparative compounds were tested for insecticidal activities against GPA and WF pests using the same test protocols described above for the disclosed compounds. The results are as shown in TABLE 3.

TABLE 3

Biological Data for GPA (MYZUPE) and WF-crawler (BEMITA) of the Comparative Compounds

| Comparative Compound | Pest species | |
|---|---|---|
| | GPA | WF |
| CE1 | D | B |
| CE2 | B | B |
| CE3 | D | D |
| CE4 | D | D |
| CE5 | D | D |
| CE6 | B | D |
| CE7 | B | D |

As shown in TABLES 1-3, the disclosed compounds of present disclosure show significantly improved insecticidal activities against GPA and WF pests, compared to the Comparative compounds.

The following examples serve to explain embodiments of the present invention in more detail. These examples should not be construed as being exhaustive or exclusive as to the scope of this invention.

EXAMPLES

The following examples are for illustration purposes and are not to be construed as limiting the disclosure to only the embodiments disclosed in these examples.

Starting materials, reagents, and solvents that were obtained from commercial sources were used without further purification. Anhydrous solvents were purchased as SURE/SEAL™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures of from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz. $^{13}$C NMR spectral data are in ppm (δ) and were recorded at 75, 100 or 150 MHz. $^{19}$F NMR spectral data are in ppm (δ) and were recorded at 376 MHz, unless otherwise stated.

Example 1

Preparation of 2-(pyridin-3-yl)-6,7-dihydro-2H-pyrazolo[4,3-c]pyridin-4(5H)-one (F2)

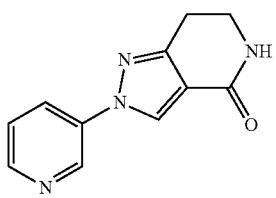

F2

In a dry round-bottomed flask (500 mL), a mixture of 3-hydrazinylpyridine dihydrochloride (4.02 g, 22.1 mmol), piperidine-2,4-dione (2.50 g, 22.1 mmol) and sodium acetate (3.63 g, 44.2 mmol) in dry ethanol (196 mL) and water (24.56 mL) was magnetically stirred overnight at room temperature. The reaction mixture was evaporated to dryness. The residue was diluted with ethanol and toluene, and then evaporated again to dryness under high vacuum to give 4-(2-(pyridin-3-yl)hydrazono)piperidin-2-one, which was used in further synthesis without purification.

A magnetically stirred mixture of 4-(2-(pyridin-3-yl)hydrazono)piperidin-2-one (4.51 g, 22.1 mmol) and dimethylformamide-dimethylacetal (83.0 mL, 618 mmol) in a round-bottomed flask (500 mL) under nitrogen was heated at reflux for 35 minutes. The reaction mixture was evaporated to dryness. The residue was diluted with methanol and dried with silica. The resulting mixture was evaporated to dryness under high vacuum overnight. The crude material was purified via flash column chromatography using 1-15% methanol/dichloromethane as eluent to afford Compound F2 as a light yellow solid (2.50 g, 50%).

Example 2

Preparation of 3-((dimethylamino)methylene)piperidine-2,4-done (C1)

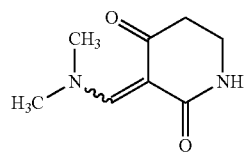

C1

To a solution of piperidine-2,4-dione (2.00 g, 17.7 mmol) in dimethylformamide (70.7 mL) was added 1,1-dimethoxy-N,N-dimethylmethanamine (2.47 mL, 18.6 mmol). The reaction was stirred at 90° C. for 4 hours, then evaporated to dryness under reduced pressure to give Compound C1 as a brown oil (3.17 g, 85%): $^1$H NMR (300 MHz, DMSO-d$_6$) δ 7.94 (s, 1H), 3.24 (s, 2H), 3.13 (s, 2H), 2.87 (s, 3H), 2.71 (s, 3H).

Example 3

Preparation of 6,7-dihydro-2H-pyrazolo[4,3-c]pyridin-4(5H)-one (C2)

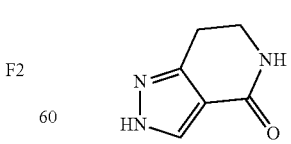

C2

To a solution of (C1) (2.97 g, 17.7 mmol) in ethanol (58.9 mL) was added hydrazine-hydrate (0.859 mL, 17.7 mmol). The reaction was refluxed for 18 hours, cooled to room temperature, and then concentrated under reduced pressure. The crude material was dissolved in methanol and concentrated onto diatomaceous earth. Purification via flash column chromatography using 0-15% methanol/dichloromethane as eluent gave Compound C2 as a yellow solid (0.816 g, 34%): $^1$H NMR (400 MHz, DMSO-d$_6$) δ 13.01 (s, 1H), 8.05 (s, 1H), 7.31-7.19 (m, 1H), 3.36 (td, J=6.7, 2.5 Hz, 2H), 2.91-2.69 (m, 2H); ESIMS m/z 138 ([M+H]+).

Example 4

Preparation of 2-(pyridin-3-yl)-6,7-dihydro-2H-pyrazolo[4,3-c]pyridin-4(5H)-one (F2)

To a solution of Compound C2 (0.100 g, 0.729 mmol) in dimethylformamide (7.29 mL) at 0° C. was added sodium hydride (60% in oil, 0.0320 g, 0.802 mmol). After 15 minutes at room temperature, 3-fluoropyridine (0.0630 mL, 0.729 mmol) was added and the reaction was heated at 100° C. for 18 hours. The reaction was cooled to room temperature, and an additional amount of sodium hydride (60% in oil, 0.0320 g, 0.802 mmol) was added. After 15 minutes at room temperature, the reaction was heated at 100° C. for 4 hours, then at 120° C. for 19 hours. The reaction was concentrated under reduced pressure. The crude material was purified by flash column chromatography using 0-100% methanol/dichloromethane as eluent to give Compound F2 as an off-white solid (0.0400 g, 22%).

Example 5

Preparation of 5-methyl-2-(pyridin-3-yl)-6,7-dihydro-2H-pyrazolo[4,3-c]pyridin-4(5H)-one (F28)

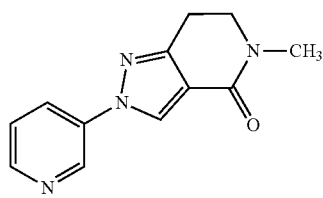

F28

To a suspension of sodium hydride (50% in paraffin oil, 0.066 g, 1.4 mmol) in dry tetrahydrofuran (10 mL) was added (F2) (0.20 g, 0.93 mmol) in dry tetrahydrofuran (2 mL), at 0° C. under nitrogen. Stirring was continued for 10 minutes after which, iodomethane (0.13 g, 0.93 mmol) was added dropwise at 0° C. Reaction was slowly warmed to room temperature, and stirring at room temperature was continued for 2 to 3 hours. The reaction mixture was quenched with a saturated ammonium chloride solution (10 mL) and extracted with ethyl acetate (3×20 mL). The combined organic extracts were washed with brine and dried over anhydrous sodium sulfate. The decanted organic layer was evaporated to dryness under reduced pressure. The crude product was purified via flash column chromatography using ethyl acetate/hexanes as eluent, to provide Compound F28 as a yellow solid (0.060 g).

Example 6

The following molecule was made in accordance with the procedure disclosed in Example 5:

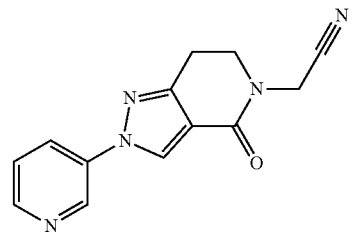

F39

2-[4-Oxo-2-(3-pyridyl)-6,7-dihydropyrazolo[4,3-c]pyridin-5-yl]acetonitrile (Compound F39) was prepared using 2-bromoacetonitrile, and isolated as a brown solid (0.055 g).

Example 7

Preparation of 5-(cyclopropylmethyl)-2-(pyridin-3-yl)-6,7-dihydro-2H-pyrazolo[4,3-c]pyridin-4(5H)-one (F1)

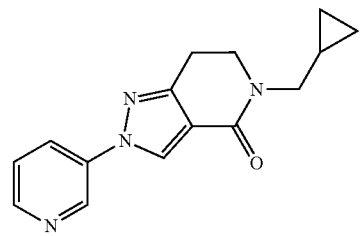

F1

A suspension of Compound F2 (0.700 g, 3.27 mmol), sodium hydroxide (1.30 g, 32.7 mmol) and cylcopropylmethyl bromide (4.41 g, 32.7 mmol) in dry dimethylformamide (35 mL) was stirred at room temperature for 18 hours. The reaction was diluted with ethyl acetate (75 mL), and then washed with water (3×50 mL) and brine (50 mL). The reacting solution was dried over anhydrous sodium sulfate, filtered, and evaporated to dryness under reduced pressure. The residue was purified via flash column chromatography using ethyl acetate/hexanes as eluent to give Compound F1 as a yellow solid (0.030 g, 24%).

Example 8

The following molecules were made in accordance with the procedure disclosed in Example 7:

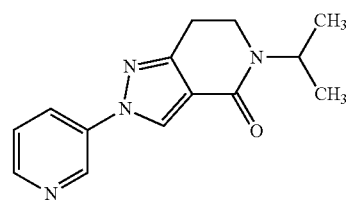

F6

5-Isopropyl-2-(3-pyridyl)-6,7-dihydropyrazolo[4,3-c]pyridin-4-one (Compound F6) was prepared using 2-iodopropane, and was isolated as a gum (0.180 g, 22%).

Example 9

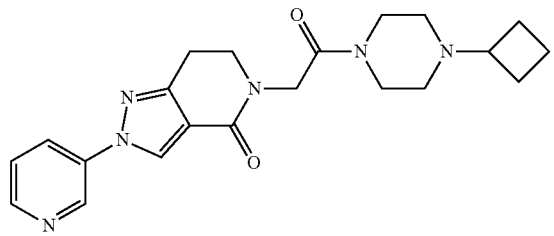

F42

Using the procedure disclosed in Example 7, 5-[2-(4-Cyclobutylpiperazin-1-yl)-2-oxo-ethyl]-2-(3-pyridyl)-6,7-dihydropyrazolo[4,3-c]pyridin-4-one (Compound F42) was prepared using 2-chloro-1-(4-cyclobutylpiperazin-1-yl)ethanone (WO 200/7016496), and was isolated as an off-white solid (0.070 g, 19%).

Example 10

Preparation of 5-allyl-2-(pyridin-3-yl)-6,7-dihydro-2H-pyrazolo[4,3-c]pyridin-4(5H)-one (F31)

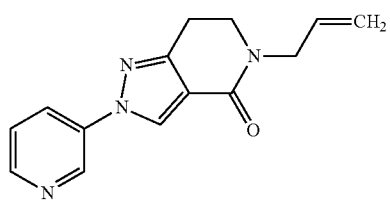

F31

To a solution of Compound F2 (0.100 g, 0.467 mmol) in dimethylformamide (4.67 mL) at 0° C. was added sodium hydride (60% in oil, 0.0220 g, 0.560 mmol). After 10 minutes at 0° C. and 15 minutes at room temperature, the reaction was cooled to 0° C. and allyl bromide (0.0570 mL, 0.654 mmol) was added. After 10 minutes at 0° C., the reaction was stirred at room temperature for 3.5 hours, whereupon it was diluted with brine and extracted with ethyl acetate. The combined organic phases were washed with brine, dried over magnesium sulfate, and concentrated. The residue was purified via flash column chromatography using 0-15% methanol/dichloromethane as eluent to give Compound 31 as a yellow solid (0.0600 g, 50%).

Example 11

The following molecules were made in accordance with the procedure disclosed in Example 10:

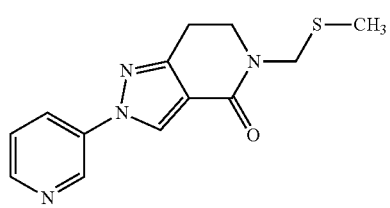

F20

Using the procedure disclosed in Example 10, 5-(Methylsulfanylmethyl)-2-(3-pyridyl)-6,7-dihydropyrazolo[4,3-c]pyridin-4-one (Compound F20) was prepared using (chloromethyl)(methyl)sulfane, and was isolated as a yellow solid (0.029 g, 22%).

Example 12

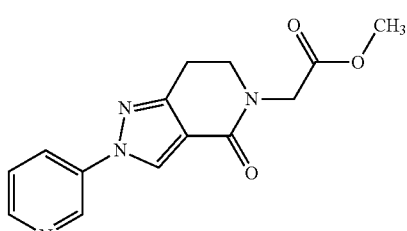

F30

Using the procedure disclosed in Example 10, Methyl 2-[4-oxo-2-(3-pyridyl)-6,7-dihydropyrazolo[4,3-c]pyridin-5-yl]acetate (Compound F30) was prepared using methyl 2-bromoacetate, and was isolated as a yellow solid (0.166 g, 24%).

Example 13

Preparation of 5-(2-fluorobenzyl)-2-(pyridin-3-yl)-6,7-dihydro-2H-pyrazolo[4,3-c]pyridin-4(5H)-one (F17)

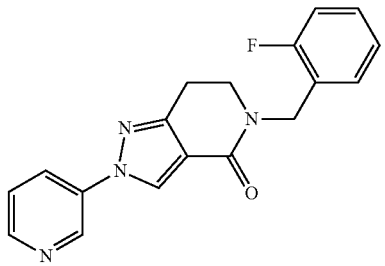

F17

To a magnetically stirred mixture of Compound F2 (0.100 g, 0.467 mmol) in dry dimethylformamide (2 mL) was added sodium hydride (60% in oil, 0.0205 g, 0.513 mmol) in a dry vial (25 mL) under nitrogen. The reaction mixture was stirred at room temperature for 10 minutes, then 1-(bromomethyl)-2-fluorobenzene (0.106 g, 0.560 mmol) was added, and the mixture was allowed to stir at room temperature overnight. The reaction mixture was diluted with ice-cold water/hydrogen chloride (2N) and extracted with dichloromethane twice. The combined dichloromethane extracts were evaporated, and the crude material was purified by reverse phase high pressure liquid chromatography (Gilson-1 Column-Atlantis Prep; T3 5 um OBD 30×100 mm; Flow rate-29.15 mL/minute; Gradient-(10 to 70%) acetonitrile and water with 0.1% acetic acid) to provide Compound F17 as an off-white solid (0.030 g, 19%).

Example 14

The following molecules were made in accordance with the procedure disclosed in Example 13:

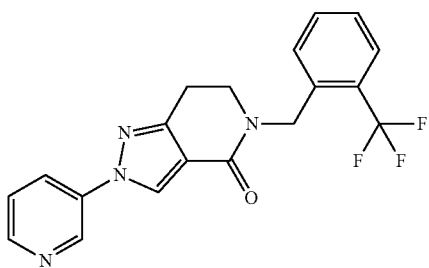

2-(3-Pyridyl)-5-[[2-(trifluoromethyl)phenyl]methyl]-6,7-dihydropyrazolo[4,3-c]pyridin-4-one (Compound F32) was prepared using 1-(bromomethyl)-2-(trifluoromethyl) benzene, and was isolated as an off-white solid (0.078 g, 43%).

Example 15

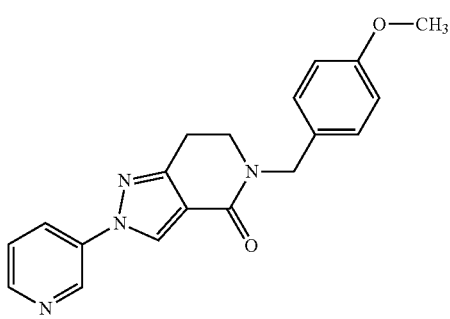

5-[(4-Methoxyphenyl)methyl]-2-(3-pyridyl)-6,7-dihydropyrazolo[4,3-c]pyridin-4-one (Compound F23) was prepared using 1-(chloromethyl)-4-methoxybenzene, and was isolated as an off-white solid (0.049 g, 30%).

Example 16

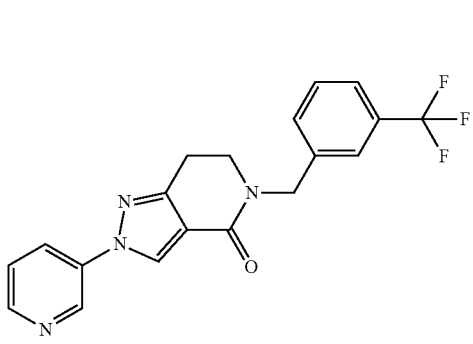

Using the procedure disclosed in Example 13, 2-(3-Pyridyl)-5-[[3-(trifluoromethyl)phenyl]methyl]-6,7-dihydropyrazolo[4,3-c]pyridin-4-one (Compound F29) was prepared using 1-(chloromethyl)-3-(trifluoromethyl)benzene, and was isolated as an off-white solid (0.0056 g, 56%).

Example 17

Preparation of 5-(4-fluorobenzyl)-2-(pyridin-3-yl)-6,7-dihydro-2H-pyrazolo[4,3-c]pyridin-4(5H)-one (F3)

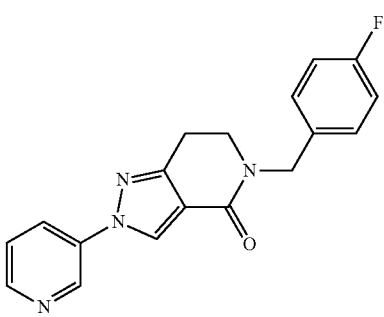

To a magnetically stirred mixture of Compound F2 (0.050 g, 0.23 mmol) in dry dimethylformamide (1.2 mL) was added lithium bis(trimethylsilyl)amide (1M in toluene, 0.26 mL, 0.26 mmol) in a dry vial (5 mL) under argon. The reaction mixture was stirred for 5 minutes at room temperature. Then, 1-(bromomethyl)-4-fluorobenzene (0.034 mL, 0.28 mmol) was added, and the reaction mixture was allowed to stir at room temperature overnight. The reaction mixture was diluted with ice-cold water/hydrogen chloride (2N) and extracted with dichloromethane twice. The combined dichloromethane extracts were evaporated, and the crude material was purified by reverse phase high pressure liquid chromatography (Gilson-1 Column-Atlantis Prep; T3 5 um OBD 30×100 mm; Flow rate-29.15 mL/minute; Gradient-(10 to 90%) acetonitrile and water with 0.1% acetic acid) to afford Compound F3 as a white solid (0.0047 g, 6%).

Example 18

The following molecules were made in accordance with the procedure disclosed in Example 17:

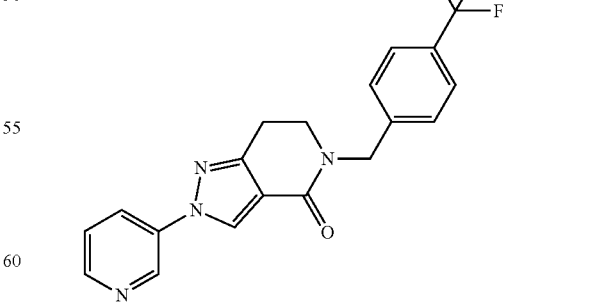

2-(3-Pyridyl)-5-[[4-(trifluoromethyl)phenyl]methyl]-6,7-dihydropyrazolo[4,3-c]pyridine-4-one (Compound F50) was prepared using 1-(chloromethyl)-4-(trifluoromethyl) benzene, and was isolated as a white solid (0.0501 g, 55%).

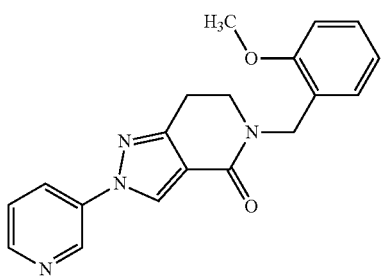

F15

Using the procedure disclosed in Example 17, 5-[(2-Methoxyphenyl)methyl]-2-(3-pyridyl)-6,7-dihydropyrazolo[4,3-c]pyridin-4-one (Compound F15) was prepared using 1-(chloromethyl)-2-methoxybenzene, and was isolated as a yellow wax (0.0337 g, 41%).

Example 20

Preparation of ethyl 2-(4-oxo-2-(pyridin-3-yl)-6,7-dihydro-2H-pyrazolo[4,3-c]pyridin-5(4H)-yl)acetate (F8)

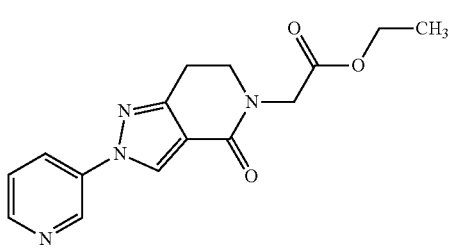

F8

In a dry round-bottomed flask (50 mL) under nitrogen, a magnetically stirred mixture of Compound F2 (0.500 g, 2.33 mmol) in dry dimethylformamide (11 mL) and dry hexamethylphosphoramide (1 mL) was stirred at room temperature until all of the starting material dissolved, then cooled to ice-bath temperatures, and lithium bis(trimethylsilyl)amide (1M in toluene, 2.33 mL, 2.33 mmol) was added. The light yellow reaction mixture became dark orange and was stirred at ice-bath temperatures for 5 minutes. The ethyl 2-chloroacetate (0.500 mL, 4.67 mmol) was added, and the reaction mixture was stirred for 30 minutes. The reaction mixture was diluted with ice-water and a few drops of hydrogen chloride (2N). The contents were further diluted with dichloromethane and aqueous sodium bicarbonate, and the layers were separated. The organic extract was evaporated and purified via flash column chromatography using 0, 5, 10% methanol/dichloromethane as eluent to provide Compound F8 as a yellow solid (0.408 g, 55%).

Example 21

Preparation of 5-(3-(methylthio)propanoyl)-2-(pyridin-3-yl)-6,7-dihydro-2H-pyrazolo[4,3-c]pyridin-4(5H)-one Compound F12

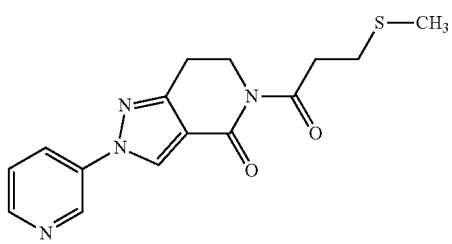

F12

To a solution of Compound F2 (0.100 g, 0.467 mmol) in 1,2-dichloroethane (1.87 mL) was added 3-(methylthio)propanoyl chloride (0.142 g, 1.03 mmol) and N-ethyl-N-isopropylpropan-2-amine (0.179 mL, 1.03 mmol). The reaction vial was capped, and the reaction was heated at 100° C. for 3 hours in a CEM Discover microwave reactor with external IR-sensor temperature monitoring from the bottom of the vessel. The solution was put into a separatory funnel. Saturated aqueous sodium bicarbonate was added, and the mixture was extracted with ethyl acetate. The organic extracts were combined, dried over magnesium sulfate and concentrated. The residue was purified by flash column chromatography using 0-15% methanol/dichloromethane as eluent to give the title compound F12 as a yellow oil (0.011 g, 7%).

Example 22

Preparation of 5-(pyridin-2-yl)-2-(pyridin-3-yl)-6,7-dihydro-2H-pyrazolo[4,3-c]pyridin-4(5H)-one (F43)

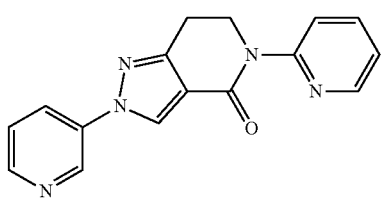

F43

To a solution of Compound F2 (0.080 g, 0.37 mmol) in dioxane (3.7 mL) was added 2-bromopyridine (0.043 mL, 0.45 mmol), cesium carbonate (0.24 g, 0.75 mmol), copper (I) iodide (3.6 mg, 0.019 mmol) and trans-1,2-diaminocyclohexane (0.0045 mL, 0.037 mmol). The reaction was heated at reflux for 15 hours under nitrogen. The reaction was cooled to room temperature, diluted with brine, and extracted with ethyl acetate. The combined organic phases were dried over magnesium sulfate and concentrated. The residue was purified by flash column chromatography using 0-15% methanol/dichloromethane as eluent to give Compound F43 as a beige solid (0.052 g, 47%).

Example 23

Preparation of 2-(pyridin-3-yl)-5-(5-(trifluoromethyl)pyrdin-2-yl)-6,7-dihydro-2H-pyrazolo[4,3-c]pyridin-4(5H)-one (F37)

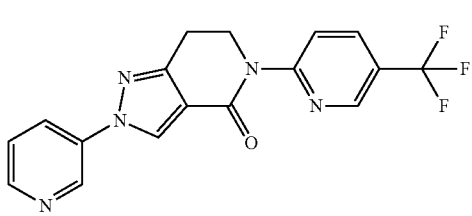

To a solution of Compound F2 (0.050 g, 0.23 mmol) in dioxane (2.3 mL) was added 2-bromo-5-(trifluoromethyl)pyridine (0.063 g, 0.28 mmol), 4,5-bis(diphenylphosphino)-9,9-dimethylxanthene (Xantphos) (0.0068 g, 0.012 mmol), and cesium carbonate (0.11 g, 0.35 mmol). The reaction was degassed with nitrogen and tris(dibenzylideneacetone)dipalladium (0) (0.0021 g, 0.0023 mmol) was added. The reaction was heated at 120° C. for 6 hours. The reaction was cooled to room temperature, diluted with brine, and extracted with ethyl acetate. The combined organic phases were dried over magnesium sulfate and concentrated. The residue was purified by flash column chromatography using 0-15% methanol/dichloromethane as eluent to provide Compound F37 as a white solid (0.069 g, 82%).

Example 24

The following molecules were made in accordance with the procedures disclosed in Example 23:

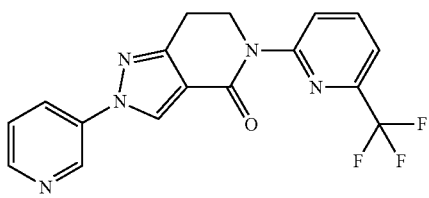

2-(3-Pyridyl)-5-[6-(trifluoromethyl)-2-pyridyl]-6,7-dihydropyrazolo[4,3-c]pyridin-4-one (Compound F46) was prepared using 2-bromo-6-(trifluoromethyl)pyridine, and was isolated as a white solid (0.054 g, 64%).

Example 25

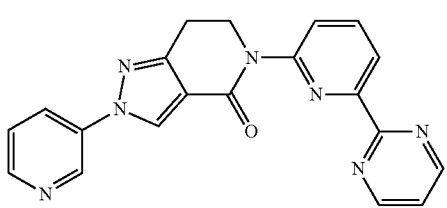

Using the procedure disclosed in Example 23, 2-(3-Pyridyl)-5-(6-pyrimidin-2-yl-2-pyridyl)-6,7-dihydropyrazolo[4,3-c]pyridin-4-one (Compound F38) was prepared using 2-(6-bromopyridin-2-yl)pyrimidine, and was isolated as a faint yellow solid (0.108 g, 83%).

Example 26

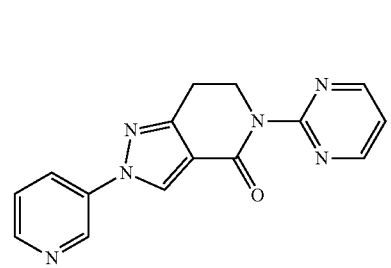

Using the procedure disclosed in Example 23, 2-(3-Pyridyl)-5-pyrimidin-2-yl-6,7-dihydropyrazolo[4,3-c]pyridin-4-one (Compound F34) was prepared using 2-chloropyrimidine, and was isolated as a yellow solid (0.016 g, 23%).

Example 27

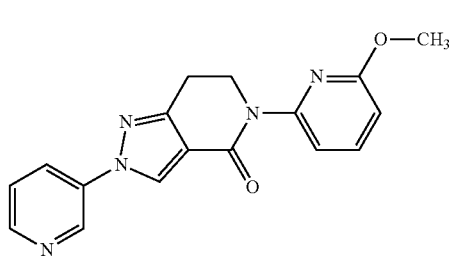

Using the procedure disclosed in Example 23, 5-(6-Methoxy-2-pyridyl)-2-(3-pyridyl)-6,7-dihydropyrazolo[4,3-c]pyridin-4-one (Compound F18) was prepared using 2-bromo-6-methoxypyridine, and was isolated as a faint yellow solid (0.039 g, 52%).

Example 28

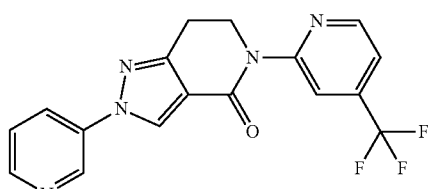

Using the procedure disclosed in Example 23, 2-(3-Pyridyl)-5-[4-(trifluoromethyl)-2-pyridyl]-6,7-dihydropyrazolo[4,3-c]pyridin-4-one (Compound F7) was prepared using 2-bromo-4-(trifluoromethyl)pyridine, and was isolated as a yellow solid (0.044 g, 53%).

Example 29

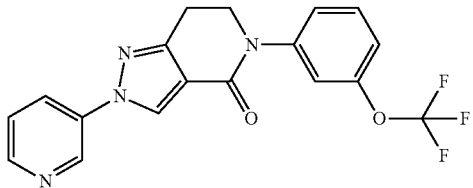

F22

Using the procedure disclosed in Example 23, 2-(3-Pyridyl)-5-[3-(trifluoromethoxy)phenyl]-6,7-dihydropyrazolo[4,3-c]pyridin-4-one (Compound F22) was prepared using 1-bromo-3-(trifluoromethoxy)benzene, and was isolated as a yellow solid (0.046 g, 53%).

Example 30

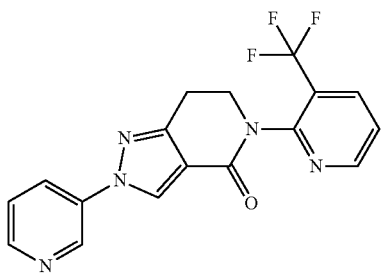

F10

Using the procedure disclosed in Example 23, 2-(3-Pyridyl)-5-[3-(trifluoromethyl)-2-pyridyl]-6,7-dihydropyrazolo[4,3-c]pyridin-4-one (Compound F10) was prepared using 2-bromo-3-(trifluoromethyl)pyridine, and was isolated as a yellow oil (0.018 g, 21%).

Example 31

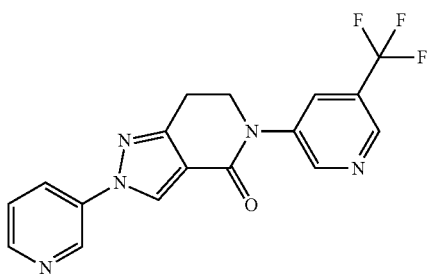

F21

Using the procedure disclosed in Example 23, 2-(3-Pyridyl)-5-[5-(trifluoromethyl)-3-pyridyl]-6,7-dihydropyrazolo[4,3-c]pyridin-4-one (Compound F21) was prepared using 3-bromo-5-(trifluoromethyl)pyridine, and was isolated as a yellow solid (0.0182 g, 21%).

Example 32

Using the procedure disclosed in Example 23, 2-(3-Pyridyl)-5-[6-(trifluoromethyl)pyrimidin-4-yl]-6,7-dihydropyrazolo[4,3-c]pyridin-4-one (Compound F48) was prepared using 4-bromo-6-(trifluoromethyl)pyrimidine, and was isolated as a light brown solid (0.0553 g, 63%).

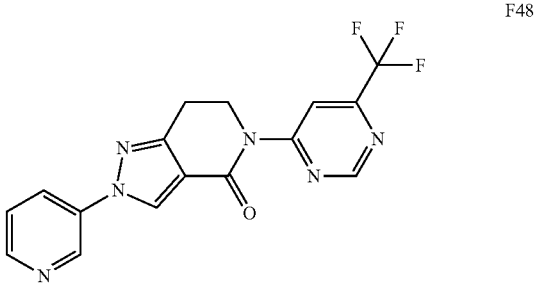 [SMILES: O=C1c2cn(-c3cccnc3)nc2CCN1c1cc(C(F)(F)F)ncn1]

F48

Example 33

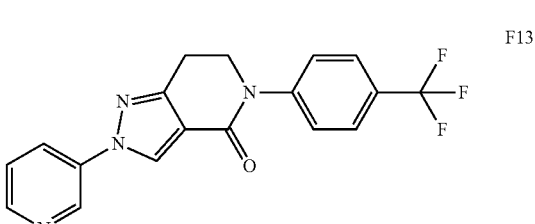

F49

Using the procedure disclosed in Example 23, 5-(5-Fluoro-2-pyridyl)-2-(3-pyridyl)-6,7-dihydropyrazolo[4,3-c]pyridin-4-one (Compound F49) was prepared using 2-bromo-5-fluoropyridine, and was isolated as a yellow solid (0.0275 g, 36%).

Example 34

F13

Using the procedure disclosed in Example 23, 2-(3-Pyridyl)-5-[4-(trifluoromethyl)phenyl]-6,7-dihydropyrazolo[4,3-c]pyridin-4-one (Compound F13) was prepared using 1-bromo-4-(trifluoromethyl)benzene, and was isolated as a yellow solid (0.0169 g, 19%).

Example 35

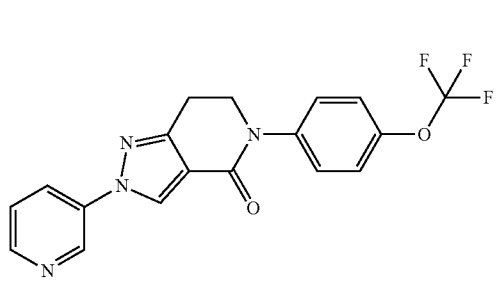

Using the procedure disclosed in Example 23, 2-(3-Pyridyl)-5-[4-(trifluoromethoxy)phenyl]-6,7-dihydropyrazolo[4,3-c]pyridin-4-one (Compound F14) was prepared using 1-bromo-4-(trifluoromethoxy)benzene, and was isolated as a yellow solid (0.036 g, 39%).

Example 36

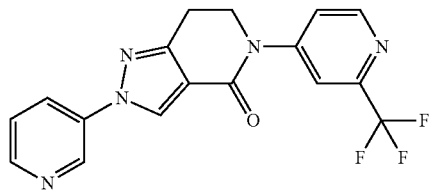

Using the procedure disclosed in Example 23, 2-(3-Pyridyl)-5-[2-(trifluoromethyl)-4-pyridyl]-6,7-dihydropyrazolo[4,3-c]pyridin-4-one (Compound F5) was prepared using 4-bromo-2-(trifluoromethyl)pyridine, and was isolated as a dark yellow solid (0.0552 g, 63%).

Example 37

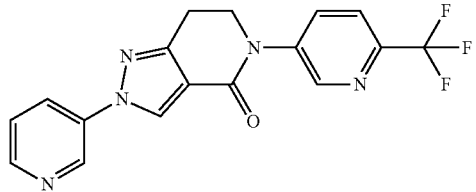

Using the procedure disclosed in Example 23, 2-(3-Pyridyl)-5-[6-(trifluoromethyl)-3-pyridyl]-6,7-dihydropyrazolo[4,3-c]pyridin-4-one (Compound F33) was prepared using 5-bromo-2-(trifluoromethyl)pyridine, and was isolated as a yellow solid (0.0161 g, 16%).

Example 38

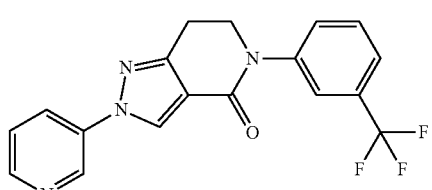

2-(3-Pyridyl)-5-[3-(trifluoromethyl)phenyl]-6,7-dihydropyrazolo[4,3-c]pyridin-4-one (Compound F4) was prepared using 1-bromo-3-(trifluoromethyl)benzene, and was isolated as a yellow solid (0.0519 g, 56%).

Example 39

Preparation of 5-(2-hydroxyethyl)-2-(pyridin-3-yl)-6,7-dihydro-2H-pyrazolo[4,3-c]pyridin-4(5H)-one (F27)

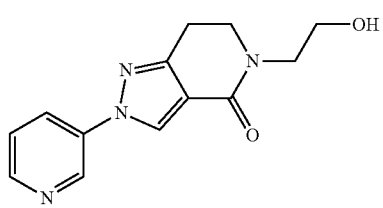

To a magnetically stirred mixture of Compound F8 (0.066 g, 2.2 mmol) in dry ethanol (7.3 mL) was added sodium borohydride (0.083 g, 2.2 mmol) in a dry vial (50 mL) under nitrogen. The reaction mixture was stirred at room temperature overnight. The reaction mixture was diluted with ice-water, and the pH adjusted to neutral with hydrogen chloride (2N). The resulting mixture was evaporated to dryness. The crude solid was extracted several times with dichloromethane/ethanol, and the resulting washings were filtered and evaporated onto silica. The crude material was purified via flash column chromatography using 0-10% methanol/dichloromethane as eluent to afford Compound F27 as a white solid (0.33 g, 56%).

Example 40

Preparation of 5-(2-chloroethyl)-2-(pyridin-3-yl)-6,7-dihydro-2H-pyrazolo[4,3-c]pyridin-4(5H)-one (F54)

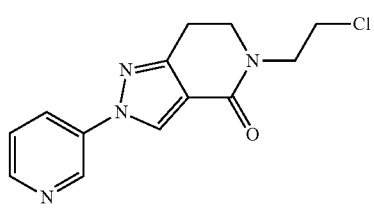

To a magnetically stirred mixture of Compound F27 (0.332 g, 1.29 mmol) in dry dichloromethane (6.4 mL) at ice-bath temperatures was added triethylamine (0.358 mL, 2.57 mmol) and tosyl-chloride (0.245 g, 1.29 mmol), followed by 4-dimethylaminopyridine (0.079 g, 0.64 mmol) in a dry round-bottomed flask (50 mL) under nitrogen. The reaction mixture was allowed to warm to room temperature over the weekend. The reaction mixture was purified via flash column chromatography using 0-10% methanol/dichloromethane as eluent to afford Compound F54 as a yellow solid (0.264 g, 71%).

Example 41

Preparation of 2-(pyridin-3-yl)-5-(2-((3,3,3-trifluoropropyl)thio)ethyl)-6,7-dihydro-2H-pyrazolo[4,3-c]pyridin-4(5H)-one (F19)

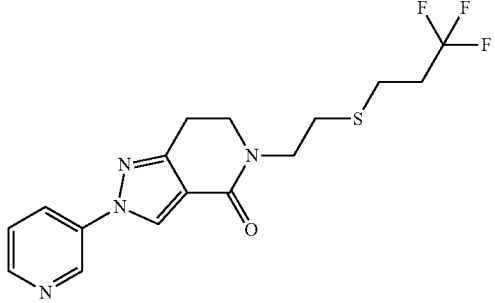

F19

To a magnetically stirred mixture of Compound F54 (0.132 g, 0.477 mmol) and 3,3,3-trifluoropropane-1-thiol (0.0518 mL, 0.477 mmol) in dry acetonitrile (2.39 mL) was added cesium carbonate (0.155 g, 0.477 mmol) in a dry vial (25 mL) under nitrogen. The reaction mixture was stirred at room temperature overnight. The reaction mixture was purified via flash column chromatograph using 50-100% ethyl acetate/dichloromethane as eluent to provide Compound 19 as a white solid (0.0561 g, 30%).

Example 42

Preparation of 5-(2-(methylthio)ethyl)-2-(pyridin-3-yl)-6,7-dihydro-2H-pyrazolo[4,3-c]pyridin-4(5H)-one (F40)

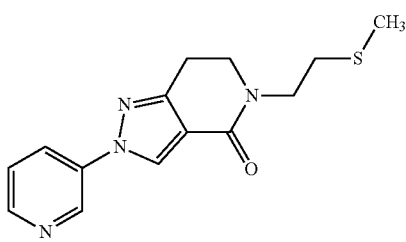

F40

A magnetically stirred mixture of Compound F54 (0.132 g, 0.477 mmol) and sodium thiomethoxide (0.0334 g, 0.477 mmol) in dry acetonitrile (2.39 mL) in a dry vial (25 mL) under nitrogen was stirred at room temperature overnight. The reaction mixture was purified via flash column chromatography using 0-20% methanol/ethyl acetate as eluent to afford Compound 40 as a white solid (0.0124 g, 9%).

Example 43

Preparation of 5-((methylsulfonyl)methyl)-2-(pyridin-3-yl)-6,7-dihydro-2H-pyrazolo[4,3-c]pyridin-4(5H)-one (F51)

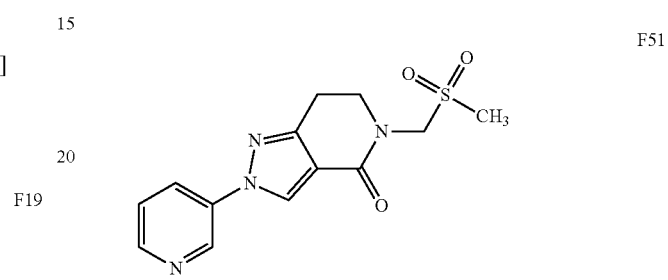

F51

To a solution of Compound F20 (0.050 g, 0.18 mmol) in acetic acid (1.8 mL) at room temperature was added sodium perborate tetrahydrate (0.062 g, 0.40 mmol). After 1 hour at 55° C., the reaction was cooled to room temperature. The reaction was diluted (carefully) in saturated aqueous sodium bicarbonate and ethyl acetate. The layers were separated and the aqueous layer was extracted with ethyl acetate. The combined organic extracts were washed with brine, dried over sodium sulfate, filtered, and concentrated in vacuo. The residue was purified via flash column chromatography using 0-15% methanol/dichloromethane as eluent to provide Compound 51 as a faint yellow solid (0.0311 g, 53%).

Example 44

Preparation of 2-(4-oxo-2-(pyridin-3-yl)-2,4,6,7-tetrahydro-5H-pyrazolo[4,3-c]pyridin-5-yl)acetaldehyde (CA1)

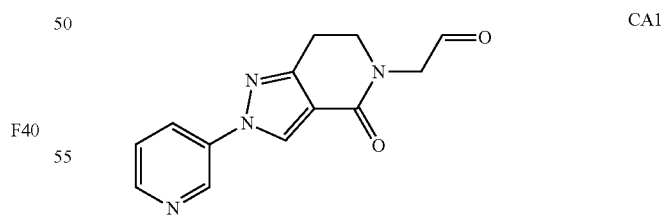

CA1

A mixture of Compound F27 (0.258 g, 1.00 mmol) and Dess-Martin periodinane (0.509 g, 1.20 mmol) in dimethylsulfoxide (8.5 mL) was stirred at room temperature for 12 hours. The mixture was evaporated to dryness and diluted with methanol (100 mL) and filtered. The solvent was removed to provide Compound CA1 as an oil as a mixture with the methylacetal (0.200 g, quant): ESIMS m/z 257 ([M+H]+).

Example 45

Preparation of 2-(4-oxo-2-(pyridin-3-yl)-2,4,6,7-tetrahydro-5H-pyrazolo[4,3-c]pyridin-5-yl)acetaldehyde O-methyl oxime (P26)

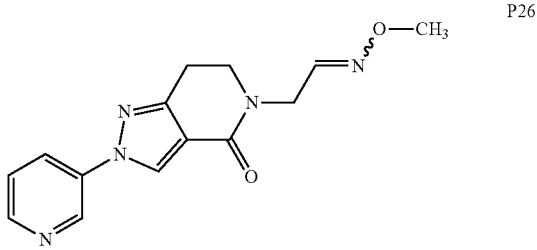 [SMILES: CON=CCN1CCc2nn(-c3cccnc3)cc2C1=O]

P26

To a mixture of Compound CA1 (0.100 g) in ethanol (10 mL) was added methoxyammonium chloride (0.0830 g, 1.00 mmol) and acetic acid (0.180 g, 3.00 mmol). The mixture was stirred at room temperature for 12 hours. The solvent was removed. The crude product was purified by preparative-thin layer chromatography to provide Compound P26 as a white solid (0.0360 g, 25%).

Example 46

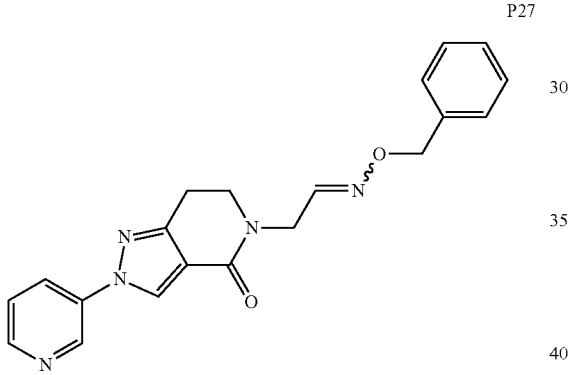

P27

Using the procedure disclosed in Example 45, 2-(4-oxo-2-(pyridin-3-yl)-2,4,6,7-tetrahydro-5H-pyrazolo[4,3-c]pyridin-5-yl)acetaldehyde O-benzyl oxime (Compound P27) was prepared using benzyloxyammonium chloride, and was isolated as a white solid (0.036 g, 16%).

Example 47

Preparation of 2-(4-oxo-2-(pyridin-3-yl)-2,4,6,7-tetrahydro-5H-pyrazolo[4,3-c]pyridin-5-yl)acetic acid (CA2)

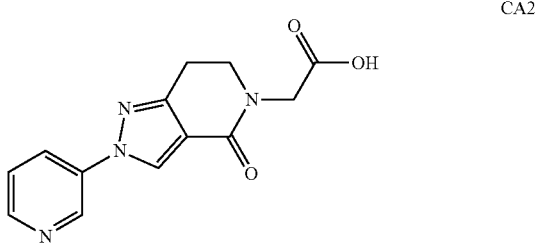 [SMILES: O=C(O)CN1CCc2nn(-c3cccnc3)cc2C1=O]

CA2

To a solution of Compound F8 (1.5 g, 5.0 mmol) in methanol (50 mL) and tetrahydrofuran (25 mL) was added aqueous sodium hydroxide (50 mL, 1 mmol) at room temperature, then stirred for 1 hour. The mixture was adjust to pH 6 with hydrochloric acid (2 N). The mixture was evaporated to dryness, washed with methanol in dichloromethane (methanol/dichloromethane 1:8, 200 mL) and filtered. The filtrate was concentrated to provide Compound CA2 as a yellow solid (1.35 g, 100%). The product was used for next step without further purification or characterization.

Example 48

Preparation of N-methoxy-N-methyl-2-(4-oxo-2-(pyridin-3-yl)-2,4,6,7-tetrahydro-5H-pyrazolo[4,3-c]pyridin-5-yl)acetamide (CA3)

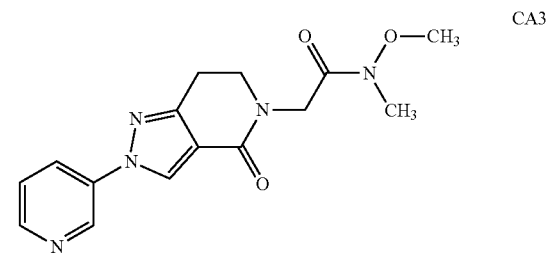 [SMILES: CON(C)C(=O)CN1CCc2nn(-c3cccnc3)cc2C1=O]

CA3

To a solution of Compound CA2 (1.36 g, 5.00 mmol) in N,N-dimethylformamide (50 mL) was added N,O-dimethylhydroxylamine hydrochloride (0.536 g, 5.50 mmol), triethylamine (0.808 g, 8.00 mmol), 1-hydroxybenzotriazole (0.810 g, 6.00 mmol), and 1-ethyl-3-(3-dimethylaminopropyl)carbodiimide hydrochloride (1.34 g, 7.00 mmol). The mixture was stirred at room temperature overnight. The reaction mixture was diluted with hydrochloric acid (2 N) (100 mL), extracted with ethyl acetate (2×100 mL). The aqueous phase was adjusted to pH 8 with sodium hydroxide and extracted with dichloromethane (3×100 mL). The combined organic layer was dried over sodium sulfate, filtered, and concentrated to provide Compound CA3 as a yellow solid (1.42 g, 90%): mp 193-195° C.; $^1$H NMR (400 MHz, CDCl$_3$) δ 9.02 (d, J=2.5 Hz, 1H), 8.61 (dd, J=4.8, 1.4 Hz, 1H), 8.38 (s, 1H), 8.03-8.02 (m, 1H), 7.45 (dd, J=8.3, 4.8 Hz, 1H), 4.50 (s, 2H), 3.85-3.78 (m, 5H), 3.24 (s, 3H), 3.15 (t, J=6.7 Hz, 2H); ESIMS m/z 316 ([M+H]+).

Example 49

Preparation of 5-(2-oxopropyl)-2-(pyridin-3-yl)-2,5,6,7-tetrahydro-4H-pyrazolo[4,3-c]pyridin-4-one (CA4)

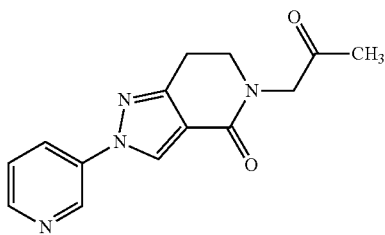

CA4

To a solution of Compound CA3 (1.33 g, 4.22 mmol), under nitrogen in anhydrous tetrahydrofuran (66 mL) was added a solution of methylmagnesium bromide in tetrahydrofuran (1 M, 8.00 mL, 8.00 mmol) at 0° C. The reaction was warmed to room temperature and stirred for 2 hours. The reaction mixture was added to saturated aqueous ammonium chloride (120 mL) and extracted with ethyl acetate (2×120 mL). The combined organic layers were dried over sodium sulfate, filtered, and concentrated. Purification by flash column chromatography provided Compound CA4 as a white solid (0.391 g, 28%): mp 206-207° C.; $^1$H NMR (400 MHz, CDCl$_3$) δ 9.03 (d, J=2.3 Hz, 1H), 8.61 (d, J=3.8 Hz, 1H), 8.40 (s, 1H), 8.04 (ddd, J=8.3, 2.6, 1.4 Hz, 1H), 7.45 (dd, J=8.3, 4.7 Hz, 1H), 4.39 (s, 2H), 3.71 (t, J=6.7 Hz, 2H), 3.13 (t, J=6.7 Hz, 2H), 2.24 (s, 3H); ESIMS m/z 271 ([M+H]+).

Example 50

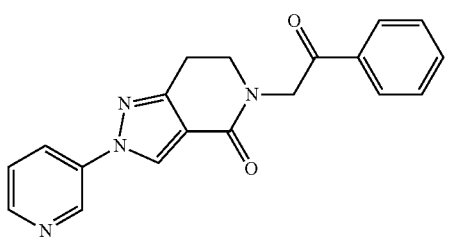

P18

Using the procedure disclosed in Example 49, 5-(2-oxo-2-phenylethyl)-2-(pyridin-3-yl)-2,5,6,7-tetrahydro-4H-pyrazolo[4,3-c]pyridin-4-one (Compound P18) was prepared using phenylmagnesium bromide, and was isolated as a white solid (0.430 g, 26%).

Example 51

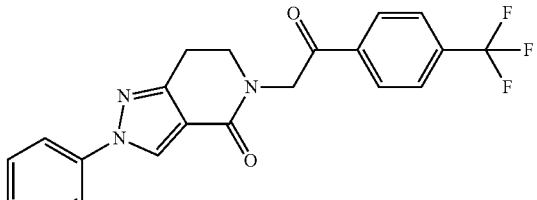

P21

Using the procedure disclosed in Example 49, 5-(2-oxo-2-(4-(trifluoromethyl)phenyl)ethyl)-2-(pyridin-3-yl)-2,5,6,7-tetrahydro-4H-pyrazolo[4,3-c]pyridin-4-one (Compound P21) was prepared using (4-(trifluoromethyl)phenyl)magnesium bromide, and was isolated as a white solid (0.335 g, 27%).

Example 52

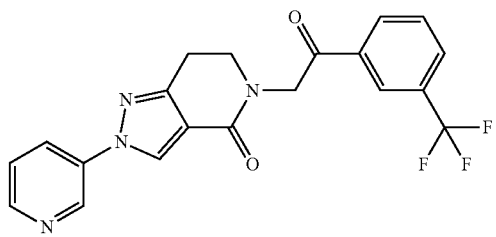

P20

Using the procedure disclosed in Example 49, 5-(2-oxo-2-(3-(trifluoromethyl)phenyl)ethyl)-2-(pyridin-3-yl)-2,5,6,7-tetrahydro-4H-pyrazolo[4,3-c]pyridin-4-one (Compound P20) was prepared using (3-(trifluoromethyl)phenyl)magnesium bromide, and was isolated as a white solid (0.270 g, 21%).

Example 53

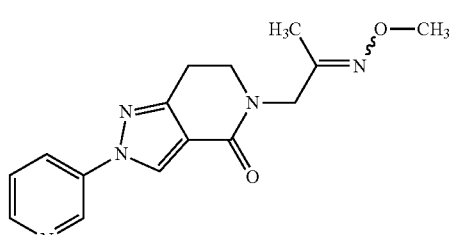

P30

Using the procedure disclosed in Example 45, 5-(2-(methoxyimino)propyl)-2-(pyridin-3-yl)-2,5,6,7-tetrahydro-4H-pyrazolo[4,3-c]pyridin-4-one (Compound P30) was prepared using Compound CA4, and was isolated as a white solid (0.069 g, 77%).

Example 54

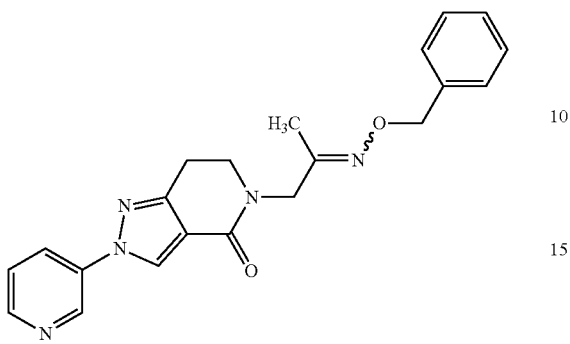

P31

Using the procedure disclosed in Example 45, 5-(2-((benzyloxy)imino)propyl)-2-(pyridin-3-yl)-2,5,6,7-tetrahydro-4H-pyrazolo[4,3-c]pyridin-4-one (Compound P31) was prepared using Compound CA4 and benzyloxyammonium chloride and was isolated as a white solid (0.096 g, 58%).

Example 55

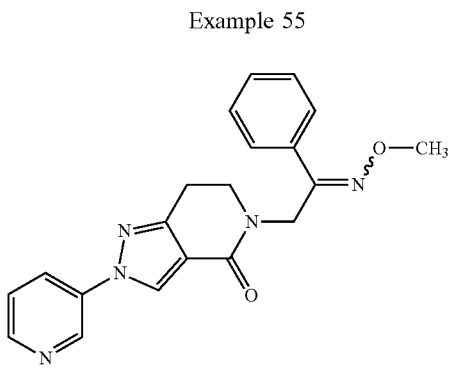

P32

Using the procedure disclosed in Example 45, 5-(2-(methoxyimino)-2-phenylethyl)-2-(pyridin-3-yl)-2,5,6,7-tetrahydro-4H-pyrazolo[4,3-c]pyridin-4-one (Compound P32) was prepared using Compound P18 and methyloxyammonium chloride and was isolated as a white solid (0.058 g, 53%).

Example 56

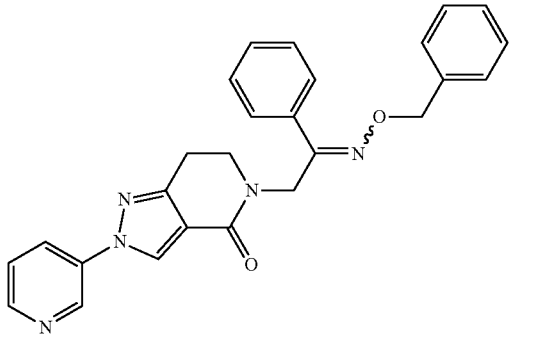

P36

Using the procedure disclosed in Example 45, 5-(2-((benzyloxy)imino)-2-phenylethyl)-2-(pyridin-3-yl)-2,5,6,7-tetrahydro-4H-pyrazolo[4,3-c]pyridin-4-one (Compound P36) was prepared using Compound P18 and benzyloxyammonium chloride and was isolated as a white solid (0.073 g, 55%).

Example 57

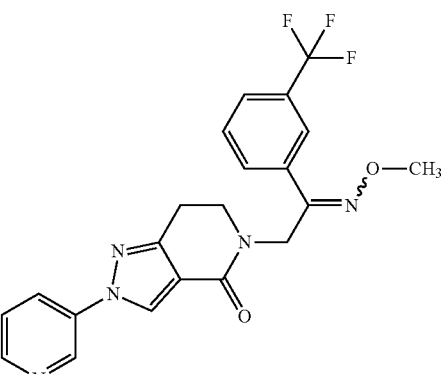

P34

Using the procedure disclosed in Example 45, 5-(2-(methoxyimino)-2-(3-(trifluoromethyl)phenyl)ethyl)-2-(pyridin-3-yl)-2,5,6,7-tetrahydro-4H-pyrazolo[4,3-c]pyridin-4-one (Compound P36) was prepared using Compound P20 and methyloxyammonium chloride and was isolated as a white solid (0.027 g, 25%).

Example 58

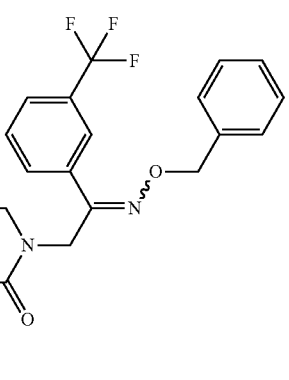

P38

Using the procedure disclosed in Example 45, 5-(2-((benzyloxy)imino)-2-(3-(trifluoromethyl)phenyl)ethyl)-2-(pyridin-3-yl)-2,5,6,7-tetrahydro-4H-pyrazolo[4,3-c]pyridin-4-one (Compound P38) was prepared using Compound P20 and benzyloxyammonium chloride and was isolated as a white solid (0.040 g, 31%).

Example 59

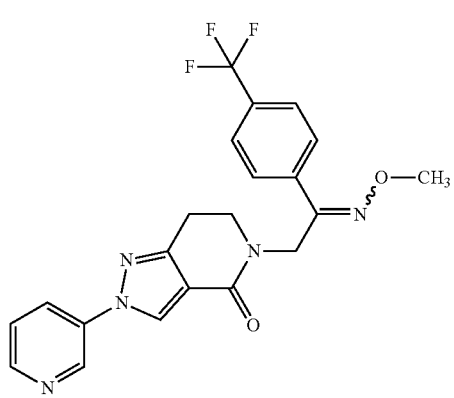
P35

Using the procedure disclosed in Example 45, 5-(2-(methoxyimino)-2-(4-(trifluoromethyl)phenyl)ethyl)-2-(pyridin-3-yl)-2,5,6,7-tetrahydro-4H-pyrazolo[4,3-c]pyridin-4-one (Compound P38) was prepared using Compound P21 and methyloxyammonium chloride and was isolated as a yellow solid (0.030 g, 28%).

Example 60

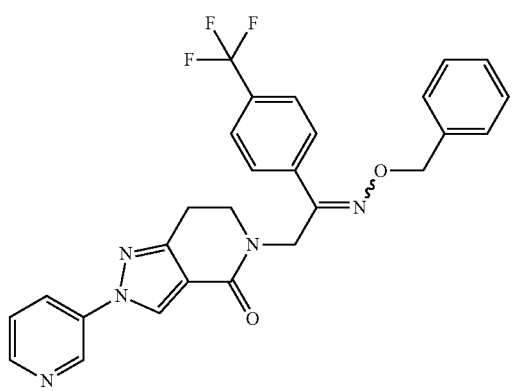
P39

Using the procedure disclosed in Example 45, 5-(2-((benzyloxy)imino)-2-(4-(trifluoromethyl)phenyl)ethyl)-2-(pyridin-3-yl)-2,5,6,7-tetrahydro-4H-pyrazolo[4,3-c]pyridin-4-one (Compound P39) was prepared using Compound P21 and benzyloxyammonium chloride and was isolated as a white solid (0.036 g, 28%).

TABLE 4 shows non-limiting examples of the pyrazolo[3,4-c]piperidin-2-one or pyrazole[3,4-c]piperidin-2-thionecompounds of formula I.

| Compound | Structure | May be Prepared according to Example or Scheme: |
|---|---|---|
| P1 | 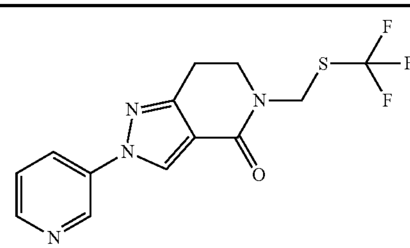 | Example 10 |
| P2 | 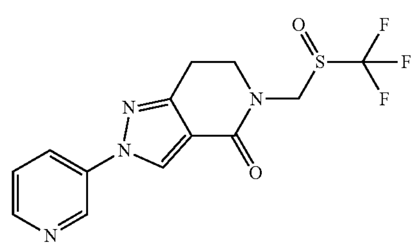 [SMILES: O=C1c2cn(-c3cccnc3)nc2CCN1CS(=O)C(F)(F)F] | Example 43 |
| P3 | 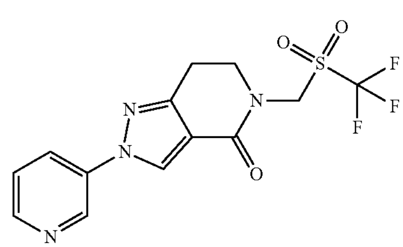 [SMILES: O=C1c2cn(-c3cccnc3)nc2CCN1CS(=O)(=O)C(F)(F)F] | Example 43 |

-continued

| Compound | Structure | May be Prepared according to Example or Scheme: |
|---|---|---|
| P4 | 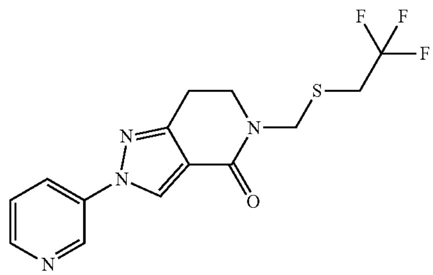 [SMILES: O=C1c2cn(-c3cccnc3)nc2CCN1CSCC(F)(F)F] | Example 41 |
| P5 | 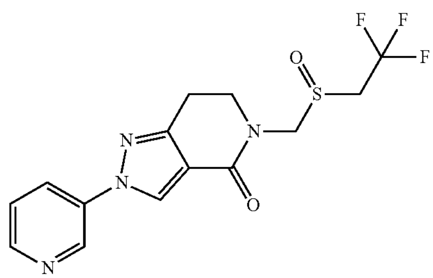 [SMILES: O=C1c2cn(-c3cccnc3)nc2CCN1CS(=O)CC(F)(F)F] | Example 43 |
| P6 | 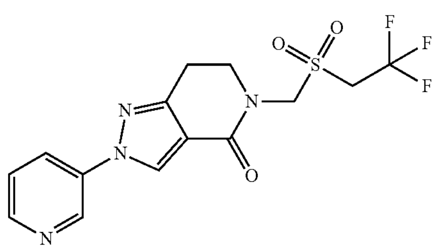 [SMILES: O=C1c2cn(-c3cccnc3)nc2CCN1CS(=O)(=O)CC(F)(F)F] | Example 43 |
| P7 | 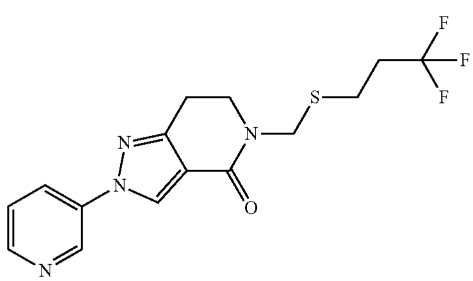 [SMILES: O=C1c2cn(-c3cccnc3)nc2CCN1CSCCC(F)(F)F] | Example 41 |
| P8 | 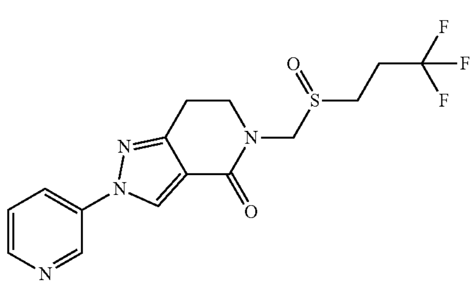 [SMILES: O=C1c2cn(-c3cccnc3)nc2CCN1CS(=O)CCC(F)(F)F] | Example 43 |

-continued

| Compound | Structure | May be Prepared according to Example or Scheme: |
|---|---|---|
| P9 | 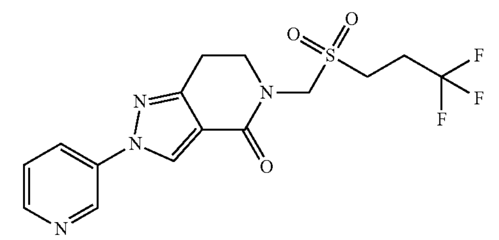 [SMILES: O=C1c2cn(-c3cccnc3)nc2CCN1CS(=O)(=O)CCC(F)(F)F] | Example 43 |
| P10 | 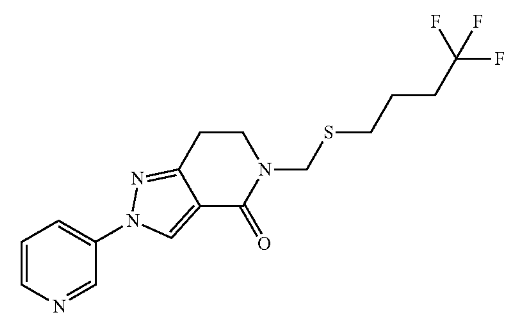 [SMILES: O=C1c2cn(-c3cccnc3)nc2CCN1CSCCCC(F)(F)F] | Example 41 |
| P11 | 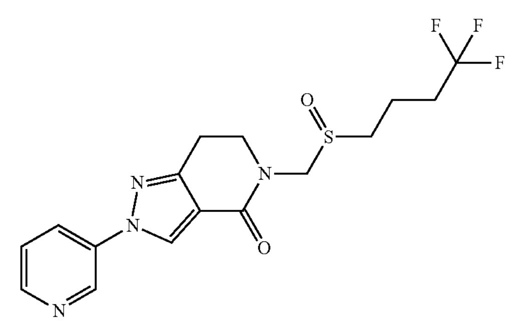 [SMILES: O=C1c2cn(-c3cccnc3)nc2CCN1CS(=O)CCCC(F)(F)F] | Example 43 |
| P12 | 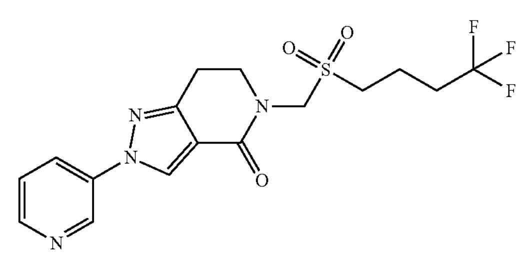 [SMILES: O=C1c2cn(-c3cccnc3)nc2CCN1CS(=O)(=O)CCCC(F)(F)F] | Example 43 |
| P13 | 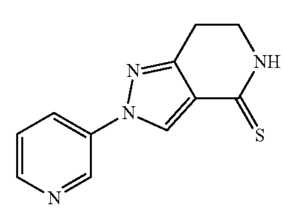 | Scheme 13 |

-continued
| Compound | Structure | May be Prepared according to Example or Scheme: |
|---|---|---|
| P14 | 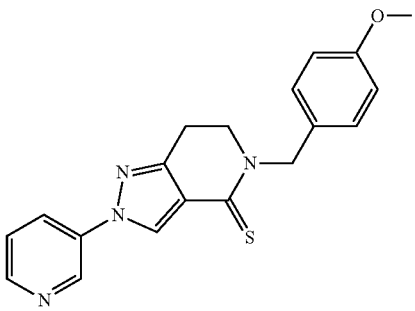 | Scheme 13 |
| P15 | 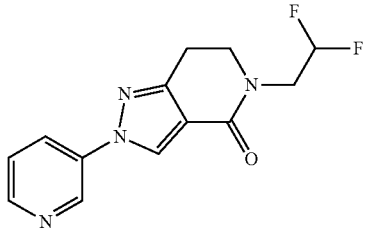 [SMILES: O=C1c2cn(-c3cccnc3)nc2CCN1CC(F)F] | Schemes 11A, 11B, or 11C |
| P16 | 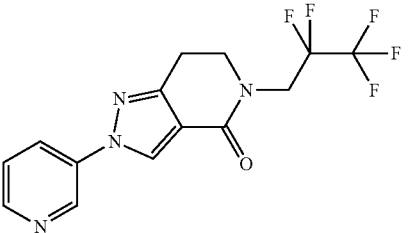 [SMILES: O=C1c2cn(-c3cccnc3)nc2CCN1CC(F)(F)C(F)(F)F] | Schemes 11A, 11B, or 11C |
| P17 | 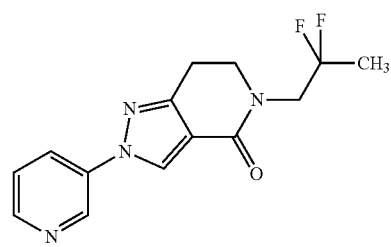 [SMILES: CC(F)(F)CN1CCc2nn(-c3cccnc3)cc2C1=O] | Schemes 11A, 11B, or 11C |
| P18 | 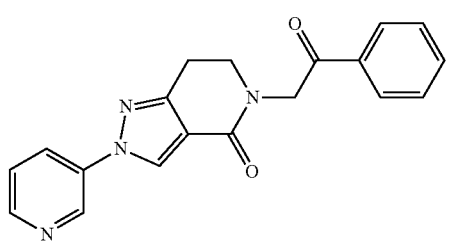 [SMILES: O=C(CN1CCc2nn(-c3cccnc3)cc2C1=O)c1ccccc1] | Schemes 11A, 11B, or 11C |

-continued

| Compound | Structure | May be Prepared according to Example or Scheme: |
|---|---|---|
| P19 | 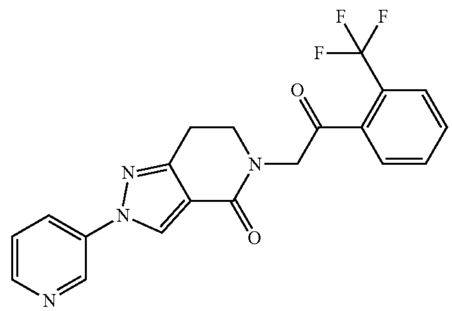 [SMILES: O=C(CN1CCc2nn(-c3cccnc3)cc2C1=O)c1ccccc1C(F)(F)F] | Schemes 11A, 11B, or 11C |
| P20 | 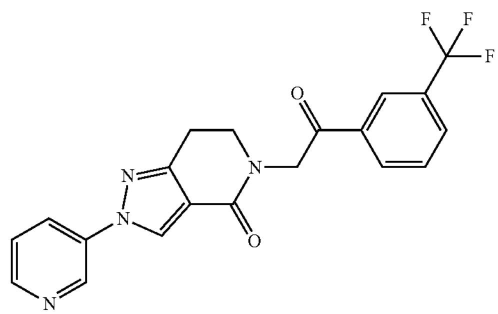 [SMILES: O=C(CN1CCc2nn(-c3cccnc3)cc2C1=O)c1cccc(C(F)(F)F)c1] | Schemes 11A, 11B, or 11C |
| P21 | 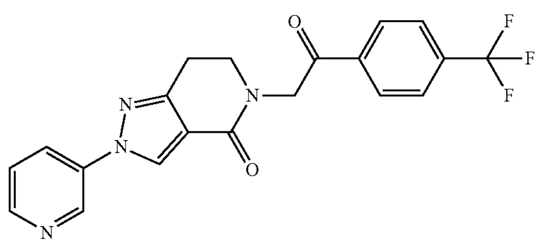 [SMILES: O=C(CN1CCc2nn(-c3cccnc3)cc2C1=O)c1ccc(C(F)(F)F)cc1] | Schemes 11A, 11B, or 11C |
| P22 | 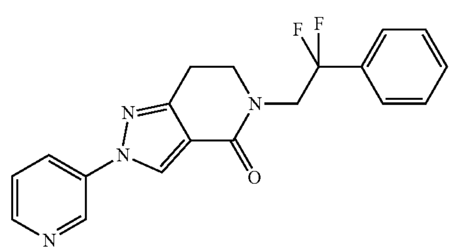 [SMILES: O=C1c2cn(-c3cccnc3)nc2CCN1CC(F)(F)c1ccccc1] | Schemes 11A, 11B, or 11C |
| P23 | 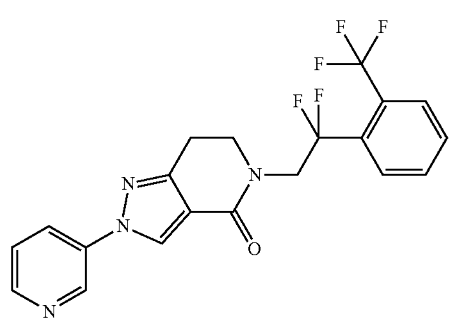 [SMILES: O=C1c2cn(-c3cccnc3)nc2CCN1CC(F)(F)c1ccccc1C(F)(F)F] | Schemes 11A, 11B, or 11C |

-continued

| Compound | Structure | May be Prepared according to Example or Scheme: |
|---|---|---|
| P24 | 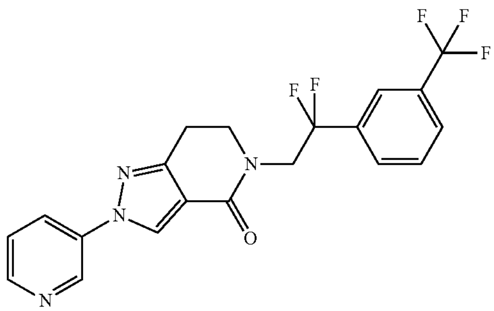 [SMILES: O=C1c2cn(-c3cccnc3)nc2CCN1CC(F)(F)c1cccc(C(F)(F)F)c1] | Schemes 11A, 11B, or 11C |
| P25 | 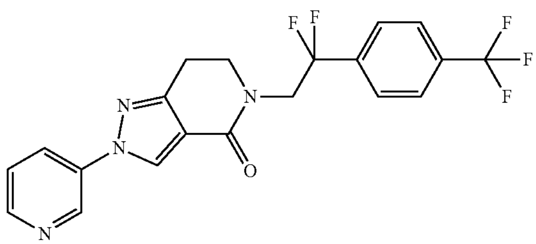 [SMILES: O=C1c2cn(-c3cccnc3)nc2CCN1CC(F)(F)c1ccc(C(F)(F)F)cc1] | Schemes 11A, 11B, or 11C |
| P26 | 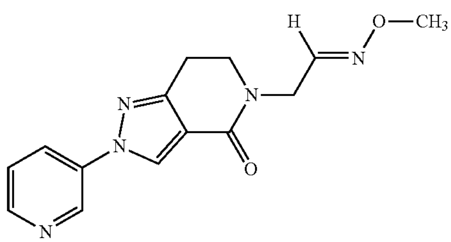 [SMILES: CO/N=C/CN1CCc2nn(-c3cccnc3)cc2C1=O] | Schemes 12A, 12B, 12C, or 12D |
| P27 | 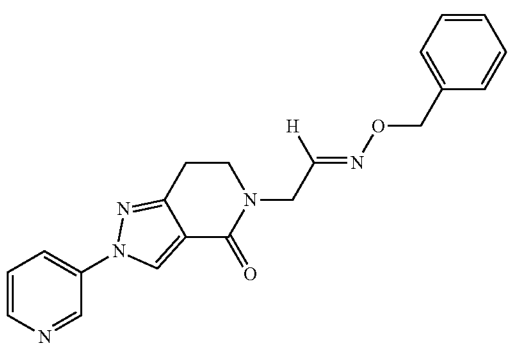 [SMILES: O=C1c2cn(-c3cccnc3)nc2CCN1C/C=N/OCc1ccccc1] | Schemes 12A, 12B, 12C, or 12D |
| P28 | 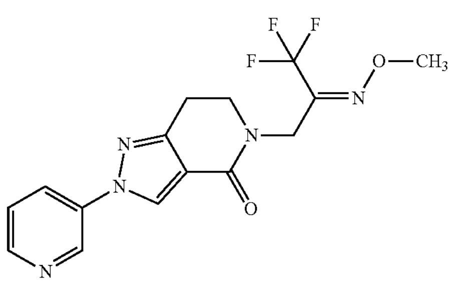 [SMILES: CO/N=C(/CN1CCc2nn(-c3cccnc3)cc2C1=O)C(F)(F)F] | Schemes 12A, 12B, 12C, or 12D |

-continued

| Compound | Structure | May be Prepared according to Example or Scheme: |
|---|---|---|
| P29 | 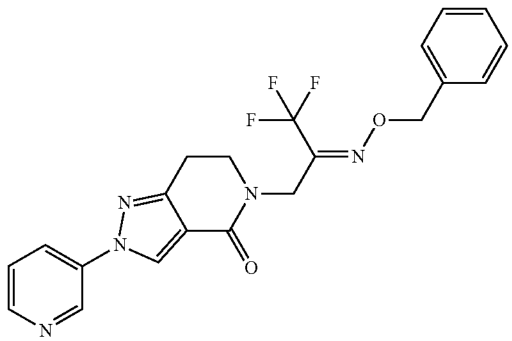 [SMILES: O=C1c2cn(-c3cccnc3)nc2CCN1C/C(=N/OCc1ccccc1)C(F)(F)F] | Schemes 12A, 12B, 12C, or 12D |
| P30 | 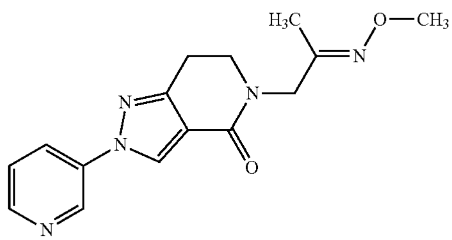 | Schemes 12A, 12B, 12C, or 12D |
| P31 | 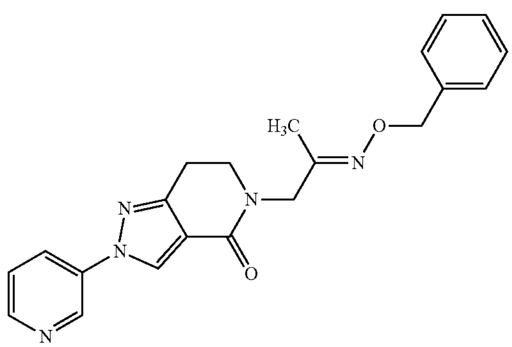 [SMILES: C/C(CN1CCc2nn(-c3cccnc3)cc2C1=O)=N\OCc1ccccc1] | Schemes 12A, 12B, 12C, or 12D |
| P32 | 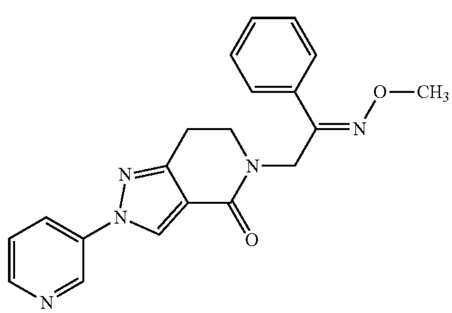 [SMILES: CO/N=C(/CN1CCc2nn(-c3cccnc3)cc2C1=O)c1ccccc1] | Schemes 12A, 12B, 12C, or 12D |

-continued

| Compound | Structure | May be Prepared according to Example or Scheme: |
|---|---|---|
| P33 | 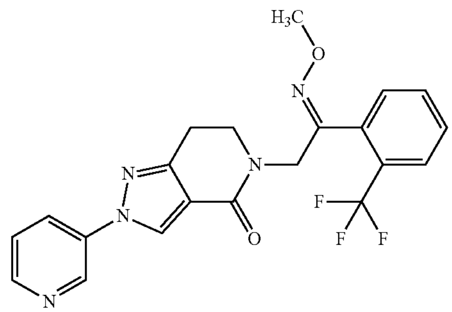 [SMILES: CO/N=C(/CN1CCc2nn(-c3cccnc3)cc2C1=O)c1ccccc1C(F)(F)F] | Schemes 12A, 12B, 12C, or 12D |
| P34 | 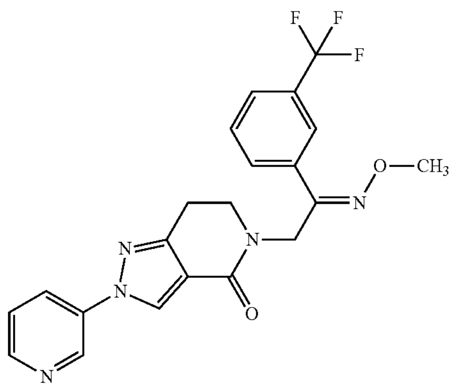 [SMILES: CO/N=C(/CN1CCc2nn(-c3cccnc3)cc2C1=O)c1cccc(C(F)(F)F)c1] | Schemes 12A, 12B, 12C, or 12D |
| P35 | 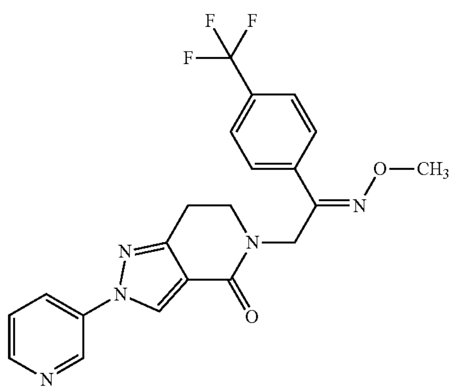 [SMILES: CO/N=C(/CN1CCc2nn(-c3cccnc3)cc2C1=O)c1ccc(C(F)(F)F)cc1] | Schemes 12A, 12B, 12C, or 12D |
| P36 | 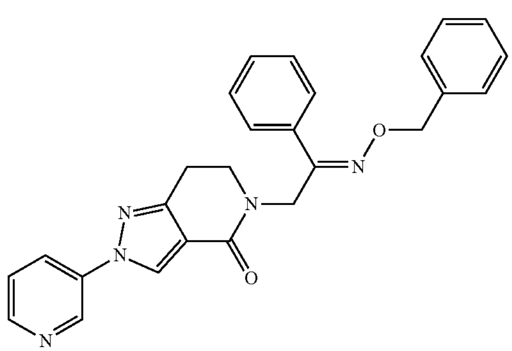 [SMILES: O=C1c2cn(-c3cccnc3)nc2CCN1C/C(=N/OCc1ccccc1)c1ccccc1] | Schemes 12A, 12B, 12C, or 12D |

-continued

| Compound | Structure | May be Prepared according to Example or Scheme: |
|---|---|---|
| P37 | 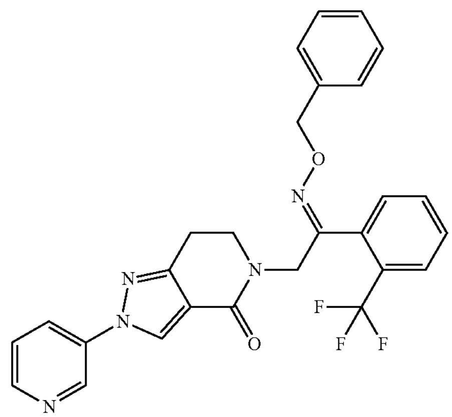 [SMILES: O=C1c2cn(-c3cccnc3)nc2CCN1C/C(=N/OCc1ccccc1)c1ccccc1C(F)(F)F] | Schemes 12A, 12B, 12C, or 12D |
| P38 | 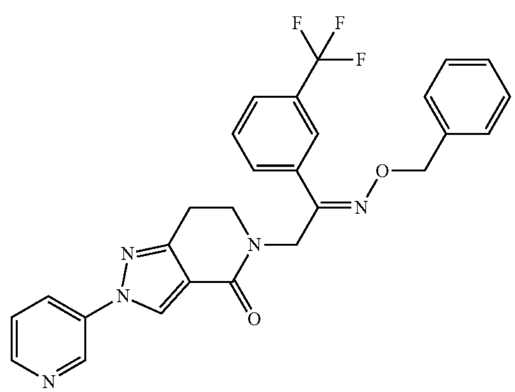 [SMILES: O=C1c2cn(-c3cccnc3)nc2CCN1C/C(=N/OCc1ccccc1)c1cccc(C(F)(F)F)c1] | Schemes 12A, 12B, 12C, or 12D |
| P39 | 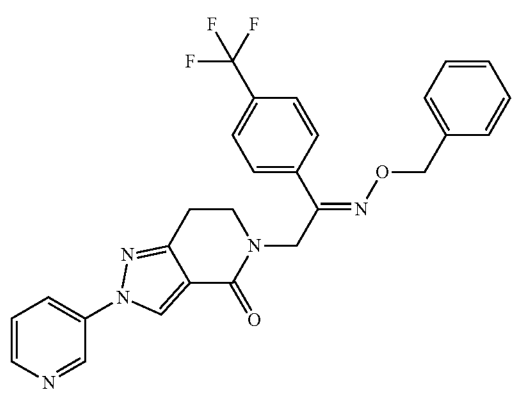 [SMILES: O=C1c2cn(-c3cccnc3)nc2CCN1C/C(=N/OCc1ccccc1)c1ccc(C(F)(F)F)cc1] | Schemes 12A, 12B, 12C, or 12D |

TABLE 5 shows further non-limiting examples of the the pyrazolo[3,4-c]piperidin-2-one compounds of formula I.

| Compound | Structure | Prepared according to Example: |
|---|---|---|
| F1 | 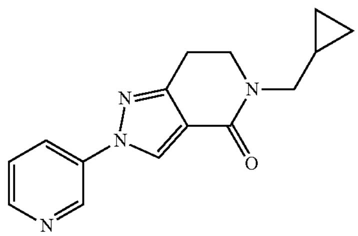 [SMILES: O=C1c2cn(-c3cccnc3)nc2CCN1CC1CC1] | 7 |
| F2 | 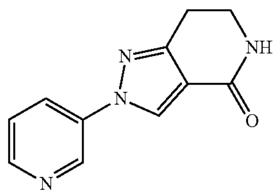 [SMILES: O=C1NCCc2nn(-c3cccnc3)cc21] | 1 |
| F3 | 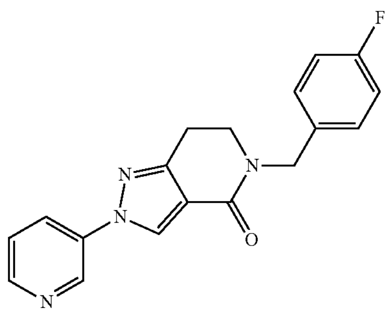 [SMILES: O=C1c2cn(-c3cccnc3)nc2CCN1Cc1ccc(F)cc1] | 17 |
| F4 | 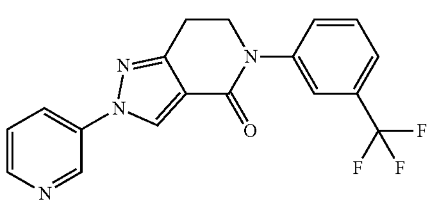 [SMILES: O=C1c2cn(-c3cccnc3)nc2CCN1c1cccc(C(F)(F)F)c1] | 23 |
| F5 | 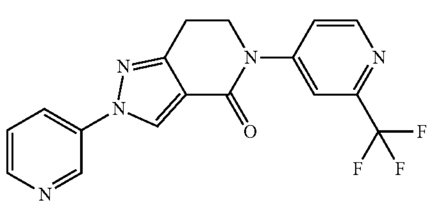 [SMILES: O=C1c2cn(-c3cccnc3)nc2CCN1c1ccnc(C(F)(F)F)c1] | 23 |
| F6 | 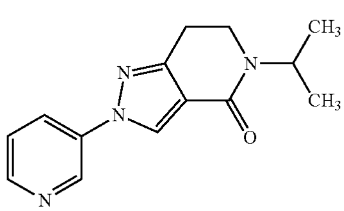 [SMILES: CC(C)N1CCc2nn(-c3cccnc3)cc2C1=O] | 7 |

-continued

| Compound | Structure | Prepared according to Example: |
|---|---|---|
| F7 | 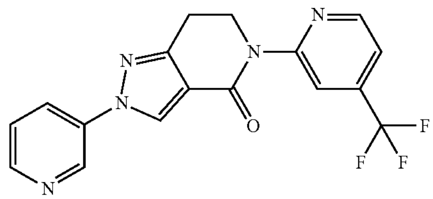 [SMILES: O=C1c2cn(-c3cccnc3)nc2CCN1c1cc(C(F)(F)F)ccn1] | 23 |
| F8 | 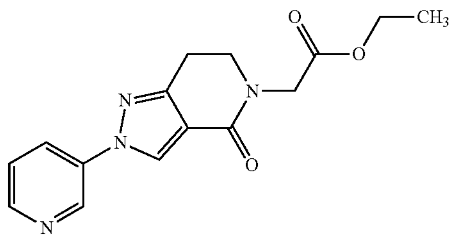 [SMILES: CCOC(=O)CN1CCc2nn(-c3cccnc3)cc2C1=O] | 20 |
| F10 | 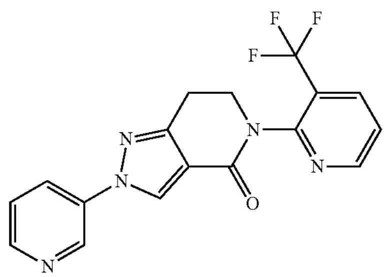 [SMILES: O=C1c2cn(-c3cccnc3)nc2CCN1c1ncccc1C(F)(F)F] | 23 |
| F12 | 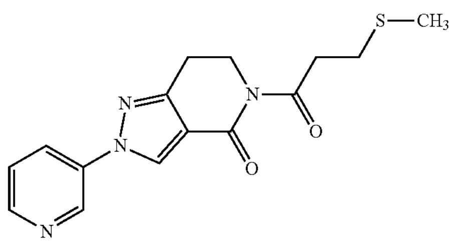 [SMILES: CSCCC(=O)N1CCc2nn(-c3cccnc3)cc2C1=O] | 21 |
| F13 | 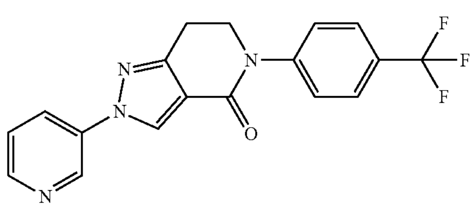 | 23 |
| F14 | 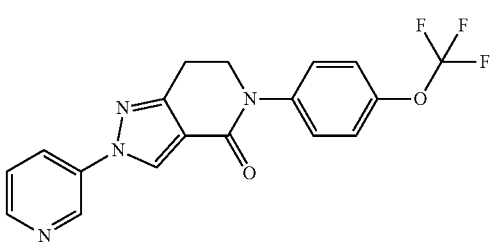 [SMILES: O=C1c2cn(-c3cccnc3)nc2CCN1c1ccc(OC(F)(F)F)cc1] | 23 |

-continued

| Compound | Structure | Prepared according to Example: |
|---|---|---|
| F15 | 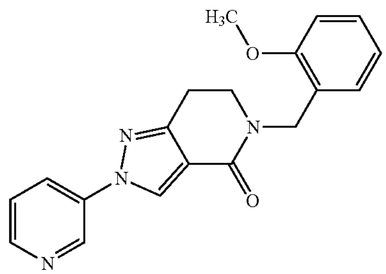 [SMILES: COc1ccccc1CN1CCc2nn(-c3cccnc3)cc2C1=O] | 17 |
| F17 | 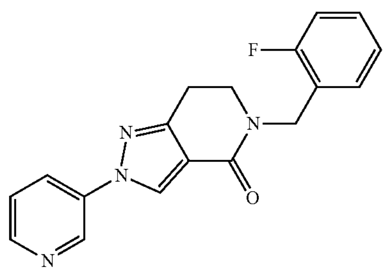 [SMILES: O=C1c2cn(-c3cccnc3)nc2CCN1Cc1ccccc1F] | 13 |
| F18 | 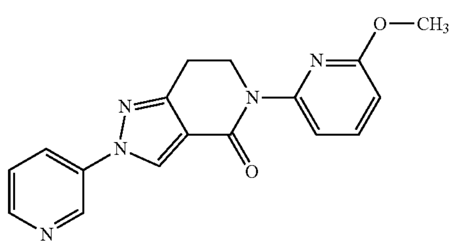 [SMILES: COc1cccc(N2CCc3nn(-c4cccnc4)cc3C2=O)n1] | 23 |
| F19 | 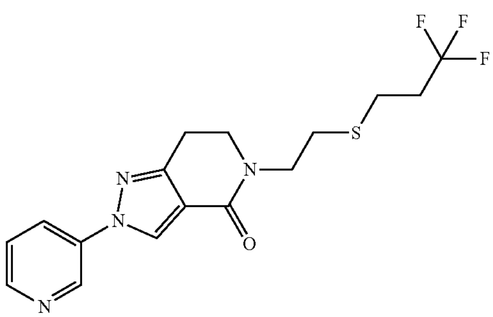 [SMILES: O=C1c2cn(-c3cccnc3)nc2CCN1CCSCCC(F)(F)F] | 41 |
| F20 | 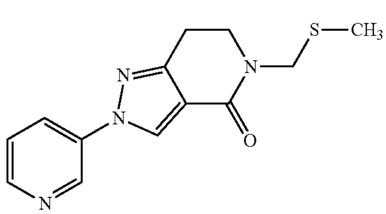 [SMILES: CSCN1CCc2nn(-c3cccnc3)cc2C1=O] | 10 |

-continued

| Compound | Structure | Prepared according to Example: |
|---|---|---|
| F21 | 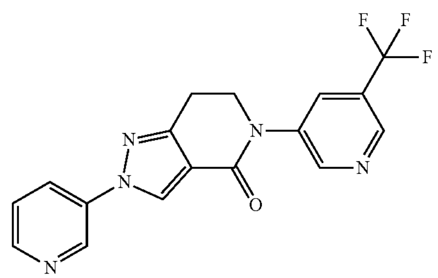 [SMILES: O=C1c2cn(-c3cccnc3)nc2CCN1c1cncc(C(F)(F)F)c1] | 23 |
| F22 | 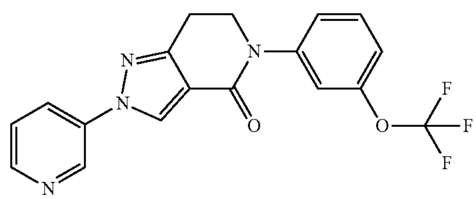 [SMILES: O=C1c2cn(-c3cccnc3)nc2CCN1c1cccc(OC(F)(F)F)c1] | 23 |
| F23 | 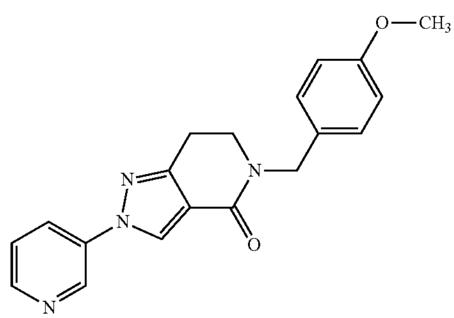 [SMILES: COc1ccc(CN2CCc3nn(-c4cccnc4)cc3C2=O)cc1] | 13 |
| F27 | 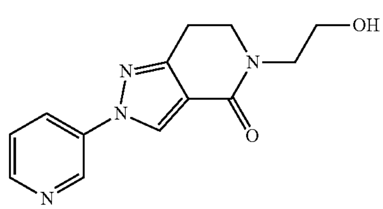 [SMILES: O=C1c2cn(-c3cccnc3)nc2CCN1CCO] | 39 |
| F28 | 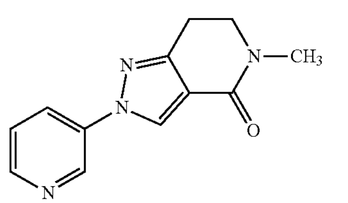 [SMILES: CN1CCc2nn(-c3cccnc3)cc2C1=O] | 13 |
| F29 | 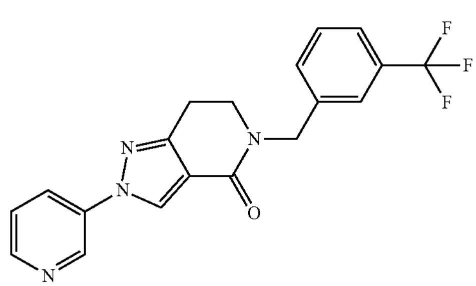 [SMILES: O=C1c2cn(-c3cccnc3)nc2CCN1Cc1cccc(C(F)(F)F)c1] | 13 |

-continued

| Compound | Structure | Prepared according to Example: |
|---|---|---|
| F30 | 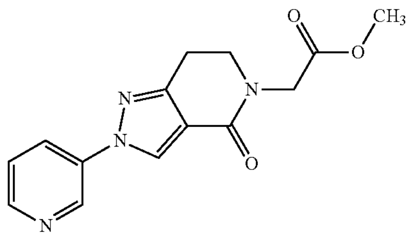 [SMILES: COC(=O)CN1CCc2nn(-c3cccnc3)cc2C1=O] | 10 |
| F31 | 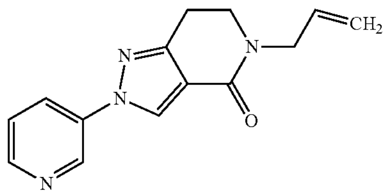 [SMILES: C=CCN1CCc2nn(-c3cccnc3)cc2C1=O] | 10 |
| F32 | 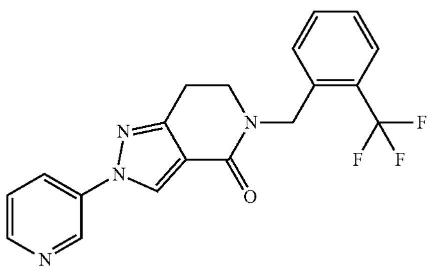 [SMILES: O=C1c2cn(-c3cccnc3)nc2CCN1Cc1ccccc1C(F)(F)F] | 13 |
| F33 | 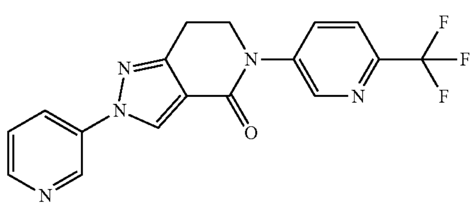 | 23 |
| F34 | 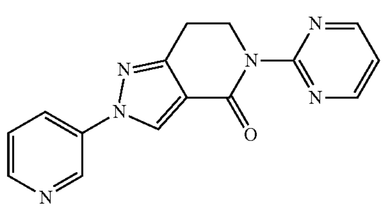 [SMILES: O=C1c2cn(-c3cccnc3)nc2CCN1c1ncccn1] | 23 |
| F37 | 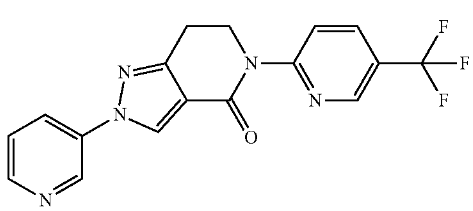 | 23 |
| F38 | 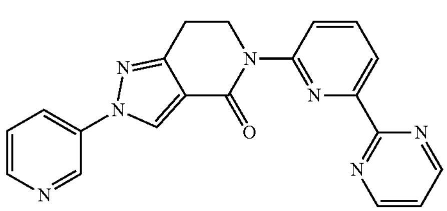 [SMILES: O=C1c2cn(-c3cccnc3)nc2CCN1c1cccc(-c2ncccn2)n1] | 23 |

-continued

| Compound | Structure | Prepared according to Example: |
|---|---|---|
| F39 | 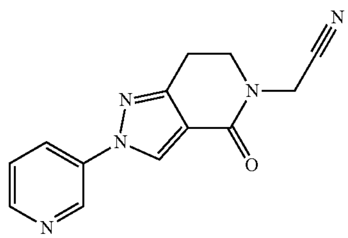 [SMILES: N#CCN1CCc2nn(-c3cccnc3)cc2C1=O] | 5 |
| F40 | 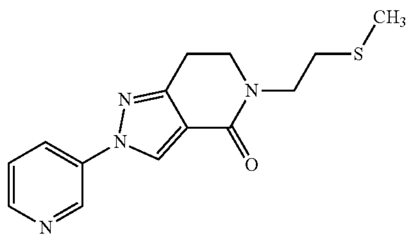 [SMILES: CSCCN1CCc2nn(-c3cccnc3)cc2C1=O] | 42 |
| F42 | 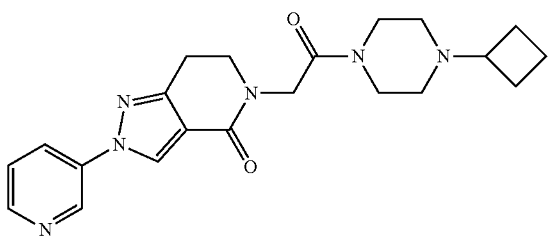 [SMILES: O=C(CN1CCc2nn(-c3cccnc3)cc2C1=O)N1CCN(C2CCC2)CC1] | 7 |
| F43 | 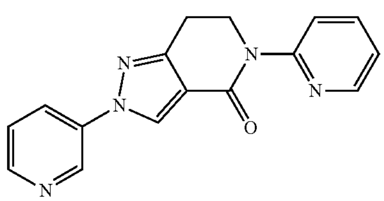 [SMILES: O=C1c2cn(-c3cccnc3)nc2CCN1c1ccccn1] | 22 |
| F46 | 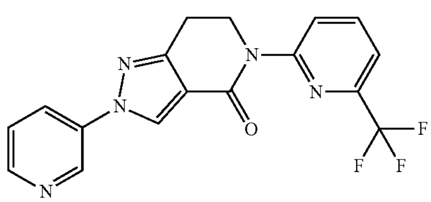 [SMILES: O=C1c2cn(-c3cccnc3)nc2CCN1c1cccc(C(F)(F)F)n1] | 23 |
| F48 | 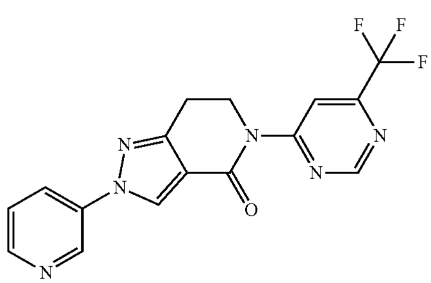 [SMILES: O=C1c2cn(-c3cccnc3)nc2CCN1c1cc(C(F)(F)F)ncn1] | 23 |

-continued

| Compound | Structure | Prepared according to Example: |
|---|---|---|
| F49 | 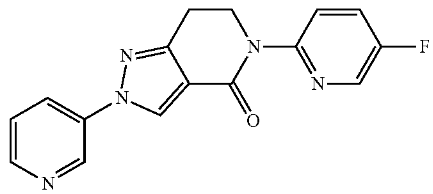 [SMILES: O=C1c2cn(-c3cccnc3)nc2CCN1c1ccc(F)cn1] | 23 |
| F50 | 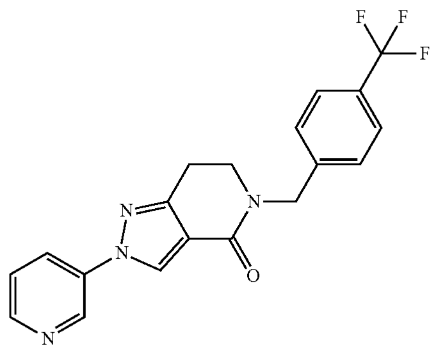 [SMILES: O=C1c2cn(-c3cccnc3)nc2CCN1Cc1ccc(C(F)(F)F)cc1] | 17 |
| F51 | 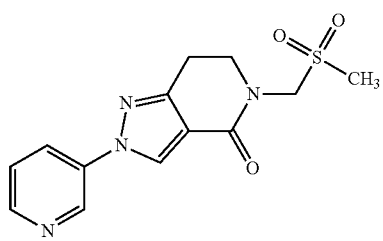 [SMILES: CS(=O)(=O)CN1CCc2nn(-c3cccnc3)cc2C1=O] | 43 |
| F54 | 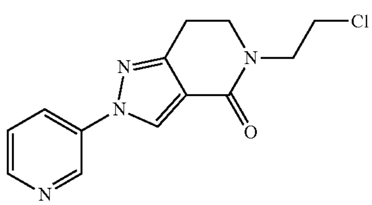 [SMILES: O=C1c2cn(-c3cccnc3)nc2CCN1CCCl] | 40 |
| P18 | 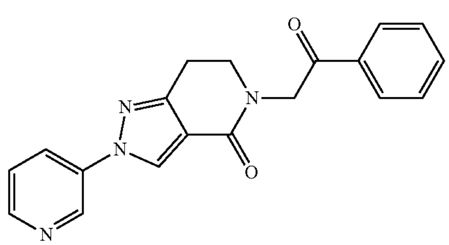 [SMILES: O=C(CN1CCc2nn(-c3cccnc3)cc2C1=O)c1ccccc1] | 49 |
| P20 | 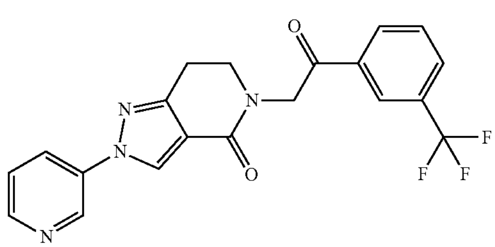 [SMILES: O=C(CN1CCc2nn(-c3cccnc3)cc2C1=O)c1cccc(C(F)(F)F)c1] | 49 |

-continued

| Compound | Structure | Prepared according to Example: |
|---|---|---|
| P21 | 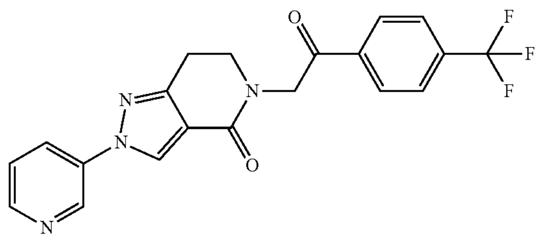 [SMILES: O=C(CN1CCc2nn(-c3cccnc3)cc2C1=O)c1ccc(C(F)(F)F)cc1] | 49 |
| P26 | 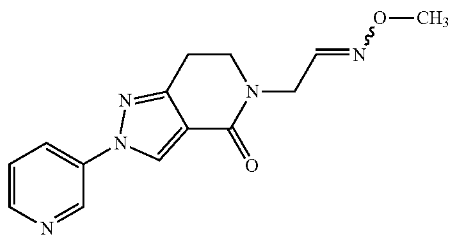 [SMILES: CON=CCN1CCc2nn(-c3cccnc3)cc2C1=O] | 45 |
| P27 | 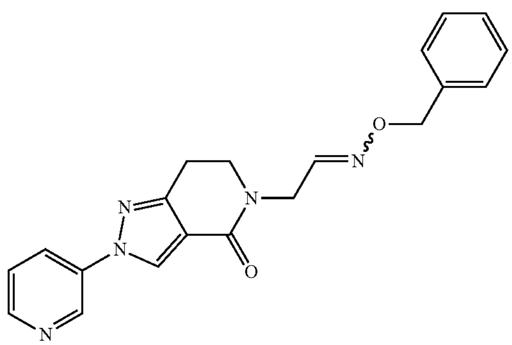 [SMILES: O=C1c2cn(-c3cccnc3)nc2CCN1CC=NOCc1ccccc1] | 45 |
| P30 | 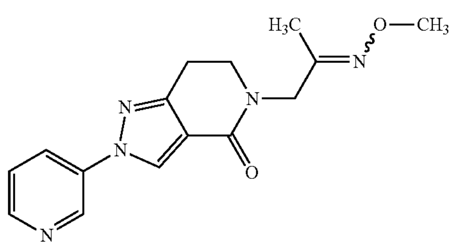 [SMILES: CON=C(C)CN1CCc2nn(-c3cccnc3)cc2C1=O] | 45 |
| P31 | 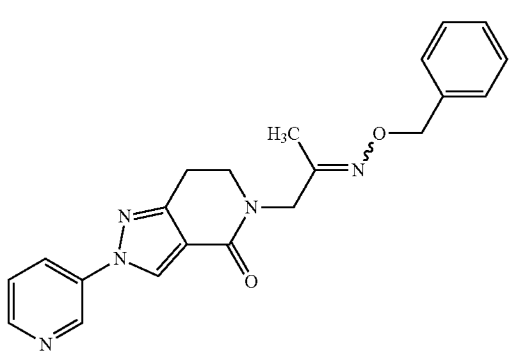 | 45 |

-continued

| Compound | Structure | Prepared according to Example: |
|---|---|---|
| P32 | 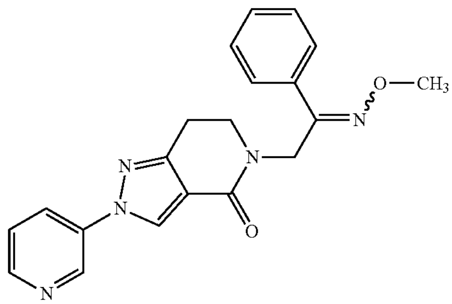 [SMILES: CON=C(CN1CCc2nn(-c3cccnc3)cc2C1=O)c1ccccc1] | 45 |
| P34 | 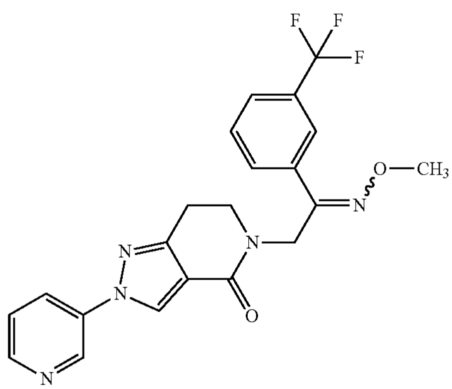 [SMILES: CON=C(CN1CCc2nn(-c3cccnc3)cc2C1=O)c1cccc(C(F)(F)F)c1] | 45 |
| P35 | 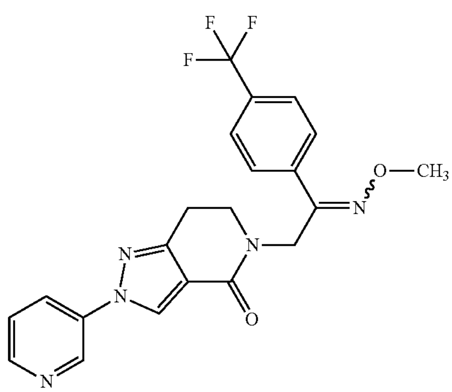 [SMILES: CON=C(CN1CCc2nn(-c3cccnc3)cc2C1=O)c1ccc(C(F)(F)F)cc1] | 45 |
| P36 | 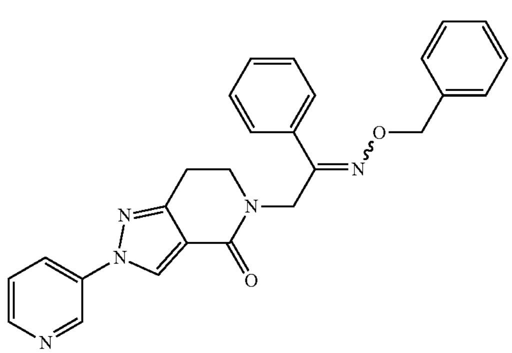 [SMILES: O=C1c2cn(-c3cccnc3)nc2CCN1CC(=NOCc1ccccc1)c1ccccc1] | 45 |

| Compound | Structure | Prepared according to Example: |
|---|---|---|
| P38 | *3-(trifluoromethyl)phenyl pyrazolopiperidinone with benzyloxyimino, pyridin-3-yl* | 45 |
| P39 | *4-(trifluoromethyl)phenyl pyrazolopiperidinone with benzyloxyimino, pyridin-3-yl* | 45 |

TABLE 6 shows analytical data for the pyrazolo[3,4-c]piperidin-2-one compounds in TABLE 5.

| Compound | Mp (° C.) | Mass ESIMS (m/z) | NMR, IR (thin film) |
|---|---|---|---|
| F1 | 160-162 | 270 ([M + 2]+) | $^1$H NMR (400 MHz, CDCl$_3$) δ 9.08 (s, 1H), 8.52 (s, 1H), 8.38-8.43 (m, 1H), 8.12 (d, J = 7.48 Hz, 1H), 7.53 (dd, J = 4.92, 8.24 Hz, 1H), 3.79 (t, J = 6.76 Hz, 2H), 3.47 (d, J = 6.92 Hz, 2H), 3.10 (t, J = 6.72 Hz, 2H), 1.01-1.15 (m, 1H), 0.55-0.60 (m, 2H), 0.32-0.36 (m, 2H) |
| F2 | 167-171 | 215 ([M + H]+) | $^1$H NMR (300 MHz, CDCl$_3$) δ 9.00 (d, J = 2.6 Hz, 1H), 8.59 (dd, J = 4.8, 1.4 Hz, 1H), 8.43 (s, 1H), 8.02 (ddd, J = 8.3, 2.6, 1.4 Hz, 1H), 7.42 (dd, J = 8.3, 4.8 Hz, 1H), 6.51 (s, 1H), 3.66 (td, J = 6.7, 2.7 Hz, 2H), 3.03 (t, J = 6.7 Hz, 2H) |
| F3 | | 323 ([M + H]+) | $^1$H NMR (400 MHz, CDCl$_3$) δ 9.01 (d, J = 2.0 Hz, 1H), 8.60 (d, J = 3.8 Hz, 1H), 8.41 (s, 1H), 8.01 (ddd, J = 8.3, 2.5, 1.5 Hz, 1H), 7.44 (dd, J = 8.3, 4.8 Hz, 1H), 7.36-7.28 (m, 2H), 7.03 (t, J = 8.6 Hz, 2H), 4.73 (s, 2H), 3.57 (t, J = 6.8 Hz, 2H), 3.01 (t, J = 6.7 Hz, 2H) IR (cm$^{-1}$): 1642, 1602 |
| F4 | | 359 ([M + H]+) | $^1$H NMR (400 MHz, CDCl$_3$) δ 9.09-9.01 (m, 1H), 8.62 (dd, J = 4.8, 1.4 Hz, 1H), 8.48 (s, 1H), 8.05 (ddd, J = 8.3, 2.7, 1.5 Hz, 1H), 7.62 (s, 1H), 7.61-7.51 (m, 3H), 7.45 (ddd, J = 8.3, 4.8, 0.7 Hz, 1H), 4.13 (t, J = |

-continued

| Compound | Mp (° C.) | Mass ESIMS (m/z) | NMR, IR (thin film) |
|---|---|---|---|
| | | | 6.6 Hz, 2H), 3.24 (t, J = 6.5 Hz, 2H) IR (cm$^{-1}$): 3096, 1657 |
| F5 | | 360 ([M + H]$^+$) | $^1$H NMR (400 MHz, CDCl$_3$) δ 9.05 (d, J = 2.3 Hz, 1H), 8.72 (d, J = 5.5 Hz, 1H), 8.64 (dd, J = 4.8, 1.4 Hz, 1H), 8.54 (s, 1H), 8.06 (ddd, J = 8.3, 2.7, 1.5 Hz, 1H), 7.77 (d, J = 2.0 Hz, 1H), 7.56 (dd, J = 5.5, 2.1 Hz, 1H), 7.46 (ddd, J = 8.3, 4.8, 0.6 Hz, 1H), 4.21 (t, J = 6.5 Hz, 2H), 3.26 (t, J = 6.5 Hz, 2H) IR (cm$^{-1}$): 3077, 1678, 1564 |
| F6 | 168-171 | 257 ([M + H]$^+$) | $^1$H NMR (300 MHz, MeOD) δ 9.07 (d, J = 2.37 Hz, 1H), 8.66 (s, 1H), 8.53 (d, J = 3.78 Hz, 1H), 8.27-0.00 (m, 1H), 7.57 (dd, J = 4.74, 8.45 Hz, 1H), 4.95-0.00 (m, 1H), 3.62 (t, J = 6.75 Hz, 2H), 3.00 (t, J = 6.57 Hz, 2H), 1.23 (d, J = 6.84 Hz, 6H) |
| F7 | 177-179 | 360 ([M + H]$^+$) | $^1$H NMR (300 MHz, CDCl$_3$) δ 9.04 (d, J = 2.6 Hz, 1H), 8.62 (dd, J = 4.8, 1.4 Hz, 1H), 8.58 (d, J = 4.9 Hz, 1H), 8.49 (s, 1H), 8.28-8.21 (m, 1H), 8.05 (ddd, J = 8.3, 2.6, 1.3 Hz, 1H), 7.45 (dd, J = 8.3, 4.7 Hz, 1H), 7.30-7.26 (m, 1H), 4.48 (t, J = 6.5 Hz, 2H), 3.18 (t, J = 6.5 Hz, 2H) |
| F8 | | 301 ([M + H]$^+$) | $^1$H NMR (400 MHz, CDCl$_3$) δ 9.00 (d, J = 2.1 Hz, 1H), 8.60 (dd, J = 4.7, 1.4 Hz, 1H), 8.38 (s, 1H), 8.01 (ddd, J = 8.3, 2.6, 1.4 Hz, 1H), 7.43 (ddd, J = 8.3, 4.8, 0.8 Hz, 1H), 4.31 (s, 2H), 4.23 (q, J = 7.2 Hz, 2H), 3.76 (t, J = 6.7 Hz, 2H), 3.13 (t, J = 6.7 Hz, 2H), 1.30 (t, J = 7.2 Hz, 3H) $^{13}$C NMR (101 MHz, CDCl$_3$) δ 169.25, 162.29, 153.77, 148.39, 140.96, 136.03, 127.85, 126.75, 124.00, 116.00, 61.36, 48.45, 48.28, 22.73, 14.21 |
| F10 | | 360 ([M + H]$^+$) | $^1$H NMR (300 MHz, CDCl$_3$) δ 9.03 (d, J = 2.6 Hz, 1H), 8.77 (dd, J = 4.9, 1.5 Hz, 1H), 8.61 (dd, J = 4.8, 1.4 Hz, 1H), 8.46 (s, 1H), 8.12 (dd, J = 7.9, 1.7 Hz, 1H), 8.04 (ddd, J = 8.3, 2.6, 1.5 Hz, 1H), 7.45 (td, J = 8.8, 4.8 Hz, 2H), 4.30 (td, J = 12.4, 4.8 Hz, 1H), 3.80 (ddd, J = 12.2, 5.8, 3.1 Hz, 1H), 3.31 (ddd, J = 16.3, 12.4, 5.9 Hz, 1H), 3.16 (ddd, J = 16.1, 4.6, 3.4 Hz, 1H) IR (cm$^{-1}$): 1667, 1567 |
| F12 | | 317 ([M + H]$^+$) | $^1$H NMR (400 MHz, CDCl$_3$) δ 9.02 (d, J = 2.3 Hz, 1H), 8.65 (dd, J = 4.8, 1.4 Hz, 1H), 8.51 (s, 1H), 8.06 (ddd, J = 8.3, 2.7, 1.5 Hz, 1H), 7.47 (ddd, J = 8.3, 4.8, 0.6 Hz, 1H), 4.28 (m, 2H), 3.32 (t, J = 7.2 Hz, 2H), 3.05 (m, 2H), 2.88 (t, J = 7.2 Hz, 2H), 2.16 (s, 3H) IR (cm$^{-1}$): 2917, 1690, 1562 |
| F13 | | 359 ([M + H]$^+$) | $^1$H NMR (400 MHz, CDCl$_3$) δ 9.04 (d, J = 2.3 Hz, 1H), 8.63 (dd, J = 4.8, 1.4 Hz, 1H), 8.48 (s, 1H), 8.05 (ddd, J = 8.3, 2.7, 1.5 Hz, 1H), 7.69 (d, J = 8.4 Hz, 2H), 7.50 (d, J = 8.3 Hz, 2H), 7.45 (ddd, J = 8.3, 4.8, 0.7 Hz, 1H), 4.14 (t, J = 6.5 Hz, 2H), 3.23 (t, J = 6.5 Hz, 2H) IR (cm$^{-1}$): 3095, 1666 |
| F14 | | 375 ([M + H]$^+$) | $^1$H NMR (400 MHz, CDCl$_3$) δ 9.08-9.01 (m, 1H), 8.62 (dd, J = 4.8, 1.4 Hz, 1H), 8.48 (s, 1H), 8.05 (ddd, J = 8.3, 2.7, 1.5 Hz, 1H), 7.44 (ddd, J = 8.3, 4.8, 0.7 Hz, 1H), 7.42-7.37 (m, 2H), 7.29 (d, J = 0.8 Hz, 1H), 7.27 (s, 1H), 4.09 (t, J = 6.6 Hz, 2H), 3.22 (t, J = 6.6 Hz, 2H) IR (cm$^{-1}$): 3097, 1650 |
| F15 | | 335 ([M + H]$^+$) | $^1$H NMR (400 MHz, CDCl$_3$) δ 9.01 (d, J = 2.3 Hz, 1H), 8.59 (dd, J = 4.7, 1.1 Hz, 1H), 8.40 (s, 1H), 8.02 (ddd, J = 8.3, 2.7, 1.4 Hz, 1H), 7.43 (dd, J = 8.1, 4.8 Hz, 1H), 7.32 (dd, J = 7.5, 1.6 Hz, 1H), 7.29-7.22 (m, 1H), 6.93 (ddd, J = 12.6, 9.5, 4.4 Hz, 2H), 4.79 (s, 2H), 3.86 (s, 3H), 3.65 (t, J = 6.7 |

-continued

| Compound | Mp (° C.) | Mass ESIMS (m/z) | NMR, IR (thin film) |
|---|---|---|---|
| | | | Hz, 2H), 3.01 (t, J = 6.7 Hz, 2H) IR (cm$^{-1}$): 1642, 1570 |
| F17 | | 323 ([M + H]$^+$) | $^1$H NMR (400 MHz, CDCl$_3$) δ 9.00 (d, J = 2.3 Hz, 1H), 8.60 (dd, J = 4.8, 1.3 Hz, 1H), 8.39 (s, 1H), 8.01 (ddd, J = 8.3, 2.5, 1.5 Hz, 1H), 7.43 (dd, J = 7.8, 5.3 Hz, 2H), 7.31-7.27 (m, 1H), 7.13 (td, J = 7.5, 1.1 Hz, 1H), 7.10-7.04 (m, 1H), 4.82 (s, 2H), 3.66 (t, J = 6.7 Hz, 2H), 3.04 (t, J = 6.7 Hz, 2H) IR (cm$^{-1}$): 1649, 1571 |
| F18 | 226-228 | 322 ([M + H]$^+$) | $^1$H NMR (300 MHz, CDCl$_3$) δ 9.04 (d, J = 2.6 Hz, 1H), 8.61 (dd, J = 4.7, 1.3 Hz, 1H), 8.49 (s, 1H), 8.05 (ddd, J = 8.3, 2.4, 1.4 Hz, 1H), 7.62 (t, J = 7.9 Hz, 1H), 7.50 (d, J = 7.8 Hz, 1H), 7.44 (dd, J = 8.3, 4.7 Hz, 1H), 6.54 (d, J = 7.9 Hz, 1H), 4.44 (t, J = 6.5 Hz, 2H), 3.92 (s, 3H), 3.16 (t, J = 6.5 Hz, 2H) |
| F19 | | 371 ([M + H]$^+$) | $^1$H NMR (400 MHz, CDCl$_3$) δ 9.00 (d, J = 2.3 Hz, 1H), 8.60 (dd, J = 4.8, 1.4 Hz, 1H), 8.36 (s, 1H), 8.01 (ddd, J = 8.3, 2.6, 1.4 Hz, 1H), 7.43 (ddd, J = 8.4, 4.8, 0.7 Hz, 1H), 3.78-3.68 (m, 4H), 3.09 (t, J = 6.7 Hz, 2H), 2.87-2.75 (m, 4H), 2.52-2.35 (m, 2H) $^{19}$F NMR (376 MHz, CDCl$_3$) δ −66.30 (s) |
| F20 | | 275 ([M + H]$^+$) | $^1$H NMR (400 MHz, CDCl$_3$) δ 9.01 (d, J = 2.3 Hz, 1H), 8.61 (dd, J = 4.8, 1.4 Hz, 1H), 8.39 (s, 1H), 8.02 (ddd, J = 8.3, 2.7, 1.5 Hz, 1H), 7.44 (ddd, J = 8.3, 4.8, 0.7 Hz, 1H), 4.72 (s, 2H), 3.79 (t, J = 6.7 Hz, 2H), 3.11 (t, J = 6.7 Hz, 2H), 2.17 (s, 3H) IR (cm$^{-1}$): 2916, 1643, 1569 |
| F21 | | 360 ([M + H]$^+$) | $^1$H NMR (400 MHz, CDCl$_3$) δ 9.05 (d, J = 2.3 Hz, 1H), 8.87 (d, J = 2.4 Hz, 1H), 8.76 (d, J = 0.9 Hz, 1H), 8.64 (dd, J = 4.8, 1.4 Hz, 1H), 8.49 (s, 1H), 8.06 (ddd, J = 8.3, 2.7, 1.5 Hz, 1H), 7.99 (t, J = 1.9 Hz, 1H), 7.47 (ddd, J = 8.3, 4.8, 0.7 Hz, 1H), 4.18 (t, J = 6.5 Hz, 2H), 3.28 (t, J = 6.5 Hz, 2H) IR (cm$^{-1}$): 1667 |
| F22 | 134-136 | 375 ([M + H]$^+$) | $^1$H NMR (300 MHz, CDCl$_3$) δ 9.03 (d, J = 2.6 Hz, 1H), 8.61 (dd, J = 4.7, 1.3 Hz, 1H), 8.47 (s, 1H), 8.04 (ddd, J = 8.3, 2.6, 1.4 Hz, 1H), 7.48-7.40 (m, 2H), 7.32 (ddd, J = 8.2, 1.9, 0.9 Hz, 1H), 7.26-7.23 (m, 1H), 7.16-7.09 (m, 1H), 4.11 (t, J = 6.5 Hz, 2H), 3.22 (t, J = 6.5 Hz, 2H) |
| F23 | | 335 ([M + H]$^+$) | $^1$H NMR (400 MHz, CDCl$_3$) δ 9.00 (d, J = 2.5 Hz, 1H), 8.60 (dd, J = 4.8, 1.5 Hz, 1H), 8.40 (s, 1H), 8.01 (ddd, J = 8.3, 2.8, 1.5 Hz, 1H), 7.47-7.39 (m, 1H), 7.26 (d, J = 8.6 Hz, 2H), 6.88 (d, J = 8.6 Hz, 2H), 4.69 (s, 2H), 3.80 (s, 3H), 3.56 (t, J = 6.7 Hz, 2H), 2.99 (t, J = 6.7 Hz, 2H) IR (cm$^{-1}$): 1641, 1569 |
| F27 | | 259 ([M + H]$^+$) | $^1$H NMR (400 MHz, CDCl$_3$) δ 9.01 (d, J = 2.1 Hz, 1H), 8.60 (dd, J = 4.7, 1.4 Hz, 1H), 8.38 (s, 1H), 8.02 (ddd, J = 8.3, 2.6, 1.5 Hz, 1H), 7.44 (ddd, J = 8.3, 4.8, 0.8 Hz, 1H), 3.89 (dd, J = 10.0, 5.0 Hz, 2H), 3.78 (t, J = 6.7 Hz, 2H), 3.75 (dd, J = 5.6, 4.6 Hz, 2H), 3.10 (t, J = 6.8 Hz, 2H), 2.73 (t, J = 5.0 Hz, 1H) |
| F28 | 167-170 | 229 ([M + H]$^+$) | $^1$H NMR (400 MHz, CDCl$_3$) δ 9.04 (s, 1H), 8.61 (d, J = 4.16 Hz, 1H), 8.40 (s, 1H), 8.06-0.00 (m, 1H), 7.47 (dd, J = 4.76, 8.26 Hz, 1H), 3.68 (t, J = 6.80 Hz, 2H), 3.12 (s, 3H), 3.10 (t, J = 6.76 Hz, 2H) |
| F29 | | 373 ([M + H]$^+$) | $^1$H NMR (400 MHz, CDCl$_3$) δ 9.06 (s, 1H), 8.62 (s, 1H), 8.45 (s, 1H), 8.10 (d, J = 8.6 Hz, 1H), 7.63-7.42 (m, 6H), 4.82 (s, 2H), 3.60 (t, J = 6.7 Hz, 2H), 3.04 (t, J = 6.8 Hz, 2H) IR (cm$^{-1}$): 1647, 1571 |

-continued

| Compound | Mp (° C.) | Mass ESIMS (m/z) | NMR, IR (thin film) |
|---|---|---|---|
| F30 | | 287 ([M + H]+) | ¹H NMR (400 MHz, CDCl₃) δ 9.01 (d, J = 2.4 Hz, 1H), 8.61 (d, J = 3.8 Hz, 1H), 8.38 (s, 1H), 8.02 (ddd, J = 8.3, 2.6, 1.5 Hz, 1H), 7.51-7.36 (m, 1H), 4.33 (s, 2H), 3.80-3.70 (m, 5H), 3.13 (t, J = 6.7 Hz, 2H) ¹³C NMR (101 MHz, CDCl₃) δ 169.73, 162.33, 153.75, 148.40, 140.95, 130.47, 127.89, 126.77, 124.02, 115.94, 52.27, 48.47, 48.17, 22.72 |
| F31 | 142-144 | 255 ([M + H]+) | ¹H NMR (400 MHz, CDCl₃) δ 9.02 (d, J = 2.4 Hz, 1H), 8.59 (dd, J = 4.7, 1.4 Hz, 1H), 8.41 (s, 1H), 8.02 (ddd, J = 8.3, 2.7, 1.5 Hz, 1H), 7.43 (ddd, J = 8.3, 4.8, 0.6 Hz, 1H), 5.85 (ddt, J = 17.1, 10.1, 5.9 Hz, 1H), 5.25 (ddq, J = 10.1, 7.1, 1.4 Hz, 2H), 4.18 (dt, J = 5.9, 1.4 Hz, 2H), 3.62 (t, J = 6.7 Hz, 2H), 3.06 (t, J = 6.7 Hz, 2H) |
| F32 | | 373 ([M + H]+) | ¹H NMR (400 MHz, CDCl₃) δ 9.02 (d, J = 2.5 Hz, 1H), 8.61 (dd, J = 4.8, 1.3 Hz, 1H), 8.44 (s, 1H), 8.03 (ddd, J = 8.3, 2.7, 1.4 Hz, 1H), 7.69 (d, J = 7.8 Hz, 1H), 7.53 (t, J = 7.3 Hz, 1H), 7.47 (d, J = 8.3 Hz, 1H), 7.45 (ddd, J = 8.3, 4.8, 0.7 Hz, 1H), 7.39 (t, J = 7.3 Hz, 1H), 4.98 (s, 2H), 3.60 (t, J = 6.8 Hz, 2H), 3.05 (t, J = 6.7 Hz, 2H) IR (cm⁻¹): 1650, 1571 |
| F33 | | 360 ([M + H]+) | ¹H NMR (400 MHz, CDCl₃) δ 9.04 (d, J = 2.3 Hz, 1H), 8.78 (d, J = 2.4 Hz, 1H), 8.64 (dd, J = 4.8, 1.4 Hz, 1H), 8.50 (s, 1H), 8.06 (ddd, J = 8.3, 2.7, 1.5 Hz, 1H), 7.94 (dd, J = 8.3, 2.4 Hz, 1H), 7.75 (d, J = 8.4 Hz, 1H), 7.47 (ddd, J = 8.3, 4.8, 0.7 Hz, 1H), 4.19 (t, J = 6.5 Hz, 2H), 3.27 (t, J = 6.5 Hz, 2H) IR (cm⁻¹): 3095, 1662, 1564 |
| F34 | | 293 ([M + H]+) | ¹H NMR (300 MHz, CDCl₃) δ 9.04 (d, J = 2.6 Hz, 1H), 8.74 (d, J = 4.8 Hz, 2H), 8.61 (dd, J = 4.8, 1.3 Hz, 1H), 8.53 (s, 1H), 8.05 (ddd, J = 8.3, 2.6, 1.5 Hz, 1H), 7.44 (dd, J = 8.3, 4.7 Hz, 1H), 7.12 (t, J = 4.8 Hz, 1H), 4.45-4.34 (m, 2H), 3.18 (t, J = 6.4 Hz, 2H) |
| F37 | 224-226 | 360 ([M + H]+) | ¹H NMR (300 MHz, CDCl₃) δ 9.04 (d, J = 2.6 Hz, 1H), 8.72-8.66 (m, 1H), 8.63 (dd, J = 4.8, 1.4 Hz, 1H), 8.52 (s, 1H), 8.12 (d, J = 8.8 Hz, 1H), 8.06 (ddd, J = 8.4, 2.6, 1.5 Hz, 1H), 7.92 (dd, J = 8.8, 2.5 Hz, 1H), 7.45 (dd, J = 8.3, 4.8 Hz, 1H), 4.57-4.45 (m, 2H), 3.23-3.13 (m, 2H) |
| F38 | 233-234 | 370 ([M + H]+) | ¹H NMR (300 MHz, CDCl₃) δ 9.05 (d, J = 2.6 Hz, 1H), 8.93 (d, J = 4.9 Hz, 2H), 8.62 (dd, J = 4.8, 1.3 Hz, 1H), 8.50 (s, 1H), 8.30 (d, J = 7.5 Hz, 1H), 8.10-8.00 (m, 2H), 7.90 (t, J = 7.9 Hz, 1H), 7.45 (dd, J = 8.3, 4.7 Hz, 1H), 7.33 (t, J = 4.9 Hz, 1H), 4.65 (t, J = 6.5 Hz, 2H), 3.21 (t, J = 6.5 Hz, 2H) |
| F39 | 166-169 | 254 ([M + H]+) | ¹H NMR(400 MHz, CDCl3) δ 9.05 (s, 1H), 8.65 (d, J = 4.44 Hz, 1H), 8.45 (s, 1H), 8.07 (d, J = 8.32 Hz, 1H), 7.50 (dd, J = 4.80, 8.22 Hz, 1H), 4.55 (s, 2H), 3.83 (t, J = 6.72 Hz, 2H), 3.21 (t, J = 6.68 Hz, 2H) |
| F40 | | 289 ([M + H]+) | ¹H NMR (400 MHz, CDCl₃) δ 9.00 (d, J = 2.5 Hz, 1H), 8.60 (d, J = 3.3 Hz, 1H), 8.36 (s, 1H), 8.01 (ddd, J = 8.3, 2.8, 1.5 Hz, 1H), 7.43 (dd, J = 8.3, 4.8 Hz, 1H), 3.75 (dt, J = 10.6, 6.8 Hz, 4H), 3.09 (t, J = 6.7 Hz, 2H), 2.81-2.73 (m, 2H), 2.20 (s, 3H) IR (cm⁻¹): 1644, 1571 |
| F42 | 207-210 | 395 ([M + H]+) | ¹H NMR(400 MHz, CDCl3) δ 9.10 (s, 1H), 8.73 (s, 1H), 8.56 (d, J = 4.72 Hz, 1H), 8.30 (dd, J = 1.32, 5.46 Hz, 1H), 7.61 (dd, J = 4.84, 8.36 Hz, 1H), 4.48 (s, 2H), 3.79 (t, J = 6.80 Hz, 2H), 3.59-3.62 (m, 4H), 3.12 (t, J = 6.72 Hz, 2H), 2.83-0.00 (m, 1H), 2.46 (t, J = 4.84 Hz, 2H), 2.39 (t, J = 5.00 Hz, 2H), |

-continued

| Compound | Mp (° C.) | Mass ESIMS (m/z) | NMR, IR (thin film) |
|---|---|---|---|
| F43 | 169-171 | 292 ([M + H]⁺) | 2.09-2.12 (m, 2H), 1.77-1.79 (m, 2H), 1.94-1.94 (m, 2H) <br> $^1$H NMR (300 MHz, CDCl$_3$) δ 9.03 (d, J = 2.6 Hz, 1H), 8.60 (dd, J = 4.7, 1.2 Hz, 1H), 8.50 (s, 1H), 8.44 (m, 1H), 8.05 (ddd, J = 8.3, 2.5, 1.5 Hz, 1H), 7.87 (d, J = 8.3 Hz, 1H), 7.71 (ddd, J = 8.5, 7.5, 1.9 Hz, 1H), 7.43 (dd, J = 8.3, 4.7 Hz, 1H), 7.09 (m, 1H), 4.43 (t, J = 6.5 Hz, 2H), 3.16 (t, J = 6.5 Hz, 2H) |
| F46 | 216-217 | 360 ([M + H]⁺) | $^1$H NMR (300 MHz, CDCl$_3$) δ 9.04 (d, J = 2.6 Hz, 1H), 8.62 (dd, J = 4.8, 1.3 Hz, 1H), 8.52 (s, 1H), 8.19 (d, J = 8.5 Hz, 1H), 8.06 (ddd, J = 8.4, 2.5, 1.6 Hz, 1H), 7.86 (t, J = 8.0 Hz, 1H), 7.48-7.42 (m, 2H), 4.51 (t, J = 6.5 Hz, 2H), 3.18 (t, J = 6.5 Hz, 2H) |
| F48 | | 361 ([M + H]⁺) | $^1$H NMR (400 MHz, CDCl$_3$) δ 9.12 (d, J = 0.6 Hz, 1H), 9.08-9.03 (m, 1H), 8.66 (dd, J = 4.8, 1.4 Hz, 1H), 8.58 (d, J = 1.1 Hz, 1H), 8.55 (s, 1H), 8.08 (ddd, J = 8.3, 2.7, 1.5 Hz, 1H), 7.48 (ddd, J = 8.3, 4.8, 0.7 Hz, 1H), 4.68-4.59 (m, 2H), 3.24-3.14 (m, 2H) <br> IR (cm$^{-1}$): 1686 |
| F49 | | 310 ([M + H]⁺) | $^1$H NMR (400 MHz, CDCl$_3$) δ 9.05 (d, J = 2.4 Hz, 1H), 8.62 (dd, J = 4.8, 1.4 Hz, 1H), 8.50 (s, 1H), 8.29 (d, J = 2.9 Hz, 1H), 8.06 (ddd, J = 8.3, 2.7, 1.5 Hz, 1H), 7.89 (ddd, J = 9.1, 4.1, 0.4 Hz, 1H), 7.50-7.43 (m, 2H), 4.43-4.36 (m, 2H), 3.21-3.12 (m, 2H) <br> IR (cm$^{-1}$): 1669 |
| F50 | | 373 ([M + H]⁺) | $^1$H NMR (400 MHz, CDCl$_3$) δ 9.01 (d, J = 2.3 Hz, 1H), 8.61 (dd, J = 4.7, 1.4 Hz, 1H), 8.42 (s, 1H), 8.02 (ddd, J = 8.3, 2.7, 1.5 Hz, 1H), 7.61 (d, J = 8.1 Hz, 2H), 7.49-7.42 (m, 3H), 4.82 (s, 2H), 3.59 (t, J = 6.7 Hz, 2H), 3.04 (t, J = 6.7 Hz, 2H) <br> IR (cm$^{-1}$): 1647, 1570 |
| F51 | 221 (decomposed) | 307 ([M + H]⁺) | $^1$H NMR (400 MHz, CDCl$_3$) δ 9.01 (d, J = 2.5 Hz, 1H), 8.63 (dd, J = 4.7, 1.3 Hz, 1H), 8.43 (s, 1H), 8.04 (ddd, J = 8.4, 2.5, 1.4 Hz, 1H), 7.46 (dd, J = 8.3, 4.8 Hz, 1H), 4.82 (s, 2H), 4.02 (t, J = 6.6 Hz, 2H), 3.17 (t, J = 6.6 Hz, 2H), 2.96 (s, 3H) |
| F54 | | 277 ([M + H]⁺) | $^1$H NMR (400 MHz, CDCl$_3$) δ 9.00 (d, J = 2.3 Hz, 1H), 8.60 (dd, J = 4.8, 1.4 Hz, 1H), 8.37 (s, 1H), 8.02 (ddd, J = 8.3, 2.6, 1.5 Hz, 1H), 7.44 (ddd, J = 8.3, 4.8, 0.8 Hz, 1H), 3.91-3.72 (m, 6H), 3.10 (t, J = 6.7 Hz, 2H) |
| P18 | 240-242 | 333 ([M + H]⁺) | $^1$H NMR (400 MHz, CDCl$_3$) δ 9.04 (s, 1H), 8.62 (d, J = 4.3 Hz, 1H), 8.43 (s, 1H), 8.09-7.99 (m, 3H), 7.69-7.59 (m, 1H), 7.57-7.49 (m, 2H), 7.46 (dd, J = 8.3, 4.8 Hz, 1H), 5.05 (s, 2H), 3.79 (t, J = 6.7 Hz, 2H), 3.17 (t, J = 6.7 Hz, 2H) |
| P20 | 180-181 | 401 ([M + H]⁺) | $^1$H NMR (400 MHz, CDCl$_3$) δ 9.07 (s, 1H), 8.64 (s, 1H), 8.44 (s, 1H), 8.29 (s, 1H), 8.23 (d, J = 7.9 Hz, 1H), 8.08 (d, J = 8.4 Hz, 1H), 7.90 (d, J = 7.8 Hz, 1H), 7.69 (t, J = 7.8 Hz, 1H), 7.53-7.45 (m, 1H), 5.06 (s, 2H), 3.81 (t, J = 6.7 Hz, 2H), 3.19 (t, J = 6.7 Hz, 2H) |
| P21 | 230-232 | 401 ([M + H]⁺) | $^1$H NMR (400 MHz, CDCl$_3$) δ 9.05 (s, 1H), 8.63 (d, J = 4.2 Hz, 1H), 8.43 (s, 1H), 8.16-8.14 (m, 2H), 8.06-8.04 (m, 1H), 7.81-7.79 (m, 2H), 7.47 (dd, J = 8.3, 4.7 Hz, 1H), 5.05 (s, 2H), 3.81 (t, J = 6.7 Hz, 2H), 3.18 (t, J = 6.7 Hz, 2H) |
| P26 | 155-156 | 286 ([M + H]⁺) | $^1$H NMR (400 MHz, DMSO-d$_6$) δ 9.15 (d, J = 2.4 Hz, 1H), 9.09 (s, 1H), 8.56 (d, J = 4.6 Hz, 1H), 8.30 (d, J = 8.4 Hz, 1H), 7.57 (dd, J = 8.4, 4.7 Hz, 1H), 7.17 (dt, J = 7.9, 4.5 Hz, 1H), 4.25 (dd, J = 31.6, 4.6 Hz, |

-continued

| Compound | Mp (° C.) | Mass ESIMS (m/z) | NMR, IR (thin film) |
|---|---|---|---|
| P27 | 121-122 | 362 ([M + H]+) | 2H), 3.81 (d, J = 34.4 Hz, 3H), 3.67 (dt, J = 23.2, 6.6 Hz, 2H), 3.07-2.96 (m, 2H).<br>¹H NMR (400 MHz, DMSO-d₆) δ 9.15 (d, J = 2.6 Hz, 1H), 9.07 (s, 1H), 8.55 (dd, J = 4.7, 1.3 Hz, 1H), 8.29 (ddd, J = 8.4, 2.6, 1.3 Hz, 1H), 7.61-7.47 (m, 2H), 7.45-7.27 (m, 5H), 5.09 (d, J = 34.0 Hz, 2H), 4.28 (dd, J = 52.2, 4.5 Hz, 2H), 3.64 (dt, J = 39.5, 6.7 Hz, 2H), 2.99 (dt, J = 19.9, 6.7 Hz, 2H) |
| P30 | 130-132 | 300 ([M + H]+) | ¹H NMR (400 MHz, DMSO-d₆) δ 9.15 (d, J = 2.6 Hz, 1H), 9.08 (s, 1H), 8.56 (dd, J = 4.7, 1.3 Hz, 1H), 8.29-8.26 (m, 1H), 7.56 (dd, J = 8.4, 4.7 Hz, 1H), 4.17 (s, 2H), 3.78 (s, 3H), 3.56 (t, J = 6.7 Hz, 2H), 2.99 (t, J = 6.7 Hz, 2H), 1.76 (s, 3H) |
| P31 | 140-142 | 376 ([M + H]+) | ¹H NMR (400 MHz, DMSO-d₆) δ 9.15 (d, J = 2.2 Hz, 1H), 9.08 (s, 1H), 8.55 (d, J = 4.6 Hz, 1H), 8.29 (dd, J = 8.3, 1.3 Hz, 1H), 7.56 (dd, J = 8.3, 4.7 Hz, 1H), 7.43-7.21 (m, 5H), 5.07 (s, 2H), 4.17 (s, 2H), 3.49 (t, J = 6.6 Hz, 2H), 2.93 (t, J = 6.6 Hz, 2H), 1.81 (s, 3H) |
| P32 | 150-152 | 362 ([M + H]+) | ¹H NMR (400 MHz, DMSO-d₆) δ 9.10 (d, J = 2.6 Hz, 1H), 9.03 (s, 1H), 8.54 (dd, J = 4.7, 1.3 Hz, 1H), 8.24-8.22 (m, 1H), 7.65-7.58 (m, 2H), 7.54 (dd, J = 8.3, 4.7 Hz, 1H), 7.42-7.29 (m, 3H), 4.83 (s, 2H), 3.98 (s, 3H), 3.45 (t, J = 6.7 Hz, 2H), 2.68 (t, J = 6.7 Hz, 2H) |
| P34 | 212-213 | 430 ([M + H]+) | ¹H NMR (400 MHz, DMSO-d₆) δ 9.10 (d, J = 2.6 Hz, 1H), 9.05 (s, 1H), 8.54 (dd, J = 4.7, 1.3 Hz, 1H), 8.25 (ddd, J = 8.4, 2.6, 1.4 Hz, 1H), 7.99 (s, 1H), 7.93 (d, J = 8.0 Hz, 1H), 7.75 (d, J = 7.9 Hz, 1H), 7.63 (t, J = 7.8 Hz, 1H), 7.54 (dd, J = 8.4, 4.7 Hz, 1H), 4.84 (s, 2H), 4.02 (s, 3H), 3.52 (t, J = 6.7 Hz, 2H), 2.74 (t, J = 6.7 Hz, 2H) |
| P35 | 160-162 | 430 ([M + H]+) | ¹H NMR (400 MHz, DMSO-d₆) δ 9.10 (d, J = 2.5 Hz, 1H), 9.02 (s, 1H), 8.54 (dd, J = 4.7, 1.2 Hz, 1H), 8.24 (ddd, J = 8.4, 2.6, 1.4 Hz, 1H), 7.86 (d, J = 8.2 Hz, 2H), 7.75 (d, J = 8.4 Hz, 2H), 7.54 (dd, J = 8.3, 4.7 Hz, 1H), 4.84 (s, 2H), 4.03 (s, 3H), 3.51 (t, J = 6.7 Hz, 2H), 2.75 (t, J = 6.6 Hz, 2H) |
| P36 | 176-177 | 438 ([M + H]+) | ¹H NMR (400 MHz, DMSO-d₆) δ 9.11 (dd, J = 7.4, 2.5 Hz, 1H), 9.01 (d, J = 4.0 Hz, 1H), 8.54 (dd, J = 4.7, 1.3 Hz, 1H), 8.33-8.14 (m, 1H), 7.89-7.04 (m, 11H), 5.18 (d, J = 70.3 Hz, 2H), 4.91-4.52 (m, 2H), 3.48 (dt, J = 55.6, 6.6 Hz, 2H), 2.83-2.59 (m, 2H) |
| P38 | 180-182 | 506 ([M + H]+) | ¹H NMR (400 MHz, DMSO-d₆) δ 9.10 (d, J = 2.5 Hz, 1H), 9.04 (s, 1H), 8.54 (dd, J = 4.7, 1.4 Hz, 1H), 8.25 (ddd, J = 8.4, 2.7, 1.4 Hz, 1H), 7.99 (s, 1H), 7.92 (d, J = 7.9 Hz, 1H), 7.75 (d, J = 7.8 Hz, 1H), 7.62 (t, J = 7.7 Hz, 1H), 7.54 (dd, J = 8.4, 4.7 Hz, 1H), 7.49-7.30 (m, 5H), 5.31 (s, 2H), 4.86 (s, 2H), 3.49 (t, J = 6.7 Hz, 2H), 2.69 (t, J = 6.6 Hz, 2H) |
| P39 | 205-206 | 506 ([M + H]+) | ¹H NMR (400 MHz, DMSO-d₆) δ 9.10 (d, J = 2.4 Hz, 1H), 9.01 (s, 1H), 8.54 (dd, J = 4.7, 1.3 Hz, 1H), 8.24 (ddd, J = 8.5, 2.7, 1.4 Hz, 1H), 7.85 (d, J = 8.2 Hz, 2H), 7.76 (d, J = 8.4 Hz, 2H), 7.54 (dd, J = 8.3, 4.7 Hz, 1H), 7.50-7.30 (m, 5H), 5.31 (s, 2H), 4.87 (s, 2H), 3.48 (t, J = 6.7 Hz, 2H), 2.70 (t, J = 6.7 Hz, 2H) |

EXAMPLES OF COMPARATIVE COMPOUNDS

Example 44

Preparation of 2-(pyridin-2-yl)-6,7-dihydro-2H-pyrazolo[4,3-c]pyridin-4(5H)-one (CE1)

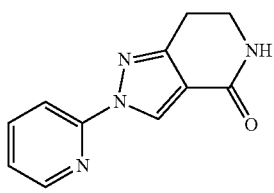 [SMILES: O=C1NCCc2nn(-c3ccccn3)cc21]

CE1

To a solution of piperidine-2,4-dione (2.00 g, 17.7 mmol) and 2-hydrazinylpyridine (1.93 g, 17.7 mmol) in water (19.7 mL) and ethanol (157 mL). The reaction was stirred at room temperature overnight. The reaction mixture was concentrated under reduced pressure. The residue was dried azeotropically with ethanol/toluene to give a yellow powder. Dimethylformamide (7.07 mL) was added followed by 1,1-dimethoxy-N,N-dimethylmethanamine (7.05 mL, 53.0 mmol), and the reaction was heated at 90° C. for 60 minutes. The reaction was cooled to room temperature and concentrated under reduced pressure. The residue was dissolved in methanol, concentrated onto Celite®, and purified by flash column chromatography using 1-15% methanol/dichloromethane as eluent to give Compound CE1 as a yellow solid (0.870 g, 22%).

Example 45

Preparation of 5-(methylsulfanylmethyl)-2-(4-pyridyl)-6,7-dihydropyrazolo[4,3-c]pyridin-4-one (CE2)

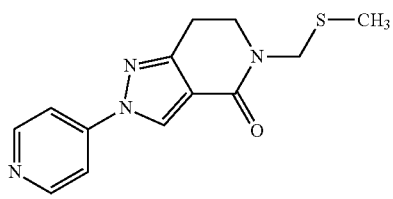 [SMILES: CSCN1CCc2nn(-c3ccncc3)cc2C1=O]

CE2

Compound CE2 was prepared in accordance with the procedure disclosed in Example 10 using (chloromethyl)(methyl)sulfane, and was isolated as an off-white solid (0.014 g, 6%).

Example 46

The following molecules were made in accordance with the procedures disclosed in Example 45.

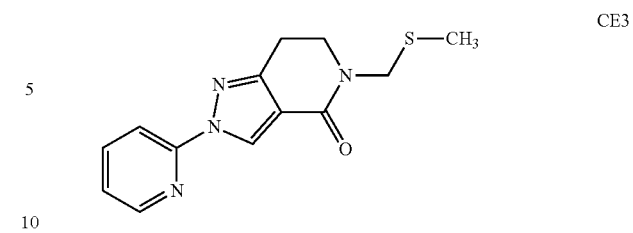

CE3

5-(Methylsulfanylmethyl)-2-(2-pyridyl)-6,7-dihydropyrazolo[4,3-c]pyridin-4-one (Compound CE3) was prepared using (chloromethyl)(methyl)sulfane, and was isolated as a yellow solid (0.0527 g, 27%).

Example 47

Preparation of 2-(2-Pyridyl)-5-[3-(trifluoromethoxy)phenyl]-6,7-dihydropyrazolo[4,3-c]pyridin-4-one (CE4)

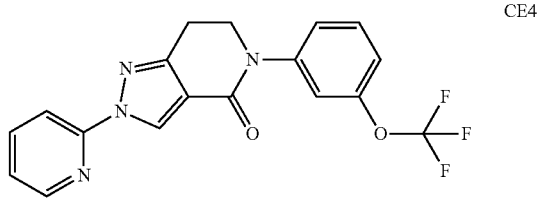

CE4

Compound CE4 was prepared in accordance with the procedure disclosed in Example 10 using 1-bromo-3-(trifluoromethoxy)benzene, and was isolated as a clear oil (0.0224 g, 22%).

Example 48

The following molecules were made in accordance with the procedures disclosed in Example 47:

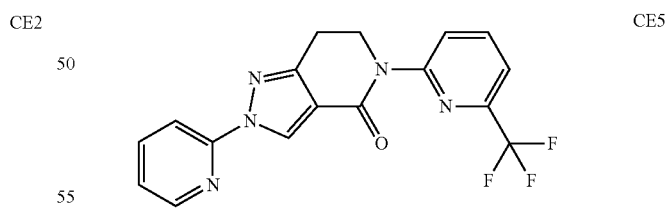

CE5

2-(2-Pyridyl)-5-[6-(trifluoromethyl)-2-pyridyl]-pyrazolo[4,3-c]pyridin-4-one (Compound CE5) was prepared using 2-bromo-6-(trifluoromethyl)pyridine, and was isolated as a yellow solid (0.0691 g, 78%).

Example 49

The following molecules were made in accordance with the procedures disclosed in Example 47:

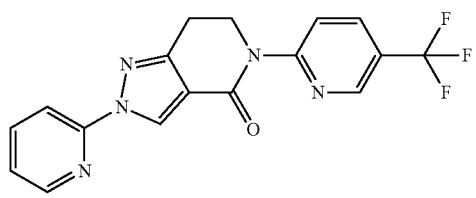

CE6

2-(2-Pyridyl)-5-[5-(trifluoromethyl)-2-pyridyl]-6,7-dihydropyrazolo[4,3-c]pyridin-4-one (Compound E6) was prepared using 2-bromo-5-(trifluoromethyl)pyridine, and was isolated as a green solid (0.0117 g, 13%).

Example 50

The following molecules were made in accordance with the procedures disclosed in Example 47:

2-(2-Pyridyl)-5-[4-(trifluoromethyl)-2-pyridyl]-6,7-dihydropyrazolo[4,3-c]pyridin-4-one (Compound CE7) was prepared using 2-bromo-4-(trifluoromethyl)pyridine, the title compound was isolated as a yellow solid (0.025 g, 28%).

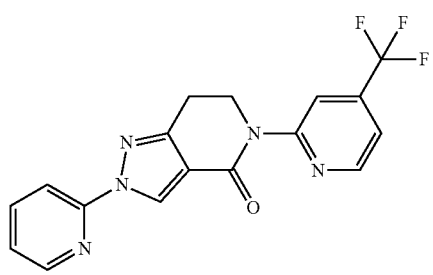

CE7

TABLE 7 shows the structures and preparation methods of the comparative compounds.

| Compound | Structure | Prepared according to Example: |
|---|---|---|
| CE1 | 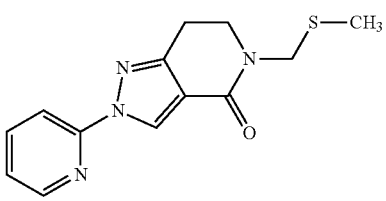 [SMILES: CSCN1CCc2nn(-c3ccccn3)cc2C1=O] | 44 |
| CE2 | (structure) | 45 |
| CE3 | (structure) | 45 |
| CE4 | 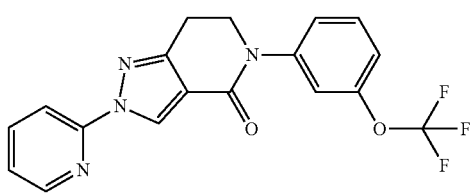 [SMILES: O=C1c2cn(-c3ccccn3)nc2CCN1c1cccc(OC(F)(F)F)c1] | 47 |
| CE5 | 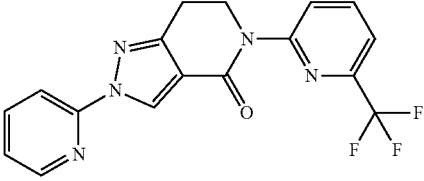 [SMILES: O=C1c2cn(-c3ccccn3)nc2CCN1c1cccc(C(F)(F)F)n1] | 47 |
| CE6 | 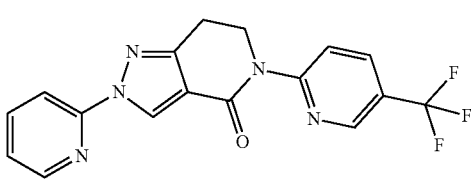 [SMILES: O=C1c2cn(-c3ccccn3)nc2CCN1c1ccc(C(F)(F)F)cn1] | 47 |
| CE7 | (structure) | 47 |

TABLE 8 shows analytical data for comparative compounds in TABLE 7.

| Compound | IR (thin film) (cm⁻¹) | Mass ESIMS (m/z) | ¹H NMR |
|---|---|---|---|
| CE1 | 3196, 3080, 2957, 1677, 1572 | 215 ([M + H]⁺) | ¹H NMR (400 MHz, CDCl₃) δ 9.00 (s, 1H), 8.45 (ddd, J = 4.8, 1.8, 0.8 Hz, 1H), 7.94 (dt, J = 8.3, 0.9 Hz, 1H), 7.83 (ddd, J = 8.3, 7.4, 1.8 Hz, 1H), 7.24 (ddd, J = 7.4, 4.9, 1.0 Hz, 1H), 5.86 (s, 1H), 3.65 (td, J = 6.7, 2.7 Hz, 2H), 3.04 (t, J = 6.7 Hz, 2H) |
| CE2 | 2919, 1652, 1588, 1568 | 275 ([M + H]⁺) | ¹H NMR (300 MHz, CDCl₃) δ 8.69 (dd, J = 4.9, 1.4 Hz, 2H), 8.46 (s, 1H), 7.62 (dd, J = 4.8, 1.5 Hz, 2H), 4.70 (s, 2H), 3.77 (t, J = 6.7 Hz, 2H), 3.09 (t, J = 6.7 Hz, 2H), 2.15 (s, 3H) |
| CE3 | 2919, 1651, 1570 | 275 ([M + H]⁺) | ¹H NMR (300 MHz, CDCl₃) δ 8.96 (s, 1H), 8.44 (ddd, J = 4.7, 1.8, 0.8 Hz, 1H), 7.92 (dt, J = 8.4, 1.0 Hz, 1H), 7.82 (ddd, J = 8.3, 7.4, 1.8 Hz, 1H), 7.27-7.21 (m, 1H), 4.71 (s, 2H), 3.77 (t, J = 6.7 Hz, 2H), 3.09 (t, J = 6.7 Hz, 2H), 2.16 (s, 3H) |
| CE4 | 3065, 1667, 1569 | 375 ([M + H]⁺) | ¹H NMR (400 MHz, CDCl₃) δ 9.06 (s, 1H), 8.46 (ddd, J = 4.8, 1.8, 0.8 Hz, 1H), 7.96 (dt, J = 8.3, 0.9 Hz, 1H), 7.85 (ddd, J = 8.3, 7.4, 1.8 Hz, 1H), 7.43 (t, J = 8.2 Hz, 1H), 7.39-7.30 (m, 1H), 7.29-7.22 (m, 2H), 7.12 (ddt, J = 8.2, 2.1, 1.0 Hz, 1H), 4.10 (t, J = 6.5 Hz, 2H), 3.21 (t, J = 6.5 Hz, 2H) |
| CE5 | 3153, 1679, 1566 | 360 ([M + H]⁺) | ¹H NMR (400 MHz, CDCl₃) δ 9.11 (s, 1H), 8.46 (ddd, J = 4.8, 1.8, 0.8 Hz, 1H), 8.21 (d, J = 8.5 Hz, 1H), 7.98 (dt, J = 8.3, 0.9 Hz, 1H), 7.90-7.81 (m, 2H), 7.44 (d, J = 7.2 Hz, 1H), 7.27 (ddd, J = 7.2, 4.9, 1.0 Hz, 1H), 4.54-4.46 (m, 2H), 3.21-3.14 (m, 2H) |
| CE6 | 3110, 1677, 1565 | 360 ([M + H]⁺) | ¹H NMR (400 MHz, CDCl₃) δ 9.12 (s, 1H), 8.68 (dd, J = 1.5, 0.8 Hz, 1H), 8.47 (ddd, J = 4.8, 1.7, 0.8 Hz, 1H), 8.15 (d, J = 8.8 Hz, 1H), 7.98 (d, J = 8.2 Hz, 1H), 7.94-7.82 (m, 2H), 7.30-7.26 (m, 1H), 4.57-4.44 (m, 2H), 3.24-3.12 (m, 2H) |
| CE7 | 1679, 1566 | 360 ([M + H]⁺) | ¹H NMR (400 MHz, CDCl₃) δ 9.10 (s, 1H), 8.58 (d, J = 5.2 Hz, 1H), 8.47 (ddd, J = 4.8, 1.8, 0.8 Hz, 1H), 8.33-8.26 (m, 1H), 7.98 (dt, J = 8.2, 0.9 Hz, 1H), 7.86 (ddd, J = 8.3, 7.4, 1.8 Hz, 1H), 7.29-7.25 (m, 2H), 4.51-4.45 (m, 2H), 3.20-3.14 (m, 2H) |

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims

We claim:

1. A pesticidal composition, comprising a compound of formula I or any agriculturally acceptable salt thereof:

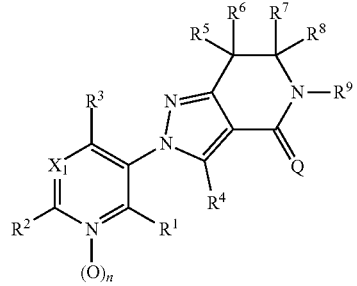

I wherein:
(a) $R^1$, $R^2$, and $R^3$ is each independently selected from the group consisting of H, F, Cl, Br, I, CN, $NO_2$, OH, $C_1$-$C_4$ alkyl, $C_2$-$C_4$ alkenyl, $C_1$-$C_4$ haloalkyl, $C_1$-$C_4$ alkoxy, $C_1$-$C_4$ haloalkoxy, $C_3$-$C_6$ cycloalkyl, aryl, substituted aryl, $C_1$-$C_4$ alkylphenyl, phenyl, substituted phenyl, heterocyclyl, and substituted heterocyclyl,
wherein each said $R^1$, $R^2$, and $R^3$, when substituted, has one or more substituents independently selected from the group consisting of H, F, Cl, Br, I, CN, $NO_2$, OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;
(b) $R^4$, $R^5$, $R^6$, $R^7$, and $R^8$ is each independently selected from the group consisting of H, F, Cl, Br, CN, OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;
(c) $R^9$ is selected from the group consisting of H, $C_1$-$C_4$ alkyl, $C_2$-$C_4$ alkenyl, $C_1$-$C_4$ haloalkyl, ($C_1$-$C_4$ alkyl)($C_3$-$C_6$ cycloalkyl), $C_1$-$C_4$ alkylphenyl, $C_1$-$C_4$ haloalkylphenyl, aryl, substituted aryl, phenyl, pyridiyl, pyrimidyl, substituted phenyl, substituted pyridyl, ($C_1$-$C_4$ alkyl)C(=O)(phenyl), ($C_1$-$C_4$ alkyl)(haloalkyl)(phenyl), ($C_1$-$C_4$ alkyl)(haloalkyl)(alkyl), ($C_1$-$C_4$ alkyl)C(=O)O($C_1$-$C_4$ alkyl), ($C_1$-$C_4$ alkyl)C(=NOR$^{10}$)R$^{11}$, C(=O)($C_1$-$C_4$ alkyl)S(=O)$_m$($C_1$-$C_4$ alkyl), ($C_1$-$C_4$ alkyl)S(=O)$_m$($C_1$-$C_4$ alkyl), ($C_1$-$C_4$ alkyl)S(=O)$_m$($C_1$-$C_4$ haloalkyl), C(=O)R$^{13}$, and ($C_1$-$C_4$ alkyl)C(=O)N(R$^x$R$^y$),
wherein $R^9$, when substituted, has one or more substituents independently selected from the group consisting of F, Cl, CN, OH, $C_1$-$C_4$ haloalkyl, $C_1$-$C_4$ haloalkoxy, and $C_1$-$C_4$ alkoxy, pyrimidyl, or
wherein $R^x$ and $R^y$ together form a 6-membered saturated cyclic group or a 6-membered saturated cyclic group containing one nitrogen heteroatom, and wherein said cyclic group, when substituted, has one or more substituents independently selected from the group consisting of $C_1$-$C_4$ alkyl, $C_3$-$C_6$ cycloalkyl, and phenyl;
(d) $R^{10}$ and $R^{11}$ are independently selected from the group consisting of H, Cl, $C_1$-$C_4$ alkyl, $C_1$-$C_4$ haloalkyl, $C_1$-$C_4$ alkylphenyl, phenyl, and substituted phenyl, aryl, substituted aryl,
wherein $R^{10}$ and $R^{11}$, when substituted, have one or more substituents independently selected from H or $C_1$-$C_4$ haloalkyl;
(e) $R^{13}$ is selected from the group consisting of H, $C_1$-$C_4$ alkyl, $C_2$-$C_4$ alkenyl, $C_1$-$C_4$ haloalkyl, ($C_1$-$C_4$ alkyl)($C_3$-$C_6$ cycloalkyl), $C_1$-$C_4$ alkylphenyl, $C_1$-$C_4$ haloalkylphenyl, phenyl, pyridiyl, pyrimidyl, substituted phenyl, substituted pyridyl, aryl, substituted aryl, ($C_1$-$C_4$ alkyl)C(=O)(phenyl), ($C_1$-$C_4$ alkyl)(haloalkyl)(phenyl), ($C_1$-$C_4$ alkylhaloalkyl)(alkyl), ($C_1$-$C_4$ alkyl)C(=O)O($C_1$-$C_4$ alkyl), ($C_1$-$C_4$ alkyl)C(=NOR$^{10}$)R$^{11}$, C(=O)($C_1$-$C_4$ alkyl)S(=O)$_m$($C_1$-$C_4$ alkyl), ($C_1$-$C_4$ alkyl)S(=O)$_m$($C_1$-$C_4$ alkyl), and ($C_1$-$C_4$ alkyl)S(=O)$_m$($C_1$-$C_4$ haloalkyl);
(f) $X^1$ is N or CR$^{12}$,
wherein $R^{12}$ is selected from the group consisting of H, F, Cl, Br, I, CN, $NO_2$, OH, $C_1$-$C_4$ alkyl, $C_2$-$C_4$ alkenyl, $C_1$-$C_4$ haloalkyl, $C_1$-$C_4$ alkoxy, $C_1$-$C_4$ haloalkoxy, $C_3$-$C_6$ cycloalkyl, $C_1$-$C_4$ alkylphenyl, aryl, substituted aryl, phenyl, substituted phenyl, heteroaryl, and substituted heteroaryl, and
wherein $R^{12}$, when substituted, has one or more substituents independently selected from the group consisting of H, F, Cl, Br, I, CN, $NO_2$, OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;
(g) Q is O (oxygen), or S (sulfur);
(h) n is 0, 1, or 2; and
(i) m is 0, 1, or 2.

2. The composition of claim 1, wherein n is 0 and Q is oxygen.

3. The composition of claim 1, wherein $R^{13}$ is ($C_1$-$C_4$ alkyl)S(=O)$_m$($C_1$-$C_4$ alkyl), and m is 0, 1, or 2.

4. The composition of claim 1, wherein $R^9$ is not hydrogen.

5. The composition of claim 1, wherein $R^9$ is ($C_1$-$C_4$ alkyl)S(=O)$_m$($C_1$-$C_4$ alkyl) or ($C_1$-$C_4$ alkyl)S(=O)$_m$($C_1$-$C_4$ haloalkyl), and wherein m is 0, 1, or 2.

6. The composition of claim 1, wherein $R^9$ is C(=O)R$^{13}$.

7. The composition of claim 1, wherein $R^9$ is $C_1$-$C_4$ haloalkyl.

8. The composition of claim 1, wherein $R^9$ is ($C_1$-$C_4$ alkyl)C(=O)(phenyl).

9. The composition of claim 1, wherein $R^9$ is ($C_1$-$C_4$ alkyl)(haloalkylXalkyl).

10. The composition of claim 1, wherein $R^9$ is ($C_1$-$C_4$ alkyl)C(=NOR$^{10}$)R$^{11}$, and R$^{11}$ is selected from the group consisting of H, $C_1$-$C_4$ alkyl, $C_1$-$C_4$ haloalkyl, phenyl, and substituted phenyl.

11. The composition of claim 1, wherein n is 0 and Q is oxygen or sulfur.

12. The composition of claim 1, wherein:
$R^1$, $R^2$, $R^3$, $R^4$, $R^5$, $R^6$, $R^7$, and $R^8$ is H;
$R^9$ is selected from the group consisting of $C_1$-$C_3$ alkyl, ($C_1$-$C_2$ alkyl)($C_3$-$C_4$ cycloalkyl), $C_1$ alkylphenyl, phenyl, pyrimidyl, substituted phenyl, substituted pyridyl, ($C_1$ alkyl)C(=O)O($C_1$-$C_2$ alkyl), ($C_1$-$C_2$ alkyl)S(=O)$_m$($C_1$ alkyl), ($C_1$-$C_2$ alkyl)S(=O)$_m$($C_1$-$C_3$ haloalkyl), and (C1 alkyl)C(=O)N(R$^x$R$^y$);
$X^1$ is CR$^{12}$, wherein R$^{12}$ is H;
Q is O; and
m is 0, 1, or 2.

13. The composition of claim 1, wherein the compound of formula I is selected from one of the following compounds:

| Compound | Structure |
|---|---|
| F1 | 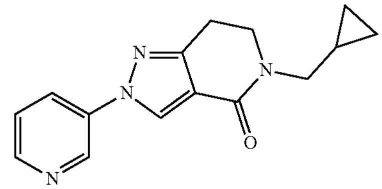 [SMILES: O=C1c2cn(-c3cccnc3)nc2CCN1CC1CC1] |
| F6 | 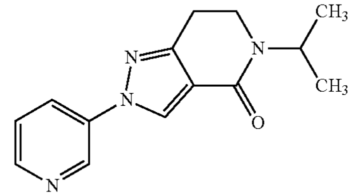 [SMILES: CC(C)N1CCc2nn(-c3cccnc3)cc2C1=O] |

-continued
| Compound | Structure |
|---|---|
| F7 | 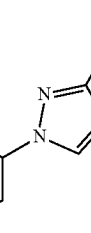 |
| F8 | 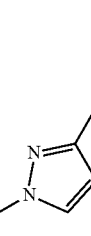 |
| F19 | 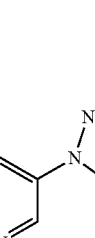 |
| F20 | 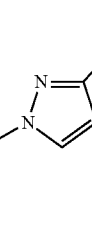 |
| F21 | 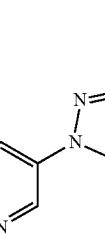 |
| F22 | 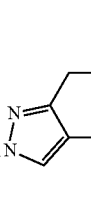 |
-continued
| Compound | Structure |
|---|---|
| F23 | 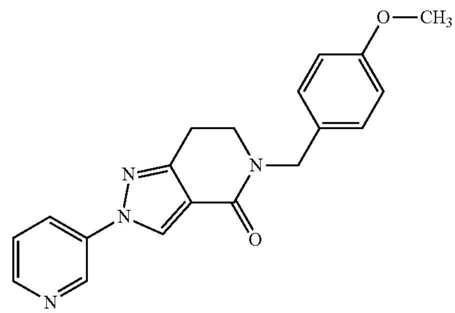 [SMILES: COc1ccc(CN2CCc3nn(-c4cccnc4)cc3C2=O)cc1] |
| F29 | 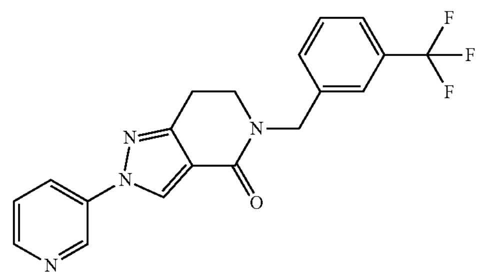 [SMILES: O=C1c2cn(-c3cccnc3)nc2CCN1Cc1cccc(C(F)(F)F)c1] |
| F34 | 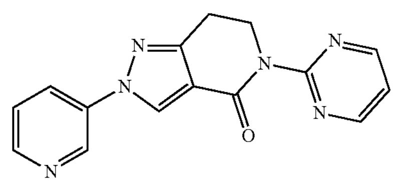 [SMILES: O=C1c2cn(-c3cccnc3)nc2CCN1c1ncccn1] |
| F37 | 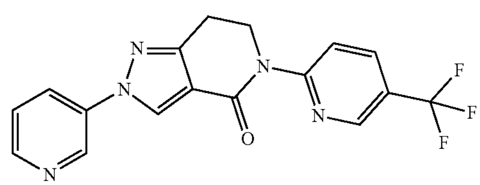 [SMILES: O=C1c2cn(-c3cccnc3)nc2CCN1c1ccc(C(F)(F)F)cn1] |
| F40 | 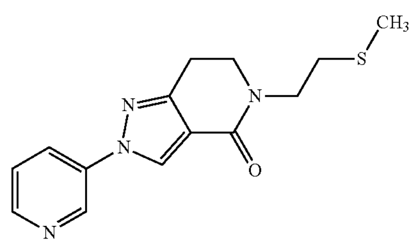 [SMILES: CSCCN1CCc2nn(-c3cccnc3)cc2C1=O] |
| F42 | 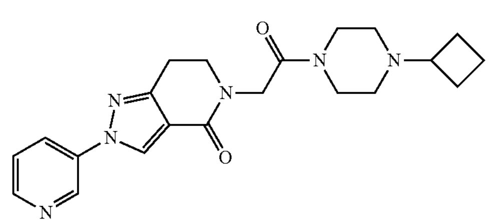 [SMILES: O=C(CN1CCc2nn(-c3cccnc3)cc2C1=O)N1CCN(C2CCC2)CC1] |

-continued
| Compound | Structure |
|---|---|
| F51 | 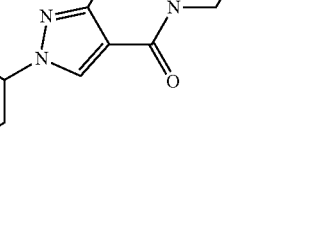 |
| P18 | 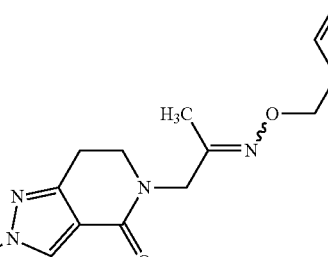 |
| P20 | 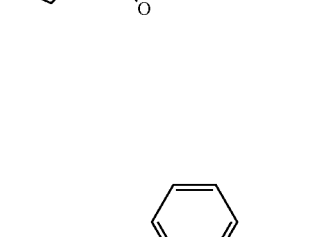 |
| P21 | 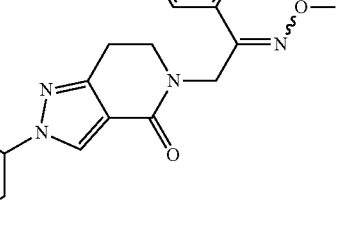 |
| P26 | 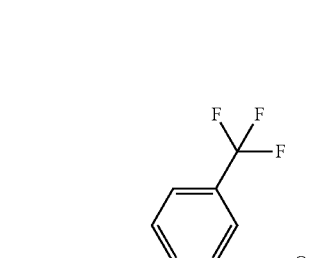 |
| P27 | 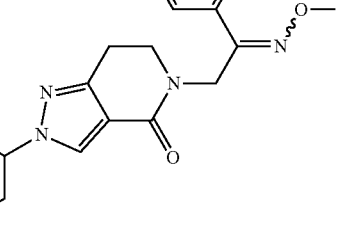 |
-continued
| Compound | Structure |
|---|---|
| P30 | 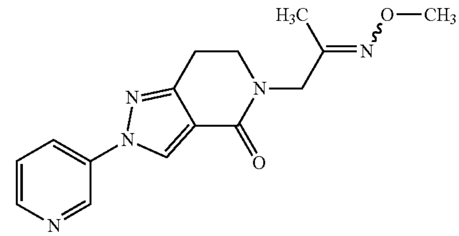 [SMILES: CON=C(C)CN1CCc2nn(-c3cccnc3)cc2C1=O] |
| P31 | 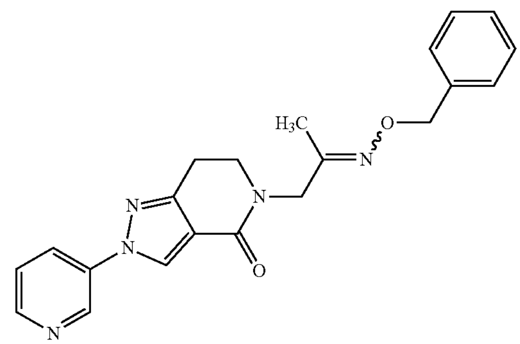 [SMILES: CC(CN1CCc2nn(-c3cccnc3)cc2C1=O)=NOCc1ccccc1] |
| P32 | 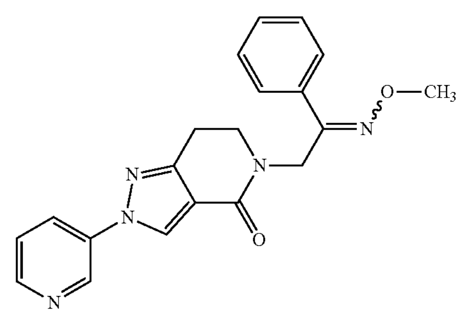 [SMILES: CON=C(CN1CCc2nn(-c3cccnc3)cc2C1=O)c1ccccc1] |
| P34 | 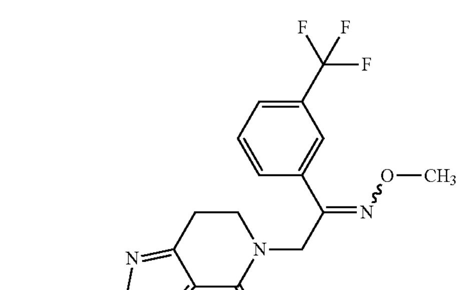 |

| Compound | Structure |
|---|---|
| P35 | 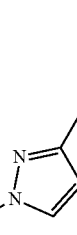 |
| P36 | |
| P38 | |
| P39 | |
| Compound | Structure |
|---|---|
| CA1 |  |
| CA2 | |
| CA3 | |
| CA4 | |
14. The composition of claim 1, wherein the compound of formula I is selected from one of the following compounds:
| Compound | Structure |
|---|---|
| F19 | 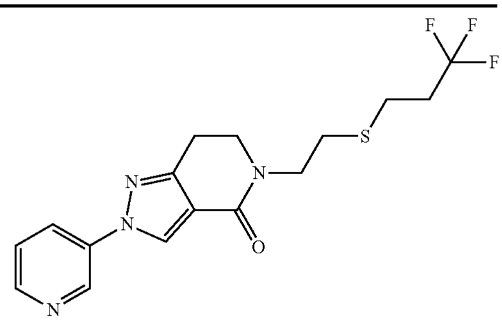 |
| F20 | 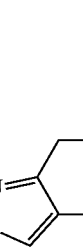 |

| Compound | Structure |
|---|---|
| F51 | 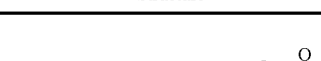 |

15. The composition of claim 1, further comprising:
(a) one or more compounds having acaricidal, algicidal, avicidal, bactericidal, fungicidal, herbicidal, insecticidal, molluscicidal, nematicidal, rodenticidal, or virucidal properties; or
(b) one or more compounds that are antifeedants, bird repellents, chemosterilants, herbicide safeners, insect attractants, insect repellents, mammal repellents, mating disrupters, plant activators, plant growth regulators, or synergists; or
(c) both (a) and (b).

16. The composition of claim 1, further comprising one or more compounds selected from: (3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, azipro-tryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopten, difenopten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiobac, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

17. The composition of claim 1, further comprising at least one of the following compounds:
   (a) 3-(4-chloro-2,6-dimethylphenyl)-4-hydroxy-8-oxa-1-azaspiro[4,5]dec-3-en-2-one;
   (b) 3-(4'-chloro-2,4-dimethyl[1,1'-biphenyl]-3-yl)-4-hydroxy-8-oxa-1-azaspiro[4,5]dec-3-en-2-one;
   (c) 4-[[(6-chloro-3-pyridinyl)methyl]methylamino]-2(5H)-furanone;
   (d) 4-[[(6-chloro-3-pyridinyl)methyl]cyclopropylamino]-2(5H)-furanone;
   (e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
   (f) 2-cyano-N-ethyl-4-fluoro-3-methoxy-benenesulfonamide;
   (g) 2-cyano-N-ethyl-3-methoxy-benzenesulfonamide;
   (h) 2-cyano-3-difluoromethoxy-N-ethyl-4-fluoro-benzenesulfonamide;
   (i) 2-cyano-3-fluoromethoxy-N-ethyl-benzenesulfonamide;
   (j) 2-cyano-6-fluoro-3-methoxy-N,N-dimethyl-benzenesulfonamide;
   (k) 2-cyano-N-ethyl-6-fluoro-3-methoxy-N-methyl-benzenesulfonamide;
   (l) 2-cyano-3-difluoromethoxy-N,N-dimethylbenzenesulfon-amide;
   (m) 3-(difluoromethyl)-N-[2-(3,3-dimethylbutyl)phenyl]-1-methyl-1H-pyrazole-4-carboxamide;
   (n) N-ethyl-2,2-dimethylpropionamide-2-(2,6-dichloro-α,α,α-trifluoro-p-tolyl) hydrazone;
   (o) N-ethyl-2,2-dichloro-1-methylcyclopropane-carboxamide-2-(2,6-dichloro-α,α,α-trifluoro-p-tolyl) hydrazone nicotine;
   (p) O-{(E-)-[2-(4-chloro-phenyl)-2-cyano-1-(2-trifluoromethylphenyl)-vinyl]}S-methyl thiocarbonate;
   (q) (E)-N1-[(2-chloro-1,3-thiazol-5-ylmethyl)]-N2-cyano-N1-methylacetamidine;
   (r) 1-(6-chloropyridin-3-ylmethyl)-7-methyl-8-nitro-1,2,3,5,6,7-hexahydro-imidazo[1,2-a]pyridin-5-ol;
   (s) 4-[4-chlorophenyl-(2-butylidine-hydrazono)methyl)] phenyl mesylate; and
   (t) N-Ethyl-2,2-dichloro-1-methylcyclopropanecarboxamide-2-(2,6-dichloro-α,α,α-trifluoro-p-tolyl)hydrazine.

18. The composition of claim 1, further comprising a compound having one or more of the following modes of action: acetylcholinesterase inhibitor, sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor, nicotinic acetylcholine receptor, Midgut membrane disrupter, oxidative phosphorylation disrupter, and ryanodine receptor (RyRs).

19. A process comprising applying the pesticidal composition of claim 1 to an area to control a pest, in an amount sufficient to control such pest.

20. A process comprising applying the pesticidal composition of claim 13 to an area to control a pest, in an amount sufficient to control such pest.

* * * * *